United States Patent
Alvarez Sanchez et al.

(10) Patent No.: US 8,410,117 B2
(45) Date of Patent: Apr. 2, 2013

(54) IMIDAZOPYRIMIDINE DERIVATIVES

(75) Inventors: Ruben Alvarez Sanchez, Rosenau (FR); Konrad Bleicher, Freiburg (DE); Alexander Flohr, Loerrach (DE); Luca Gobbi, Muttenz (CH); Katrin Groebke Zbinzen, Liestal (CH); Matthias Koerner, Grenzach-Wyhlen (DE); Bernd Kuhn, Reinach BL (CH); Jens-Uwe Peters, Grenzach-Wyhlen (DE); Markus Rudolph, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 204 days.

(21) Appl. No.: 13/049,941

(22) Filed: Mar. 17, 2011

(65) Prior Publication Data
US 2011/0237564 A1   Sep. 29, 2011

(30) Foreign Application Priority Data
Mar. 26, 2010   (EP) ..................... 10158011

(51) Int. Cl.
*A01N 43/90* (2006.01)
*A61K 31/519* (2006.01)
*C07D 487/00* (2006.01)

(52) U.S. Cl. ..................... 514/259.1; 544/281

(58) Field of Classification Search ........... None
See application file for complete search history.

(56) References Cited

FOREIGN PATENT DOCUMENTS

| WO | 01/90108 | 11/2001 |
|---|---|---|
| WO | 2002/092086 | 11/2002 |
| WO | 02/100860 | 12/2002 |
| WO | 2005/012485 | 2/2005 |
| WO | 2007/093542 | 8/2007 |

OTHER PUBLICATIONS

Hanzlowsky et al., Journal of Heterocyclic Chem 40(3):487-498 (2003).
Kehler et al., "Expert Opinion on Therapeutic Patents" 19(12):1715-1725 (2009).
Fawcett, L. et al., Proc Natl Academy Sci USA 97(7):3702-3707 (2000).
Sano et al., "J. Neurochem." 105:546-556 (2008).
Coskran et al., "J. Histochem. Cytochem." 54(11):1205-1213 (2006).
Fujishige et al., "Eur. J. Biochem." 266(3):1118-1127 (1999).
Vandenberg et al., "Expert Opinion on Therapeutic Targets" 5(4):507-518 (2001).
Siuciak et al., "Neuropharmacology" 51(2):386-396 (2006).
Seeger et al., "Brain Research" 985:113-126 (2003).
Conti et al., "Prog. Nucleic Acid Res. Mol. Biol." 63:1-38 (1999).
Loughney et al., "Gene" 234(1):109-117 (1999).
Nakazato et al., "Expert Opinion on Therapeutic Patents" 10(1):75-98 (2000).
Siuciak et al., "Neuropharmacology" 51(2):374-385 (2006).
Soderling et al., "Current Opinion Cell Biol." 12:174-179 (2000).
Javitt et al., "Biol. Psychiatry" 45:668-679 (1999).
Lewis et al., "Neuron" 28:325-333 (2000).
Manallack et al., "J. Med. Chem." 48(10):3449-3462 (2005).
Rodefer et al., "Eur. J. Neuroscience" 2:1070-1076 (2005).
Fujishige et al., "J. Biol. Chem." 274:18438-18445 (1999).
Graybiel, A. M., "Curr. Biol." 10:R509-R511 (2000).
Sharma et al., "Psychiatry" 174(SUPPL 28):44-51 (1999).
Beavo et al., "Physiol. Review" 75:725-748 (1995).
Soderling et al., "Proc. Natl. Acad. Sci. USA" 96(12):7071-7076 (1999).

*Primary Examiner* — Jeffrey Murray
(74) *Attorney, Agent, or Firm* — George W. Johnston; Patricia S. Rocha-Tramaloni; Kimberly J. Prior

(57) ABSTRACT

The invention is concerned with novel imidazopyrimidine derivatives of formula (I)

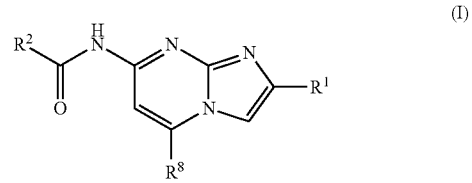

wherein $R^1$, $R^2$ and $R^8$ are as defined in the description and in the claims, as well as physiologically acceptable salts and esters thereof. These compounds inhibit PDE10A and can be used as pharmaceuticals.

26 Claims, No Drawings

IMIDAZOPYRIMIDINE DERIVATIVES

PRIORITY TO RELATED APPLICATION(S)

This application claims the benefit of European Patent Application No. 10158011.6, filed Mar. 26, 2010, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron,* 28:325-33, 2000). For decades research has focused on the "dopaminergic hyperactivity" hypothesis which has led to therapeutic interventions involving blockade of the dopaminergic system (Vandenberg R J and Aubrey K R., *Exp. Opin. Ther. Targets,* 5(4): 507-518, 2001; Nakazato A and Okuyama S, et al., *Exp. Opin. Ther. Patents,* 10(1): 75-98, 2000). This pharmacological approach, besides ameliorating positive symptoms in schizophrenic patients, poorly addresses negative and cognitive symptoms which are the best predictors of functional outcome (Sharma T., *Br. J. Psychiatry,* 174 (suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., *Biol. Psychiatry,* 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., *Physiol. Rev.* 1995, 75, 725-748; Conti, M., Jin, S. L., *Prog. Nucleic Acid Res. Mol. Biol.* 1999, 63, 1-38; Soderling, S. H., Beavo, J. A., *Curr. Opin. Cell Biol.* 2000, 12, 174-179, Manallack, D. T. et al. *J. Med. Chem.* 2005, 48 (10), 3449-3462).

The PDE families differ in their substrate specificy for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., *Eur J Biochem* (1999) 266(3):1118-1127, Soderling S. H., et al., *Proc Natl Acad Sci USA* (1999) 96(12):7071-7076, Loughney K., et al., *Gene* (1999) 234(1):109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., *J. Biol. Chem.* 1999, 274, 18438-18445, Sweet, L. (2005) WO 2005/012485). On the other hand expression of PDE10A protein has been observed only in enteric ganglia, in testis and epididymal sperm (Coskran T. M, et al., *J. Histochem. Cytochem.* 2006, 54 (11), 1205-1213).

In the striatum both mRNA and protein are expressed only in the GABA (-aminobutyric acid)-containing medium spiny projection neurons making it an intriguing target for the treatment of diseases of the central nervous system (Fujishige, K. et al., *Eur. J. Biochem.* 1999, 266, 1118-1127; Seeger, T. F. et al., *Brain Res.* 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. *Curr. Biol.* 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition Inhibition of this enzyme pharmacologically or through gene disruption causes a reduction in activity and a reduced response to psychomotor stimulants. Inhibition also reduces the conditioned avoidance response, a behavioural response that is predictive of clinical antipsychotic activity (Siuciak, J. A.; et al., *Neuropharmacology* 2006, 51 (2), 386-396; Siuciak, J. A.; et al., *Neuropharmacology* 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J, S., et al., *Eur. J. Neuroscience* 2005, 2: 1070-1076). In addition increased social interaction in PDE10A2-deficient mice have been observed (Sano, H. *J. Neurochem.* 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

SUMMARY OF THE INVENTION

The invention provides novel imidazopyrimidine derivatives of formula (I)

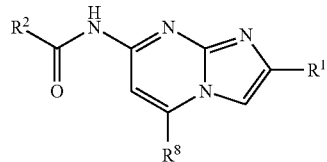

(I)

wherein $R^1$ is phenyl or thienyl, wherein said phenyl and said thienyl are optionally substituted by 1 to 3 substituents independently selected from the group consisting of hydroxyl, halogen, lower alkyl, lower alkoxy, lower haloalkyl, lower haloalkoxy, lower alkoxy lower alkyl, —OC(O)-lower alkyl, —OCH$_2$C(O)-lower alkoxy and phenyl;

$R^2$ is 5- or 6-membered monocyclic heteroaryl having 1 to 3 heteroatoms independently selected from N and O, wherein said heteroaryl is optionally substituted by 1 to 3 substituents independently selected from the group consisting of

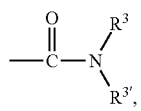

halogen, hydroxyl, nitro, lower alkyl, lower alkenyl, lower alkoxy, lower alkoxy-C(O)—, lower hydroxyalkyl, lower haloalkyl, lower alkoxy lower alkyl, lower alkyl-C(O)—, cycloalkyl, heterocyclyl, aryl, heteroaryl and amino optionally substituted by heteroaryl, wherein two substituents of $R^2$, together with said heteroaryl to which they are attached, may form a 9- or 10-membered bicyclic ring;

$R^3$ and $R^{3'}$ are each independently hydrogen, lower alkyl, lower hydroxyalkyl, lower cyanoalkyl, lower haloalkyl, lower alkoxy lower alkyl, cycloalkyl, cyanocycloalkyl, heterocyclyl or aryl, wherein said lower alkyl is optionally substituted by lower haloalkoxy, cycloalkyl, aryl or heteroaryl, wherein said heteroaryl is optionally substituted by 1 to 3 substituents independently selected from the group consisting of halogen, nitro, cyano, lower alkyl, lower haloalkyl, lower alkoxy and cycloalkyl, and wherein said heterocyclyl is optionally substituted by lower alkyl, or $R^3$ and $R^{3'}$, together with the nitrogen atom to which they are attached, form a heterocyclyl, 2,5-dihydro-1H-pyrrole, 2-methyl-2,4,5,6-tetrahydropyrrolo[3,4-c]pyrazole or 2-oxa-6-azaspiro[3.3]heptane, wherein said heterocyclyl is optionally substituted by 1 to 3 halogen, hydroxyl, oxo, lower alkyl or heteroaryl; and $R^8$ is hydrogen, lower alkyl, lower alkoxy or lower alkoxy lower alkyl;

or pharmaceutically acceptable salts thereof.

In addition to compounds of formula I per se and pharmaceutically acceptable salts thereof. The invention provides pharmaceutical compositions containing the compounds of the invention and processes for the manufacture of the compounds and compositions.

The invention provides methods for the treatment of diseases associated with PDE10A inhibition. Such disease include but are not limited to certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

The invention also provides for the treatment of neurodegenerative disorders including, but not limited to, Alzheimer's disease, Huntington's disease, Parkinson's disease, multiple sclerosis, stroke or spinal cord injury. The invention further provides methods for the treatment of solid tumors and hematological malignancies, such as renal cell carcinoma or breast cancer. The provides methods for the treatment of diabetes and related disorders such as obesity by regulating the cAMP signaling system.

DETAILED DESCRIPTION OF THE INVENTION

Unless otherwise indicated, the following definitions are set forth to illustrate and define the meaning and scope of the various terms used to describe the invention herein.

It must be noted that, as used in the specification and the appended claims, the singular forms "a", "an", and "the" include plural referents unless the context clearly dictates otherwise.

When indicating the number of subsituents, the term "one or more" means from one substituent to the highest possible number of substitution, i.e. replacement of one hydrogen up to replacement of all hydrogens by substituents.

In this specification the term "lower" is used to mean a group consisting of one to seven, more specifically of one to four carbon atom(s).

The term "halogen" refers to fluorine, chlorine, bromine and iodine, more speficially fluorine, chlorine and bromine.

The term "alkyl", alone or in combination with other groups, refers to a branched or straight-chain monovalent saturated aliphatic hydrocarbon radical of one to twenty carbon atoms, more specifically one to sixteen carbon atoms, yet more specifically one to ten carbon atoms.

The term "lower alkyl", alone or in combination with other groups, refers to a branched or straight-chain monovalent alkyl radical of one to seven carbon atoms, more specifically one to four carbon atoms. This term is further exemplified by such radicals as methyl, ethyl, n-propyl, isopropyl, n-butyl, s-butyl, t-butyl and the like.

The term "alkenyl", alone or in combination with other groups, refers to a straight-chain or branched hydrocarbon residue comprising an olefinic bond and up to 20, preferably up to 16 carbon atoms. The term "lower alkenyl" refers to a straight-chain or branched hydrocarbon residue comprising an olefinic bond and up to 7, preferably up to 4 carbon atoms, such as e.g. ethenyl or 2-propenyl.

The term "cycloalkyl", alone or in combination with other groups, refers to a monovalent carbocyclic radical of 3 to 10 carbon atoms, more specifically 3 to 6 carbon atoms, such as cyclopropyl, cyclobutyl, cyclopentyl or cyclohexyl.

The term "cyanocycloalkyl" refers to cycloalkyl which is mon- or multiply substituted with cyano. Examples of cyanoalkyl is e.g. 1-cyanocyclopropyl.

The term "lower haloalkyl", alone or in combination with other groups, refers to lower alkyl groups as defined above which are mono- or multiply substituted with halogen, particularly fluoro. Examples of lower haloalkyl groups are e.g. $-CFH_2$, $-CF_2H$, $-CF_3$, $CF_3CH_2-$, $CF_3(CH_2)_2-$, $(CF_3)_2CH-$ and $CF_2H-CH_2-$.

The term "alkoxy" refers to the group R'—O—, wherein R' is an alkyl as defined herein. The term "lower alkoxy", alone or in combination with other groups, refers to the group R'—O—, wherein R' is a lower alkyl.

The term "lower alkoxy lower alkyl" refers to lower alkyl groups which are mono- or multiply substituted with lower alkoxy. Examples of lower alkoxy lower alkyl groups are e.g. $-CH_2-O-CH_3$, $-CH_2-CH_2-O-CH_3$, and $-CH_2-O-CH_2-CH_3$.

The term "lower hydroxyalkyl" refers to a lower alkyl group as defined above, which is substituted by 1 to 3 hydroxy groups. Examples of lower hydroxyalkyl groups are e.g. hydroxy-methyl, 2-hydroxy-ethyl, hydroxy propyl, 3-hydroxy-propyl, 2-hydroxy-propyl, 3-hydroxy-prop-2-yl, 2,3-dihydroxy-propyl and 1,3-dihydroxy-prop-2-yl.

The term "lower haloalkoxy" refers to a group of the formula lower haloalkyl-O—.

The term "lower cyanoalkyl" refers to a lower alkyl group as defined above, which is substituted by 1 to 3 cyano groups. Examples of lower cyanoalkyl groups are e.g. cyanomethyl and cyanoethyl.

The term "amino" refers to a monovalent group that has a nitrogen atom with two hydrogen atoms (represented by $-NH_2$).

The term "oxo" when referring to substituents on heterocyclyl means that an oxygen atom is attached to the heterocyclyl ring. Thereby, the "oxo" may either replace two hydrogen atoms on a carbon atom, or it may simply be attached to sulfur, so that the sulfur exists in oxidized form, i.e. bearing one or two oxygens.

The term "heterocyclyl" refers to a monovalent saturated 4- to 6-membered monocyclic ring containing one, two or three ring heteroatoms independently selected from N, O and S, the remaining ring atoms being carbon atoms, wherein the point of attachment can be through either a carbon atom or a heteroatom. Examples of heterocyclyl are e.g. morpholinyl, tetrahydropyranyl and piperidinyl.

The term "aryl" refers to a monovalent aromatic hydrocarbon ring(s). The aryl group more specifically includes 6 to 10 carbon atoms. Examples of aryl groups are e.g. phenyl and naphthyl.

The term "heteroaryl" refers to an aromatic 5- or 6-membered monocyclic ring or 9- or 10-membered bicyclic ring wherein at least one ring is aromatic which comprises 1 to 4 atoms independently selected from nitrogen, oxygen and/or sulphur, such as furyl, pyridinyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, thiadiazolyl, benzoimidazolyl, indolyl, indazolyl, benzothiazolyl, benzoisothiazolyl, benzoxazolyl, benzoisoxazolyl, quinolinyl and isoquinolinyl. Examples of heteroaryl groups are pyridinyl, pyrimidinyl, pyrazinyl, quinolinyl or imidazolyl.

The term "bicyclic ring" refers to two rings, wherein the two rings are fused. Each ring is independently aromatic or non-aromatic. In certain embodiments, both rings are aromatic. In certain embodiments, both rings are non-aromatic. In certain embodiments, one ring is aromatic and one ring is non-aromatic.

Compounds of formula (I) can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na-, K-, Ca- and trimethylammonium salt. The term "pharmaceutically acceptable salts" also refers to such salts. Particular salts are those obtained by the addition of an acid.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. Particular esters are methyl, ethyl, propyl, butyl and benzyl esters. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

"Pharmaceutically acceptable," such as pharmaceutically acceptable carrier, excipient, etc., means pharmacologically acceptable and substantially non-toxic to the subject to which the particular compound is administered.

"Therapeutically effective amount" means an amount that is effective to prevent, alleviate or ameliorate symptoms of disease or prolong the survival of the subject being treated.

In detail, the present invention provides compounds of formula (I)

wherein
R$^1$ is phenyl or thienyl, wherein said phenyl and said thienyl are optionally substituted by 1 to 3 substituents independently selected from the group consisting of hydroxyl, halogen, lower alkyl, lower alkoxy, lower haloalkyl, lower haloalkoxy, lower alkoxy lower alkyl, —OC(O)-lower alkyl, —OCH$_2$C(O)-lower alkoxy and phenyl;
R$^2$ is 5- or 6-membered monocyclic heteroaryl having 1 to 3 heteroatoms independently selected from N and O, wherein said heteroaryl is optionally substituted by 1 to 3 substituents independently selected from the group consisting of

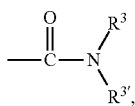

halogen, hydroxyl, nitro, lower alkyl, lower alkenyl, lower alkoxy, lower alkoxy-C(O)—, lower hydroxyalkyl, lower haloalkyl, lower alkoxy lower alkyl, lower alkyl-C(O)—, cycloalkyl, heterocyclyl, aryl, heteroaryl and amino optionally substituted by heteroaryl, wherein two substituents of R$^2$, together with said heteroaryl to which they are attached, may form a 9- or 10-membered bicyclic ring;
R$^3$ and R$^{3'}$ are each independently hydrogen, lower alkyl, lower hydroxyalkyl, lower cyanoalkyl, lower haloalkyl, lower alkoxy lower alkyl, cycloalkyl, cyanocycloalkyl, heterocyclyl or aryl, wherein said lower alkyl is optionally substituted by lower haloalkoxy, cycloalkyl, aryl or heteroaryl, wherein said heteroaryl is optionally substituted by 1 to 3 substituents independently selected from the group consisting of halogen, nitro, cyano, lower alkyl, lower haloalkyl, lower alkoxy and cycloalkyl, and wherein said heterocyclyl is optionally substituted by lower alkyl, or
R$^3$ and R$^{3'}$, together with the nitrogen atom to which they are attached, form a heterocyclyl, 2,5-dihydro-1H-pyrrole, 2-methyl-2,4,5,6-tetrahydropyrrolo[3,4-c]pyrazole or 2-oxa-6-azaspiro[3.3]heptane, wherein said heterocyclyl is optionally substituted by 1 to 3 halogen, hydroxyl, oxo, lower alkyl or heteroaryl; and
R$^8$ is hydrogen, lower alkyl, lower alkoxy or lower alkoxy lower alkyl;
or pharmaceutically acceptable salts thereof.

The compounds of formula (I) can have one or more asymmetric C atoms and can therefore exist as an enantiomeric mixture, mixture of stereoisomers or as optically pure compounds.

A particular embodiment of the present invention provides compounds of formula (I) as described above, wherein R$^1$ is selected from the group consisting of:

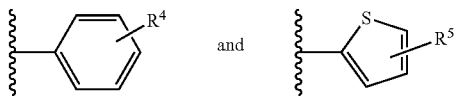

wherein R$^4$ is hydrogen, hydroxyl, halogen, lower alkoxy, lower haloalkoxy, —OC(O)-lower alkyl, —OCH$_2$C(O)-lower alkoxy or phenyl, and R$^5$ is halogen. More specifically, R$^4$ is hydrogen, hydroxyl, chloro, fluoro, bromo, methoxy, fluoromethoxy, trifluoromethoxy, 2-fluoroethoxy, —OC(O)CH$_3$, —OCH$_2$C(O)OCH$_3$ or phenyl, and R$^5$ is chloro. Further more specifically, R$^1$ is phenyl, 3-chloro-phenyl, 3-fluorophenyl, 3-bromophenyl, 4-fluoro-phenyl, 3-methoxy-phenyl, 3-trifluoromethoxy-phenyl, 5-chloro-thiophen-2-yl, 3-(fluoromethoxy)phenyl, 3-hydroxy-phenyl, 3-(2-fluoroethoxy)phenyl, 3-acetoxyphenyl, 3-acetoxymethoxyphenyl, or biphenyl-3-yl.

Particular compounds of formula (I) are described in the examples as individual compounds as well as pharmaceutically acceptable salts as well as pharmaceutically acceptable esters thereof. Furthermore, the substituents as found in the specific examples described below, individually constitute particular embodiments of the present invention.

Another embodiment of the present invention provides compounds of formula (I) as described above, wherein R$^8$ is hydrogen or lower alkoxy lower alkyl, more specifically hydrogen or methoxymethyl, yet more specifically hydrogen.

Another embodiment of the present invention provides compounds of formula (Ia) or pharmaceutically acceptable salts thereof

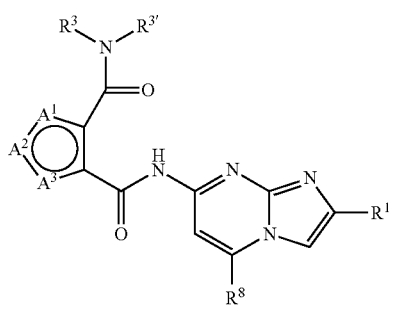

wherein
A$^1$ is —NH—, —N=, —NR$^6$— or —CH=;
A$^2$ is —N= or —NR$^{6'}$—;
A$^3$ is —N=, —NR$^{6''}$— or —CH=;
R$^6$ is lower alkyl;
R$^{6'}$ is lower alkyl;
R$^{6''}$ is lower alkyl or lower alkenyl;
R$^1$ is phenyl or thienyl, wherein said phenyl and said thienyl are optionally substituted by 1 to 3 substituents independently selected from the group consisting of hydroxyl, halogen, lower alkoxy, lower haloalkoxy, —OC(O)-lower alkyl, —OCH$_2$C(O)-lower alkoxy and phenyl;
R$^3$ and R$^{3'}$ are each independently hydrogen, lower alkyl, lower hydroxyalkyl, lower cyanoalkyl, lower haloalkyl, lower alkoxy lower alkyl, cycloalkyl, cyanocycloalkyl, heterocyclyl or aryl, wherein said lower alkyl is optionally substituted by lower haloalkoxy, cycloalkyl, aryl or heteroaryl, wherein said heteroaryl is optionally substituted by 1 to 3 substituents independently selected from the group consisting of halogen, nitro, cyano, lower alkyl, lower haloalkyl, lower alkoxy and cycloalkyl, and wherein said heterocyclyl is optionally substituted by lower alkyl, or R³ and R³', together with the nitrogen atom to which they are attached, form a heterocyclyl, 2,5-dihydro-1H-pyrrole, 2-methyl-2,4,5,6-tetrahydropyrrolo[3,4-c]pyrazole or 2-oxa-6-azaspiro[3.3]heptane, wherein said heterocyclyl is optionally substituted by 1 to 3 halogen, hydroxyl, oxo, lower alkyl or heteroaryl; and R⁸ is hydrogen, lower alkyl, lower alkoxy or lower alkoxy lower alkyl.

More specifically

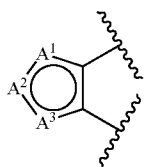

of formula (Ia) is selected from the group consisting of:

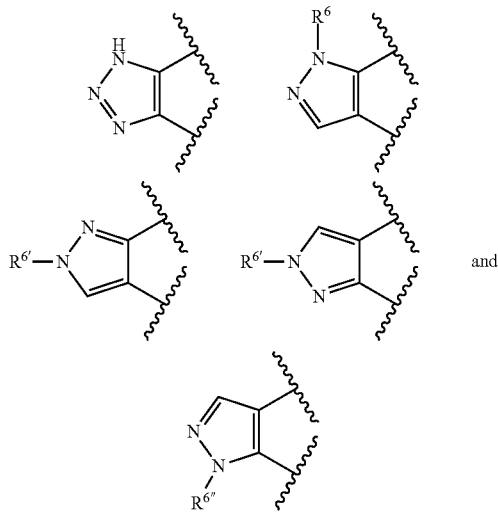

wherein R⁶ is lower alkyl, more specifically methyl; R⁶' is lower alkyl, more specifically methyl; R⁶'' is lower alkyl or lower alkenyl, more specifically methyl, ethyl or allyl.

A particular embodiment of the present invention provides compounds of formula (Ia) as described above, wherein R¹ is selected from the group consisting of:

wherein R⁴ is hydrogen, hydroxyl, halogen, lower alkoxy, lower haloalkoxy, —OC(O)-lower alkyl, —OCH₂C(O)-lower alkoxy or phenyl, and R⁵ is halogen. More specifically, R⁴ is hydrogen, hydroxyl, chloro, fluoro, bromo, methoxy, fluoromethoxy, trifluoromethoxy, 2-fluoroethoxy, —OC(O)CH₃, —OCH₂C(O)OCH₃ or phenyl, and R⁵ is chloro. Further more specifically, R¹ is phenyl, 3-chloro-phenyl, 3-fluorophenyl, 3-bromophenyl, 4-fluoro-phenyl, 3-methoxy-phenyl, 3-trifluoromethoxy-phenyl, 5-chloro-thiophen-2-yl, 3-(fluoromethoxy)phenyl, 3-hydroxy-phenyl, 3-(2-fluoroethoxy)phenyl, 3-acetoxyphenyl, 3-acetoxymethoxyphenyl, or biphenyl-3-yl.

Another embodiment of the present invention provides compounds of formula (Ia) as described above, wherein R³ and R³' are each independently hydrogen, methyl, cyclopropylmethyl, cyanomethyl, oxazol-2-ylmethyl, oxazol-4-ylmethyl, isoxazol-5-ylmethyl, 3-methylisoxazol-5-ylmethyl, 5-methylisoxazol-3-ylmethyl, 3-ethylisoxazol-5-ylmethyl, 2-cyclopropyl-5-methyloxazol-4-ylmethyl, 3-isopropyl-1,2,4-oxadiazol-5-ylmethyl, 5-cyclopropyl-1,2,4-oxadiazol-3-ylmethyl, 3-cyclopropyl-1,2,4-oxadiazol-5-ylmethyl, 5-methyl-1,2,4-oxadiazol-3-ylmethyl, 1H-pyrazol-5-ylmethyl, 1,3-dimethyl-4-nitro-1H-pyrazol-5-ylmethyl, 5-methyl-1H-pyrazol-3-ylmethyl, 1-methyl-1H-pyrazol-3-ylmethyl, 4-chloro-1-methyl-1H-pyrazol-3-ylmethyl, 1-propyl-1H-pyrazol-3-ylmethyl, 5-cyclopropyl-1H-pyrazol-3-ylmethyl, 2-methylthiazol-4-ylmethyl, 5-methylthiazol-2-ylmethyl, 4-cyanothiazol-2-ylmethyl, 1H-tetrazol-5-ylmethyl, pyridin-2-ylmethyl, pyridin-4-ylmethyl, 5-bromopyridin-2-ylmethyl, 6-chloropyridin-3-ylmethyl, 5-methylpyridin-2-ylmethyl, 6-(trifluoromethyl)pyridin-3-ylmethyl, 2-methoxypyridin-3-ylmethyl, 6-cyanopyridin-3-ylmethyl, imidazo[1,2-a]pyridin-2-ylmethyl, imidazo[2,1-b]thiazol-6-ylmethyl, benzo[d]oxazol-2-ylmethyl, ethyl, 2-hydroxyethyl, 2-cyano-ethyl, 2-hydroxy-1-methyl-ethyl, 2-fluoroethyl, 2,2-difluoroethyl, 2,2,2-trifluoro-ethyl, 2-methoxyethyl, 2-(2-fluoroethoxy)ethyl, 1-(pyridin-3-yl)ethyl, propyl, isopropyl, 3-hydroxy-propyl, 2-hydroxy-propyl, 3,3,3-trifluoropropyl, 2-hydroxy-2-methyl-propyl, isobutyl, tert-butyl, 3-methoxy-propyl, cyclopropyl, 1-cyanocyclopropyl, cyclobutyl, oxetan-3-yl, 3-methyloxetan-3-yl, tetrahydro-furan-3-yl, phenyl or benzyl, or R³ and R³', together with the nitrogen atom to which they are attached, form azetidine ring, 3-fluoroazetidine ring, 3,3-difluoro-azetidine ring, 3-hydroxy-azetidine ring, pyrrolidine ring, 2-methylpyrrolidine ring, 2,5-dihydro-1H-pyrrole ring, piperidine ring, morpholine ring, 1,1-dioxo-1λ6-thiomorpholine ring, 3-(pyridin-3-yl)morpholine ring, 2-methyl-2,4,5,6-tetrahydropyrrolo[3,4-c]pyrazole ring, or 2-oxa-6-azaspiro[3.3]heptane ring.

Particular compounds of formula (Ia) are those selected from the group consisting of:
5-(Azetidine-1-carbonyl)-1H-[1,2,3]triazole-4-carboxylic acid (2-phenyl-imidazo[1,2-a]pyrimidin-7-yl)-amide,
1H-[1,2,3]Triazole-4,5-dicarboxylic acid 5-(ethyl-methyl-amide) 4-[(2-phenyl-imidazo[1,2-a]pyrimidin-7-yl)-amide],
4-(Azetidine-1-carbonyl)-2-methyl-2H-pyrazole-3-carboxylic acid (2-phenyl-imidazo[1,2-a]pyrimidin-7-yl)-amide,
2-Methyl-4-(morpholine-4-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-methylamide 3-[(2-phenyl-imidazo[1,2-a]pyrimidin-7-yl)-amide],
2-Methyl-2H-pyrazole-3,4-dicarboxylic acid 3-{[2-(3-chloro-phenyl)-imidazo[1,2-a]pyrimidin-7-yl]-amide}-4-methylamide,
2-Methyl-2H-pyrazole-3,4-dicarboxylic acid 3-{[2-(4-fluoro-phenyl)-imidazo[1,2-a]pyrimidin-7-yl]-amide}-4-methylamide, 4-(3,3-Difluoro-azetidine-1-carbonyl)-2-methyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-hydroxy-ethyl)-amide]3-[(2-phenyl-imidazo[1,2-a]pyrimidin-7-yl)-amide],
4-(3-Hydroxy-azetidine-1-carbonyl)-2-methyl-2H-pyrazole-3-carboxylic acid (2-phenyl-imidazo[1,2-a]pyrimidin-7-yl)-amide,
4-(1,1-Dioxo-1λ6-thiomorpholine-4-carbonyl)-2-methyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(3-hydroxy-propyl)-amide]3-[(2-phenyl-imidazo[1,2-a]pyrimidin-7-yl)-amide],
2-Methyl-2H-pyrazole-3,4-dicarboxylic acid 4-[(3-methoxy-propyl)-amide]3-[(2-phenyl-imidazo[1,2-a]pyrimidin-7-yl)-amide],
2-Methyl-2H-pyrazole-3,4-dicarboxylic acid 3-[(2-phenyl-imidazo[1,2-a]pyrimidin-7-yl)-amide]-4-[(tetrahydro-furan-3-yl)-amide],
2-Methyl-2H-pyrazole-3,4-dicarboxylic acid 4-[(2-hydroxy-1-methyl-ethyl)-amide]3-[(2-phenyl-imidazo[1,2-a]pyrimidin-7-yl)-amide],
2-Methyl-2H-pyrazole-3,4-dicarboxylic acid 4-[(2-hydroxy-propyl)-amide]3-[(2-phenyl-imidazo[1,2-a]pyrimidin-7-yl)-amide],
4-(Azetidine-1-carbonyl)-2-methyl-2H-pyrazole-3-carboxylic acid [2-(3-methoxy-phenyl)-imidazo[1,2-a]pyrimidin-7-yl]-amide,
2-Methyl-2H-pyrazole-3,4-dicarboxylic acid 4-[(2-methoxy-ethyl)-amide]3-[(2-phenyl-imidazo[1,2-a]pyrimidin-7-yl)-amide],
2-Methyl-2H-pyrazole-3,4-dicarboxylic acid 4-diethylamide 3-[(2-phenyl-imidazo[1,2-a]pyrimidin-7-yl)-amide],
2-Methyl-4-(pyrrolidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-(ethyl-methyl-amide) 3-[(2-phenyl-imidazo[1,2-a]pyrimidin-7-yl)-amide],
2-Methyl-2H-pyrazole-3,4-dicarboxylic acid 4-ethylamide 3-[(2-phenyl-imidazo[1,2-a]pyrimidin-7-yl)-amide],
2-Methyl-2H-pyrazole-3,4-dicarboxylic acid 4-cyclopropylamide 3-[(2-phenyl-imidazo[1,2-a]pyrimidin-7-yl)-amide],
2-Methyl-4-(piperidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-hydroxy-ethyl)-methyl-amide]3-[(2-phenyl-imidazo[1,2-a]pyrimidin-7-yl)-amide],
2-Methyl-2H-pyrazole-3,4-dicarboxylic acid 4-(isopropyl-methyl-amide) 3-[(2-phenyl-imidazo[1,2-a]pyrimidin-7-yl)-amide],
2-Methyl-2H-pyrazole-3,4-dicarboxylic acid 4-[(2-methoxy-ethyl)-methyl-amide]3-[(2-phenyl-imidazo[1,2-a]pyrimidin-7-yl)-amide],
2-Methyl-2H-pyrazole-3,4-dicarboxylic acid 4-(methyl-propyl-amide) 3-[(2-phenyl-imidazo[1,2-a]pyrimidin-7-yl)-amide],
2-Methyl-2H-pyrazole-3,4-dicarboxylic acid 3-[(2-phenyl-imidazo[1,2-a]pyrimidin-7-yl)-amide]-4-propylamide,
2-Methyl-2H-pyrazole-3,4-dicarboxylic acid 4-cyclopropylmethyl-amide 3-[(2-phenyl-imidazo[1,2-a]pyrimidin-7-yl)-amide],
2-Methyl-2H-pyrazole-3,4-dicarboxylic acid 4-cyclobutylamide 3-[(2-phenyl-imidazo[1,2-a]pyrimidin-7-yl)-amide],
2-Methyl-2H-pyrazole-3,4-dicarboxylic acid 4-isopropylamide 3-[(2-phenyl-imidazo[1,2-a]pyrimidin-7-yl)-amide],
4-(Azetidine-1-carbonyl)-2-methyl-2H-pyrazole-3-carboxylic acid [2-(3-trifluoromethoxy-phenyl)-imidazo[1,2-a]pyrimidin-7-yl]-amide,
4-(Azetidine-1-carbonyl)-2-methyl-2H-pyrazole-3-carboxylic acid [2-(3-chloro-phenyl)-imidazo[1,2-a]pyrimidin-7-yl]-amide,
2-Ethyl-2H-pyrazole-3,4-dicarboxylic acid 4-methylamide 3-[(2-phenyl-imidazo[1,2-a]pyrimidin-7-yl)-amide],
1H-[1,2,3]Triazole-4,5-dicarboxylic acid 5-methylamide 4-[(2-phenyl-imidazo[1,2-a]pyrimidin-7-yl)-amide],
3-(Azetidine-1-carbonyl)-1-methyl-1H-pyrazole-4-carboxylic acid (2-phenyl-imidazo[1,2-a]pyrimidin-7-yl)-amide,
1-Methyl-1H-pyrazole-3,4-dicarboxylic acid 3-(ethyl-methyl-amide) 4-[(2-phenyl-imidazo[1,2-a]pyrimidin-7-yl)-amide],
1-Methyl-1H-pyrazole-3,4-dicarboxylic acid 4-(ethyl-methyl-amide) 3-[(2-phenyl-imidazo[1,2-a]pyrimidin-7-yl)-amide],
4-(Azetidine-1-carbonyl)-2-ethyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-cyano-ethyl)-methyl-amide]3-[(2-phenyl-imidazo[1,2-a]pyrimidin-7-yl)-amide],
2-Methyl-2H-pyrazole-3,4-dicarboxylic acid 4-(isobutyl-methyl-amide) 3-[(2-phenyl-imidazo[1,2-a]pyrimidin-7-yl)-amide],
2-Methyl-2H-pyrazole-3,4-dicarboxylic acid 4-[(2-hydroxy-2-methyl-propyl)-amide]3-[(2-phenyl-imidazo[1,2-a]pyrimidin-7-yl)-amide],
2-Ethyl-2H-pyrazole-3,4-dicarboxylic acid 4-(ethyl-methyl-amide) 3-[(2-phenyl-imidazo[1,2-a]pyrimidin-7-yl)-amide],
4-(Azetidine-1-carbonyl)-2-methyl-2H-pyrazole-3-carboxylic acid [2-(5-chloro-thiophen-2-yl)-imidazo[1,2-a]pyrimidin-7-yl]-amide,
2-Methyl-2H-pyrazole-3,4-dicarboxylic acid 4-dimethylamide 3-[(2-phenyl-imidazo[1,2-a]pyrimidin-7-yl)-amide],
4-(azetidine-1-carbonyl)-N-(2-(3-(fluoromethoxy)phenyl)imidazo[1,2-a]pyrimidin-7-yl)-1-methyl-1H-pyrazole-5-carboxamide,
4-(Azetidine-1-carbonyl)-2-methyl-2H-pyrazole-3-carboxylic acid [2-(3-hydroxy-phenyl)-imidazo[1,2-a]pyrimidin-7-yl]-amide,
N5-(2-(3-hydroxyphenyl)imidazo[1,2-a]pyrimidin-7-yl)-N4,N4,1-trimethyl-1H-pyrazole-4,5-dicarboxamide,
2-Methyl-2H-pyrazole-3,4-dicarboxylic acid 4-dimethylamide 3-{[2-(3-methoxy-phenyl)-imidazo[1,2-a]pyrimidin-7-yl]-amide},
N4-ethyl-N5-(2-(3-(fluoromethoxy)phenyl)imidazo[1,2-a]pyrimidin-7-yl)-N4,1-dimethyl-1H-pyrazole-4,5-dicarboxamide,
N4-ethyl-N5-(2-(3-methoxyphenyl)imidazo[1,2-a]pyrimidin-7-yl)-N4,1-dimethyl-1H-pyrazole-4,5-dicarboxamide,
N5-(2-(3-(fluoromethoxy)phenyl)imidazo[1,2-a]pyrimidin-7-yl)-N4,N4,1-trimethyl-1H-pyrazole-4,5-dicarboxamide, N4-ethyl-N5-(2-(3-(2-fluoroethoxy)phenyl)imidazo[1,2-a]pyrimidin-7-yl)-N4,1-dimethyl-1H-pyrazole-4,5-dicarboxamide, 4-(3-fluoroazetidine-1-carbonyl)-N-(2-(3-(2-fluoroethoxy)phenyl)imidazo[1,2-a]pyrimidin-7-yl)-1-methyl-1H-pyrazole-5-carboxamide, 4-(azetidine-1-carbonyl)-N-(2-(3-fluorophenyl)imidazo[1,2-a]pyrimidin-7-yl)-1-methyl-1H-pyrazole-5-carboxamide, 4-(3-fluoroazetidine-1-carbonyl)-N-(2-(3-fluorophenyl)imidazo[1,2-a]pyrimidin-7-yl)-1-methyl-1H-pyrazole-5-carboxamide, 3-(7-(4-(dimethylcarbamoyl)-1-methyl-1H-pyrazole-5-carboxamido)imidazo[1,2-a]pyrimidin-2-yl)phenyl acetate, N5-(2-(3-fluorophenyl)imidazo[1,2-a]pyrimidin-7-yl)-N4,N4,1-trimethyl-1H-pyrazole-4,5-dicarboxamide, N4-(2-fluoroethyl)-N4,1-dimethyl-N5-(2-phenylimidazo[1,2-a]pyrimidin-7-yl)-1H-pyrazole-4,5-dicarboxamide, 2-Methyl-2H-pyrazole-3,4-dicarboxylic acid 3-({2-[3-(2-fluoro-ethoxy)-phenyl]-imidazo[1,2-a]pyrimidin-7-yl}-amide) 4-[(2-methoxy-ethyl)-methyl-amide], N4-ethyl-N5-(2-(3-fluorophenyl)imidazo[1,2-a]pyrimidin-7-yl)-N4,1-dimethyl-1H-pyrazole-4,5-dicarboxamide, 4-(3-fluoroazetidine-1-carbonyl)-N-(2-(3-methoxyphenyl)imidazo[1,2-a]pyrimidin-7-yl)-1-methyl-1H-pyrazole-5-carboxamide, 2-Methyl-2H-pyrazole-3,4-dicarboxylic acid 3-{[2-(3-fluoromethoxy-phenyl)-imidazo[1,2-a]pyrimidin-7-yl]-amide}-4-[(2-methoxy-ethyl)-methyl-amide], methyl 2-(3-(7-(4-(ethyl(methyl)carbamoyl)-1-methyl-1H-pyrazole-5-carboxamido)imidazo[1,2-a]pyrimidin-2-yl)phenoxy)acetate, 2-Methyl-2H-pyrazole-3,4-dicarboxylic acid 4-[(2-methoxy-ethyl)-methyl-amide]3-{[2-(3-methoxy-phenyl)-imidazo[1,2-a]pyrimidin-7-yl]-amide}, 2-Methyl-2H-pyrazole-3,4-dicarboxylic acid 4-dimethylamide 3-({2-[3-(2-fluoro-ethoxy)-phenyl]-imidazo[1,2-a]pyrimidin-7-yl}-amide), 4-(Azetidine-1-carbonyl)-2-methyl-2H-pyrazole-3-carboxylic acid {2-[3-(2-fluoro-ethoxy)-phenyl]-imidazo[1,2-a]pyrimidin-7-yl}-amide, N4-(2-fluoroethyl)-N5-(2-(3-fluorophenyl)imidazo[1,2-a]pyrimidin-7-yl)-N4,1-dimethyl-1H-pyrazole-4,5-dicarboxamide, 3-(7-(4-(azetidine-1-carbonyl)-1-methyl-1H-pyrazole-5-carboxamido)imidazo[1,2-a]pyrimidin-2-yl)phenyl acetate, N4-(2-(2-fluoroethoxy)ethyl)-N4,1-dimethyl-N5-(2-phenylimidazo[1,2-a]pyrimidin-7-yl)-1H-pyrazole-4,5-dicarboxamide, 2-Methyl-2H-pyrazole-3,4-dicarboxylic acid 3-{[2-(3-fluoro-phenyl)-imidazo[1,2-a]pyrimidin-7-yl]-amide}-4-[(2-methoxy-ethyl)-methyl-amide], N4-(2-fluoroethyl)-N5-(2-(3-(fluoromethoxy)phenyl)imidazo[1,2-a]pyrimidin-7-yl)-N4,1-dimethyl-1H-pyrazole-4,5-dicarboxamide, N4-(2-(2-fluoroethoxy)ethyl)-N5-(2-(3-(2-fluoroethoxy)phenyl)imidazo[1,2-a]pyrimidin-7-yl)-N4,1-dimethyl-1H-pyrazole-4,5-dicarboxamide, N4-(2-(2-fluoroethoxy)ethyl)-N5-(2-(3-methoxyphenyl)imidazo[1,2-a]pyrimidin-7-yl)-N4,1-dimethyl-1H-pyrazole-4,5-dicarboxamide, N4-(2-fluoroethyl)-N5-(2-(3-methoxyphenyl)imidazo[1,2-a]pyrimidin-7-yl)-N4,1-dimethyl-1H-pyrazole-4,5-dicarboxamide, 1-methyl-N4-(oxazol-4-ylmethyl)-N5-(2-phenylimidazo[1,2-a]pyrimidin-7-yl)-1H-pyrazole-4,5-dicarboxamide, N4-((1H-pyrazol-5-yl)methyl)-1-methyl-N5-(2-phenylimidazo[1,2-a]pyrimidin-7-yl)-1H-pyrazole-4,5-dicarboxamide, 4-(2,5-dihydro-1H-pyrrole-1-carbonyl)-1-methyl-N-(2-phenylimidazo[1,2-a]pyrimidin-7-yl)-1H-pyrazole-5-carboxamide, 4-(3-fluoroazetidine-1-carbonyl)-1-methyl-N-(2-phenylimidazo[1,2-a]pyrimidin-7-yl)-1H-pyrazole-5-carboxamide, 1-methyl-4-(2-methylpyrrolidine-1-carbonyl)-N-(2-phenylimidazo[1,2-a]pyrimidin-7-yl)-1H-pyrazole-5-carboxamide, 4-(azetidine-1-carbonyl)-N-(2-(3-bromophenyl)imidazo[1,2-a]pyrimidin-7-yl)-1-methyl-1H-pyrazole-5-carboxamide, 1-methyl-N5-(2-phenylimidazo[1,2-a]pyrimidin-7-yl)-N4-(pyridin-2-ylmethyl)-1H-pyrazole-4,5-dicarboxamide, N4-(cyanomethyl)-N4,1-dimethyl-N5-(2-phenylimidazo[1,2-a]pyrimidin-7-yl)-1H-pyrazole-4,5-dicarboxamide, 1-allyl-4-(azetidine-1-carbonyl)-N-(2-phenylimidazo[1,2-a]pyrimidin-7-yl)-1H-pyrazole-5-carboxamide, 1-methyl-N4-((5-methyl-1H-pyrazol-3-yl)methyl)-N5-(2-phenylimidazo[1,2-a]pyrimidin-7-yl)-1H-pyrazole-4,5-dicarboxamide, 1-methyl-N4-(oxazol-2-ylmethyl)-N5-(2-phenylimidazo[1,2-a]pyrimidin-7-yl)-1H-pyrazole-4,5-dicarboxamide, N4-(2-fluoroethyl)-1-methyl-N5-(2-phenylimidazo[1,2-a]pyrimidin-7-yl)-1H-pyrazole-4,5-dicarboxamide, 1-methyl-N-4-((5-methylthiazol-2-yl)methyl)-N5-(2-phenylimidazo[1,2-a]pyrimidin-7-yl)-1H-pyrazole-4,5-dicarboxamide, N4-(cyanomethyl)-1-methyl-N5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N4-(3,3,3-trifluoropropyl)-1H-pyrazole-4,5-dicarboxamide, 1-methyl-N4-((3-methylisoxazol-5-yl)methyl)-N5-(2-phenylimidazo[1,2-a]pyrimidin-7-yl)-1H-pyrazole-4,5-dicarboxamide, 4-(azetidine-1-carbonyl)-N-(2-(biphenyl-3-yl)imidazo[1,2-a]pyrimidin-7-yl)-1-methyl-1H-pyrazole-5-carboxamide, N4-(2,2-difluoroethyl)-1-methyl-N5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N4-(2,2,2-trifluoroethyl)-1H-pyrazole-4,5-dicarboxamide, N4-(isoxazol-5-ylmethyl)-1-methyl-N5-(2-phenylimidazo[1,2-a]pyrimidin-7-yl)-1H-pyrazole-4,5-dicarboxamide, 1-methyl-N-(2-phenylimidazo[1,2-a]pyrimidin-7-yl)-4-(2-oxa-6-azaspiro[3.3]heptane-6-carbonyl)-1H-pyrazole-5-carboxamide, 1-methyl-N4-phenyl-N5-(2-phenylimidazo[1,2-a]pyrimidin-7-yl)-1H-pyrazole-4,5-dicarboxamide, 1-methyl-N4-(3-methyloxetan-3-yl)-N5-(2-phenylimidazo[1,2-a]pyrimidin-7-yl)-1H-pyrazole-4,5-dicarboxamide, N4,1-dimethyl-N5-(2-phenylimidazo[1,2-a]pyrimidin-7-yl)-N4-(pyridin-2-ylmethyl)-1H-pyrazole-4,5-dicarboxamide, N4-((5-bromopyridin-2-yl)methyl)-N4,1-dimethyl-N5-(2-phenylimidazo[1,2-a]pyrimidin-7-yl)-1 H-pyrazole-4,5-dicarboxamide, 1-methyl-N-(2-phenylimidazo[1,2-a]pyrimidin-7-yl)-4-(3-(pyridin-3-yl)morpholine-4-carbonyl)-1H-pyrazole-5-carboxamide, N4-tert-butyl-1-methyl-N5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N4-(1-(pyridin-3-yl)ethyl)-1H-pyrazole-4,5-dicarboxamide, N4-((1,3-dimethyl-4-nitro-1H-pyrazol-5-yl)methyl)-1-methyl-N5-(2-phenylimidazo[1,2-a]pyrimidin-7-yl)-1H-pyrazole-4,5-dicarboxamide,
N5-(oxetan-3-yl)-N4-(2-phenylimidazo[1,2-a]pyrimidin-7-yl)-1H-1,2,3-triazole-4,5-dicarboxamide,
N4-((6-cyanopyridin-3-yl)methyl)-1-methyl-N5-(2-phenylimidazo[1,2-a]pyrimidin-7-yl)-1H-pyrazole-4,5-dicarboxamide,
1-methyl-N-4-((5-methylisoxazol-3-yl)methyl)-N5-(2-phenylimidazo[1,2-a]pyrimidin-7-yl)-1H-pyrazole-4,5-dicarboxamide,
1-methyl-N5-(2-phenylimidazo[1,2-a]pyrimidin-7-yl)-N446-(trifluoromethyl)pyridin-3-yl)methyl)-1H-pyrazole-4,5-dicarboxamide,
N4-(1-cyanocyclopropyl)-1-methyl-N5-(2-phenylimidazo[1,2-a]pyrimidin-7-yl)-1H-pyrazole-4,5-dicarboxamide,
N5-(5-(methoxymethyl)-2-phenylimidazo[1,2-a]pyrimidin-7-yl)-N4,1-dimethyl-1H-pyrazole-4,5-dicarboxamide,
N4-((1H-tetrazol-5-yl)methyl)-1-methyl-N5-(2-phenylimidazo[1,2-a]pyrimidin-7-yl)-1H-pyrazole-4,5-dicarboxamide,
1-methyl-N5-(2-phenylimidazo[1,2-a]pyrimidin-7-yl)-N4-(pyridin-4-ylmethyl)-1H-pyrazole-4,5-dicarboxamide,
N4-(imidazo[1,2-a]pyridin-2-ylmethyl)-1-methyl-N5-(2-phenylimidazo[1,2-a]pyrimidin-7-yl)-1H-pyrazole-4,5-dicarboxamide,
N5-(2-methoxyethyl)-N4-(2-phenylimidazo[1,2-a]pyrimidin-7-yl)-1H-1,2,3-triazole-4,5-dicarboxamide,
N4-((4-cyanothiazol-2-yl)methyl)-1-methyl-N5-(2-phenylimidazo[1,2-a]pyrimidin-7-yl)-1H-pyrazole-4,5-dicarboxamide,
N4-((5-cyclopropyl-1H-pyrazol-3-yl)methyl)-1-methyl-N5-(2-phenylimidazo[1,2-a]pyrimidin-7-yl)-1H-pyrazole-4,5-dicarboxamide,
N4-(imidazo[2,1-b]thiazol-6-ylmethyl)-1-methyl-N5-(2-phenylimidazo[1,2-a]pyrimidin-7-yl)-1H-pyrazole-4,5-dicarboxamide,
N4-((6-chloropyridin-3-yl)methyl)-1-methyl-N5-(2-phenylimidazo[1,2-a]pyrimidin-7-yl)-1H-pyrazole-4,5-dicarboxamide,
1-methyl-N-4-((5-methylpyridin-2-yl)methyl)-N5-(2-phenylimidazo[1,2-a]pyrimidin-7-yl)-1H-pyrazole-4,5-dicarboxamide,
N4-(2-phenylimidazo[1,2-a]pyrimidin-7-yl)-N5-propyl-1H-1,2,3-triazole-4,5-dicarboxamide,
1-methyl-N4-((1-methyl-1H-pyrazol-3-yl)methyl)-N5-(2-phenylimidazo[1,2-a]pyrimidin-7-yl)-1H-pyrazole-4,5-dicarboxamide,
N4-((4-chloro-1-methyl-1H-pyrazol-3-yl)methyl)-1-methyl-N5-(2-phenylimidazo[1,2-a]pyrimidin-7-yl)-1H-pyrazole-4,5-dicarboxamide,
N5-cyclopropyl-N4-(2-phenylimidazo[1,2-a]pyrimidin-7-yl)-1H-1,2,3-triazole-4,5-dicarboxamide,
N4-((3-ethylisoxazol-5-yl)methyl)-1-methyl-N5-(2-phenylimidazo[1,2-a]pyrimidin-7-yl)-1H-pyrazole-4,5-dicarboxamide,
N4-((2-methoxypyridin-3-yl)methyl)-1-methyl-N5-(2-phenylimidazo[1,2-a]pyrimidin-7-yl)-1H-pyrazole-4,5-dicarboxamide,
N4-benzyl-1-methyl-N5-(2-phenylimidazo[1,2-a]pyrimidin-7-yl)-1H-pyrazole-4,5-dicarboxamide,
1-methyl-N-4-((2-methylthiazol-4-yl)methyl)-N5-(2-phenylimidazo[1,2-a]pyrimidin-7-yl)-1H-pyrazole-4,5-dicarboxamide,
1-methyl-N5-(2-phenylimidazo[1,2-a]pyrimidin-7-yl)-N4-((1-propyl-1H-pyrazol-3-yl)methyl)-1 H-pyrazole-4,5-dicarboxamide,
N4-((2-cyclopropyl-5-methyloxazol-4-yl)methyl)-1-methyl-N5-(2-phenylimidazo[1,2-a]pyrimidin-7-yl)-1H-pyrazole-4,5-dicarboxamide,
N4-((5-cyclopropyl-1,2,4-oxadiazol-3-yl)methyl)-1-methyl-N5-(2-phenylimidazo[1,2-a]pyrimidin-7-yl)-1H-pyrazole-4,5-dicarboxamide,
N4-((3-cyclopropyl-1,2,4-oxadiazol-5-yl)methyl)-1-methyl-N5-(2-phenylimidazo[1,2-a]pyrimidin-7-yl)-1H-pyrazole-4,5-dicarboxamide,
1-methyl-N4-((5-methyl-1,2,4-oxadiazol-3-yl)methyl)-N5-(2-phenylimidazo[1,2-a]pyrimidin-7-yl)-1H-pyrazole-4,5-dicarboxamide,
1-methyl-4-(2-methyl-2,4,5,6-tetrahydropyrrolo[3,4-c]pyrazole-5-carbonyl)-N-(2-phenylimidazo[1,2-a]pyrimidin-7-yl)-1H-pyrazole-5-carboxamide,
N4-(benzo[d]oxazol-2-ylmethyl)-1-methyl-N5-(2-phenylimidazo[1,2-a]pyrimidin-7-yl)-1H-pyrazole-4,5-dicarboxamide, and
N4-((3-isopropyl-1,2,4-oxadiazol-5-yl)methyl)-1-methyl-N5-(2-phenylimidazo[1,2-a]pyrimidin-7-yl)-1H-pyrazole-4,5-dicarboxamide, or pharmaceutically acceptable salts thereof.

Another embodiment of the present invention provides compounds of formula (Ia) as described above, wherein $R^1$ is phenyl or thienyl, wherein said phenyl and said thienyl are optionally substituted by halogen or lower alkoxy; $R^3$ and $R^{3'}$ are each independently lower alkyl or lower alkoxy lower alkyl, or $R^3$ and $R^{3'}$, together with the nitrogen atom to which they are attached, form an azetidine ring, pyrrolidine ring or piperidine ring, wherein said azetizine ring is optionally substituted by 1 or 2 substituents independently selected from the group consisting of hydroxyl and halogen.

Particular compounds of formula (Ia) are those selected from the group consisting of:
4-(Azetidine-1-carbonyl)-2-methyl-2H-pyrazole-3-carboxylic acid (2-phenyl-imidazo[1,2-a]pyrimidin-7-yl)-amide,
2-Methyl-4-(morpholine-4-carbonyl)-2H-pyrazole-3-carboxylic acid (2-phenyl-imidazo[1,2-a]pyrimidin-7-yl)-amide,
4-(3,3-Difluoro-azetidine-1-carbonyl)-2-methyl-2H-pyrazole-3-carboxylic acid (2-phenyl-imidazo[1,2-a]pyrimidin-7-yl)-amide,
4-(3-Hydroxy-azetidine-1-carbonyl)-2-methyl-2H-pyrazole-3-carboxylic acid (2-phenyl-imidazo[1,2-a]pyrimidin-7-yl)-amide,
4-(Azetidine-1-carbonyl)-2-methyl-2H-pyrazole-3-carboxylic acid [2-(3-methoxy-phenyl)-imidazo[1,2-a]pyrimidin-7-yl]-amide,
2-Methyl-4-(pyrrolidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-(ethyl-methyl-amide) 3-[(2-phenyl-imidazo[1,2-a]pyrimidin-7-yl)-amide],
2-Methyl-4-(piperidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-methoxy-ethyl)-methyl-amide]3-[(2-phenyl-imidazo[1,2-a]pyrimidin-7-yl)-amide],
4-(Azetidine-1-carbonyl)-2-methyl-2H-pyrazole-3-carboxylic acid [2-(3-chloro-phenyl)-imidazo[1,2-a]pyrimidin-7-yl]-amide,
4-(Azetidine-1-carbonyl)-2-ethyl-2H-pyrazole-3-carboxylic acid (2-phenyl-imidazo[1,2-a]pyrimidin-7-yl)-amide, 2-Ethyl-2H-pyrazole-3,4-dicarboxylic acid 4-(ethyl-methyl-amide) 3-[(2-phenyl-imidazo[1,2-a]pyrimidin-7-yl)-amide],
4-(Azetidine-1-carbonyl)-2-methyl-2H-pyrazole-3-carboxylic acid [2-(5-chloro-thiophen-2-yl)-imidazo[1,2-a]pyrimidin-7-yl]-amide, and
2-Methyl-2H-pyrazole-3,4-dicarboxylic acid 4-dimethylamide 3-[(2-phenyl-imidazo[1,2-a]pyrimidin-7-yl)-amide],
or pharmaceutically acceptable salts thereof.

Another embodiment of the present invention provides compounds of formula (I) or pharmaceutically acceptable salts thereof as described above, wherein R² is

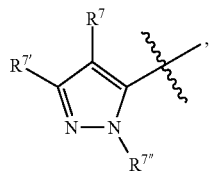

wherein
R⁷ is hydrogen, halogen, lower alkoxy-C(O)— or heteroaryl, more specifically hydrogen, bromo, chloro, ethoxycarbonyl or isoxazol-5-yl;
R⁷' is hydrogen, lower alkyl or nitro, more specifically hydrogen, methyl or nitro; and
R⁷" is lower alkyl, cycloalkyl or aryl, more specifically methyl, ethyl, propyl, isopropyl, butyl, sec-butyl, isobutyl, cyclopentyl or phenyl.

Particular compounds of formula (I) are those selected from the group consisting of:
4-Chloro-2-methyl-2H-pyrazole-3-carboxylic acid (2-phenyl-imidazo[1,2-a]pyrimidin-7-yl)-amide,
4-Chloro-2,5-dimethyl-2H-pyrazole-3-carboxylic acid (2-phenyl-imidazo[1,2-a]pyrimidin-7-yl)-amide,
2-Phenyl-2H-pyrazole-3-carboxylic acid (2-phenyl-imidazo[1,2-a]pyrimidin-7-yl)-amide,
4-Bromo-2,5-dimethyl-2H-pyrazole-3-carboxylic acid (2-phenyl-imidazo[1,2-a]pyrimidin-7-yl)-amide,
4-Bromo-2-methyl-2H-pyrazole-3-carboxylic acid (2-phenyl-imidazo[1,2-a]pyrimidin-7-yl)-amide,
4-Chloro-2-ethyl-2H-pyrazole-3-carboxylic acid (2-phenyl-imidazo[1,2-a]pyrimidin-7-yl)-amide,
4-Chloro-2-propyl-2H-pyrazole-3-carboxylic acid (2-phenyl-imidazo[1,2-a]pyrimidin-7-yl)-amide,
2-Butyl-4-chloro-2H-pyrazole-3-carboxylic acid (2-phenyl-imidazo[1,2-a]pyrimidin-7-yl)-amide,
4-Chloro-2-isopropyl-2H-pyrazole-3-carboxylic acid (2-phenyl-imidazo[1,2-a]pyrimidin-7-yl)-amide,
2-sec-Butyl-4-chloro-2H-pyrazole-3-carboxylic acid (2-phenyl-imidazo[1,2-a]pyrimidin-7-yl)-amide,
4-Chloro-2-isobutyl-2H-pyrazole-3-carboxylic acid (2-phenyl-imidazo[1,2-a]pyrimidin-7-yl)-amide,
2-Isobutyl-5-nitro-2H-pyrazole-3-carboxylic acid (2-phenyl-imidazo[1,2-a]pyrimidin-7-yl)-amide,
2-Cyclopentyl-5-nitro-2H-pyrazole-3-carboxylic acid (2-phenyl-imidazo[1,2-a]pyrimidin-7-yl)-amide,
2-Ethyl-5-nitro-2H-pyrazole-3-carboxylic acid (2-phenyl-imidazo[1,2-a]pyrimidin-7-yl)-amide,
2-Isopropyl-5-nitro-2H-pyrazole-3-carboxylic acid (2-phenyl-imidazo[1,2-a]pyrimidin-7-yl)-amide,
4-Isoxazol-5-yl-2-methyl-2H-pyrazole-3-carboxylic acid (2-phenyl-imidazo[1,2-a]pyrimidin-7-yl)-amide, and 1-Ethyl-5-(2-phenyl-imidazo[1,2-a]pyrimidin-7-ylcarbamoyl)-1H-pyrazole-4-carboxylic acid ethyl ester, or pharmaceutically acceptable salts thereof.

Yet particular compounds of formula (I) are those selected from the group consisting of:
Isoxazole-5-carboxylic acid (2-phenyl-imidazo[1,2-a]pyrimidin-7-yl)-amide,
4,5,6,7-Tetrahydro-benzo[d] isoxazole-3-carboxylic acid (2-phenyl-imidazo[1,2-a]pyrimidin-7-yl)-amide,
5-(2-Phenyl-imidazo[1,2-a]pyrimidin-7-ylcarbamoyl)-3H-[1,2,3]triazole-4-carboxylic acid methyl ester, and
1-Methyl-3-(pyrimidin-5-ylamino)-1H-pyrazole-4-carboxylic acid (2-phenyl-imidazo[1,2-a]pyrimidin-7-yl)-amide,
or pharmaceutically acceptable salts thereof.

Another embodiment of the present invention provides compounds of formula (I) or pharmaceutically acceptable salts thereof as described above, wherein R² is 6-membered heteroaryl selected from the group consisting of:

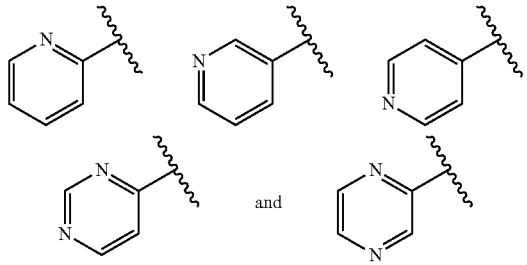

wherein said heteroaryl is substituted by 1 to 3 substituents independently selected from the group consisting of bromo, chloro, methyl, methoxy, cyclopropyl, —C(O)NHCH₂CF₃,

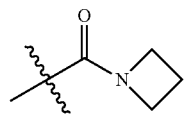 [SMILES: *C(=O)N1CCC1]

and pyrimidin-5-ylamino.

Particular compounds of formula (I) are those selected from the group consisting of:
3,6-Dimethyl-pyridine-2-carboxylic acid (2-phenyl-imidazo[1,2-a]pyrimidin-7-yl)-amide,
2-Chloro-N-(2-phenyl-imidazo[1,2-a]pyrimidin-7-yl)-isonicotinamide,
6-Chloro-pyridine-2-carboxylic acid (2-phenyl-imidazo[1,2-a]pyrimidin-7-yl)-amide,
6-Methoxy-pyridine-2-carboxylic acid (2-phenyl-imidazo[1,2-a]pyrimidin-7-yl)-amide,
5-Bromo-3-methyl-pyridine-2-carboxylic acid (2-phenyl-imidazo[1,2-a]pyrimidin-7-yl)-amide,
4-Bromo-3,6-dimethyl-pyridine-2-carboxylic acid (2-phenyl-imidazo[1,2-a]pyrimidin-7-yl)-amide,
6-Methyl-pyridine-2-carboxylic acid (2-phenyl-imidazo[1,2-a]pyrimidin-7-yl)-amide,
Pyrazine-2,3-dicarboxylic acid 2-[(2-phenyl-imidazo[1,2-a]pyrimidin-7-yl)-amide]3-[(2,2,2-trifluoro-ethyl)-amide],
2-(Azetidine-1-carbonyl)-N-(2-phenyl-imidazo[1,2-a]pyrimidin-7-yl)-nicotinamide,
6-Cyclopropyl-3-(pyrimidin-5-ylamino)-pyridine-2-carboxylic acid (2-phenyl-imidazo[1,2-a]pyrimidin-7-yl)-amide, 2-methoxy-N-(2-phenylimidazo[1,2-a]pyrimidin-7-yl)nicotinamide,
5-chloro-2-methyl-N-(2-phenylimidazo[1,2-a]pyrimidin-7-yl)pyrimidine-4-carboxamide,
2-methyl-N-(2-phenylimidazo[1,2-a]pyrimidin-7-yl)isonicotinamide, and
2-chloro-6-methyl-N-(2-phenylimidazo[1,2-a]pyrimidin-7-yl)isonicotinamide,
or pharmaceutically acceptable salts thereof.

Another embodiment of the present invention provides compounds of formula (I')

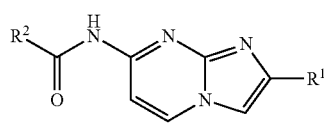

wherein
$R^1$ is phenyl or thienyl, wherein said phenyl and said thienyl are optionally substituted by 1 to 3 substituents independently selected from the group consisting of halogen, lower alkyl, lower alkoxy, lower haloalkyl, lower haloalkoxy and lower alkoxy lower alkyl;
$R^2$ is 5- or 6-membered monocyclic heteroaryl having 1 to 3 heteroatoms independently selected from N and O, wherein said heteroaryl is optionally substituted by 1 to 3 substituents independently selected from the group consisting of

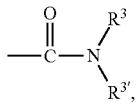

halogen, hydroxyl, nitro, lower alkyl, lower alkoxy, lower alkoxy-C(O)—, lower hydroxyalkyl, lower haloalkyl, lower alkoxy lower alkyl, lower alkyl-C(O)—, cycloalkyl, heterocyclyl, aryl, heteroaryl and amino optionally substituted by heteroaryl, wherein two substituents of $R^2$, together with said heteroaryl to which they are attached, may form a 9- or 10-membered bicyclic ring; and
$R^3$ and $R^{3'}$ are each independently hydrogen, lower alkyl optionally substituted by cycloalkyl, lower hydroxyalkyl, lower cyanoalkyl, lower haloalkyl, lower alkoxy lower alkyl, cycloalkyl or heterocyclyl, or
$R^3$ and $R^{3'}$, together with the nitrogen atom to which they are attached, form a heterocyclyl optionally substituted by 1 to 3 halogen, hydroxyl or oxo;
or pharmaceutically acceptable salts thereof.

A particular embodiment of the present invention provides compounds of formula (I') as described above, wherein $R^1$ is selected from the group consisting of:

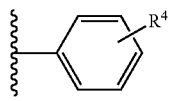 and 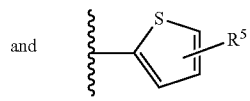

wherein
$R^4$ is hydrogen, halogen, lower alkoxy or lower haloalkoxy; and
$R^5$ is halogen.

Another embodiment of the present invention provides compounds of formula (Ia')

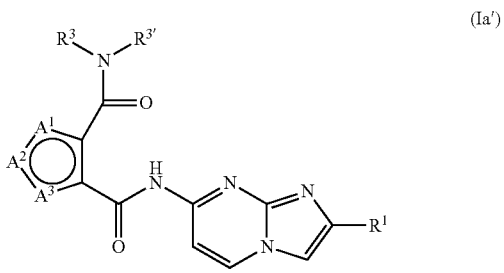

wherein
$A^1$ is —NH—, —N=, —NR$^6$— or —CH=;
$A^2$ is —N= or —NR$^{6'}$—;
$A^3$ is —N=, —NR$^{6''}$— or —CH=;
$R^6$ is lower alkyl;
$R^{6'}$ is lower alkyl;
$R^{6''}$ is lower alkyl;
$R^1$ is phenyl or thienyl, wherein said phenyl and said thienyl are optionally substituted by 1 to 3 substituents independently selected from the group consisting of halogen, lower alkoxy and lower haloalkoxy; and
$R^3$ and $R^{3'}$ are each independently hydrogen, lower alkyl optionally substituted by cycloalkyl, lower hydroxyalkyl, lower cyanoalkyl, lower alkoxy lower alkyl, cycloalkyl or heterocyclyl, or
$R^3$ and $R^{3'}$, together with the nitrogen atom to which they are attached, form a heterocyclyl optionally substituted by 1 or 2 halogen, hydroxyl or oxo.

Particular compounds of formula (Ia') are those selected from the group consisting of:
5-(Azetidine-1-carbonyl)-1H-[1,2,3]triazole-4-carboxylic acid (2-phenyl-imidazo[1,2-a]pyrimidin-7-yl)-amide,
1H-[1,2,3]Triazole-4,5-dicarboxylic acid 5-(ethyl-methyl-amide) 4-[(2-phenyl-imidazo[1,2-a]pyrimidin-7-yl)-amide],
4-(Azetidine-1-carbonyl)-2-methyl-2H-pyrazole-3-carboxylic acid (2-phenyl-imidazo[1,2-a]pyrimidin-7-yl)-amide,
2-Methyl-4-(morpholine-4-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-methylamide 3-[(2-phenyl-imidazo[1,2-a]pyrimidin-7-yl)-amide],
2-Methyl-2H-pyrazole-3,4-dicarboxylic acid 3-{[2-(3-chloro-phenyl)-imidazo[1,2-a]pyrimidin-7-yl]-amide}-4-methylamide,
2-Methyl-2H-pyrazole-3,4-dicarboxylic acid 3-{[2-(4-fluoro-phenyl)-imidazo[1,2-a]pyrimidin-7-yl]-amide}-4-methylamide,
4-(3,3-Difluoro-azetidine-1-carbonyl)-2-methyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-hydroxy-ethyl)-amide]3-[(2-phenyl-imidazo[1,2-a]pyrimidin-7-yl)-amide],
4-(3-Hydroxy-azetidine-1-carbonyl)-2-methyl-2H-pyrazole-3-carboxylic acid (2-phenyl-imidazo[1,2-a]pyrimidin-7-yl)-amide,
4-(1,1-Dioxo-1λ6-thiomorpholine-4-carbonyl)-2-methyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(3-hydroxy-propyl)-amide]3-[(2-phenyl-imidazo[1,2-a]pyrimidin-7-yl)-amide], 2-Methyl-2H-pyrazole-3,4-dicarboxylic acid 4-[(3-methoxy-propyl)-amide]3-[(2-phenyl-imidazo[1,2-a]pyrimidin-7-yl)-amide],
2-Methyl-2H-pyrazole-3,4-dicarboxylic acid 3-[(2-phenyl-imidazo[1,2-a]pyrimidin-7-yl)-amide]-4-[(tetrahydro-furan-3-yl)-amide],
2-Methyl-2H-pyrazole-3,4-dicarboxylic acid 4-[(2-hydroxy-1-methyl-ethyl)-amide]3-[(2-phenyl-imidazo[1,2-a]pyrimidin-7-yl)-amide],
2-Methyl-2H-pyrazole-3,4-dicarboxylic acid 4-[(2-hydroxy-propyl)-amide]3-[(2-phenyl-imidazo[1,2-a]pyrimidin-7-yl)-amide],
4-(Azetidine-1-carbonyl)-2-methyl-2H-pyrazole-3-carboxylic acid [2-(3-methoxy-phenyl)-imidazo[1,2-a]pyrimidin-7-yl]-amide,
2-Methyl-2H-pyrazole-3,4-dicarboxylic acid 4-[(2-methoxy-ethyl)-amide]3-[(2-phenyl-imidazo[1,2-a]pyrimidin-7-yl)-amide],
2-Methyl-2H-pyrazole-3,4-dicarboxylic acid 4-diethylamide 3-[(2-phenyl-imidazo[1,2-a]pyrimidin-7-yl)-amide],
2-Methyl-4-(pyrrolidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-(ethyl-methyl-amide) 3-[(2-phenyl-imidazo[1,2-a]pyrimidin-7-yl)-amide],
2-Methyl-2H-pyrazole-3,4-dicarboxylic acid 4-ethylamide 3-[(2-phenyl-imidazo[1,2-a]pyrimidin-7-yl)-amide],
2-Methyl-2H-pyrazole-3,4-dicarboxylic acid 4-cyclopropylamide 3-[(2-phenyl-imidazo[1,2-a]pyrimidin-7-yl)-amide],
2-Methyl-4-(piperidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-hydroxy-ethyl)-methyl-amide]3-[(2-phenyl-imidazo[1,2-a]pyrimidin-7-yl)-amide],
2-Methyl-2H-pyrazole-3,4-dicarboxylic acid 4-(isopropyl-methyl-amide) 3-[(2-phenyl-imidazo[1,2-a]pyrimidin-7-yl)-amide],
2-Methyl-2H-pyrazole-3,4-dicarboxylic acid 4-[(2-methoxy-ethyl)-methyl-amide]3-[(2-phenyl-imidazo[1,2-a]pyrimidin-7-yl)-amide],
2-Methyl-2H-pyrazole-3,4-dicarboxylic acid 4-(methyl-propyl-amide) 3-[(2-phenyl-imidazo[1,2-a]pyrimidin-7-yl)-amide],
2-Methyl-2H-pyrazole-3,4-dicarboxylic acid 3-[(2-phenyl-imidazo[1,2-a]pyrimidin-7-yl)-amide]-4-propylamide,
2-Methyl-2H-pyrazole-3,4-dicarboxylic acid 4-cyclopropyl-methyl-amide 3-[(2-phenyl-imidazo[1,2-a]pyrimidin-7-yl)-amide],
2-Methyl-2H-pyrazole-3,4-dicarboxylic acid 4-cyclobutylamide 3-[(2-phenyl-imidazo[1,2-a]pyrimidin-7-yl)-amide],
2-Methyl-2H-pyrazole-3,4-dicarboxylic acid 4-isopropylamide 3-[(2-phenyl-imidazo[1,2-a]pyrimidin-7-yl)-amide],
4-(Azetidine-1-carbonyl)-2-methyl-2H-pyrazole-3-carboxylic acid [2-(3-trifluoromethoxy-phenyl)-imidazo[1,2-a]pyrimidin-7-yl]-amide,
4-(Azetidine-1-carbonyl)-2-methyl-2H-pyrazole-3-carboxylic acid [2-(3-chloro-phenyl)-imidazo[1,2-a]pyrimidin-7-yl]-amide,
2-Ethyl-2H-pyrazole-3,4-dicarboxylic acid 4-methylamide 3-[(2-phenyl-imidazo[1,2-a]pyrimidin-7-yl)-amide],
1H-[1,2,3]Triazole-4,5-dicarboxylic acid 5-methylamide 4-[(2-phenyl-imidazo[1,2-a]pyrimidin-7-yl)-amide],
3-(Azetidine-1-carbonyl)-1-methyl-1H-pyrazole-4-carboxylic acid (2-phenyl-imidazo[1,2-a]pyrimidin-7-yl)-amide,
1-Methyl-1H-pyrazole-3,4-dicarboxylic acid 3-(ethyl-methyl-amide) 4-[(2-phenyl-imidazo[1,2-a]pyrimidin-7-yl)-amide],
1-Methyl-1H-pyrazole-3,4-dicarboxylic acid 4-(ethyl-methyl-amide) 3-[(2-phenyl-imidazo[1,2-a]pyrimidin-7-yl)-amide],
4-(Azetidine-1-carbonyl)-2-ethyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-cyano-ethyl)-methyl-amide]3-[(2-phenyl-imidazo[1,2-a]pyrimidin-7-yl)-amide],
2-Methyl-2H-pyrazole-3,4-dicarboxylic acid 4-(isobutyl-methyl-amide) 3-[(2-phenyl-imidazo[1,2-a]pyrimidin-7-yl)-amide],
2-Methyl-2H-pyrazole-3,4-dicarboxylic acid 4-[(2-hydroxy-2-methyl-propyl)-amide]3-[(2-phenyl-imidazo[1,2-a]pyrimidin-7-yl)-amide],
2-Ethyl-2H-pyrazole-3,4-dicarboxylic acid 4-(ethyl-methyl-amide) 3-[(2-phenyl-imidazo[1,2-a]pyrimidin-7-yl)-amide],
4-(Azetidine-1-carbonyl)-2-methyl-2H-pyrazole-3-carboxylic acid [2-(5-chloro-thiophen-2-yl)-imidazo[1,2-a]pyrimidin-7-yl]-amide, and
2-Methyl-2H-pyrazole-3,4-dicarboxylic acid 4-dimethylamide 3-[(2-phenyl-imidazo[1,2-a]pyrimidin-7-yl)-amide],
or pharmaceutically acceptable salts thereof.

Another embodiment of the present invention provides compounds of formula (Ia') as described above,
wherein
$R^1$ is phenyl or thienyl, wherein said phenyl and said thienyl are optionally substituted by halogen or lower alkoxy; and
$R^3$ and $R^{3'}$ are each independently lower alkyl or lower alkoxy lower alkyl, or
$R^3$ and $R^{3'}$, together with the nitrogen atom to which they are attached, form an azetidine ring or pyrrolidine ring.

Particular compounds of formula (Ia') are those selected from the group consisting of:
4-(Azetidine-1-carbonyl)-2-methyl-2H-pyrazole-3-carboxylic acid (2-phenyl-imidazo[1,2-a]pyrimidin-7-yl)-amide,
4-(Azetidine-1-carbonyl)-2-methyl-2H-pyrazole-3-carboxylic acid [2-(3-methoxy-phenyl)-imidazo[1,2-a]pyrimidin-7-yl]-amide,
2-Methyl-4-(pyrrolidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-(ethyl-methyl-amide) 3-[(2-phenyl-imidazo[1,2-a]pyrimidin-7-yl)-amide],
2-Methyl-2H-pyrazole-3,4-dicarboxylic acid 4-[(2-methoxy-ethyl)-methyl-amide]3-[(2-phenyl-imidazo[1,2-a]pyrimidin-7-yl)-amide],
4-(Azetidine-1-carbonyl)-2-methyl-2H-pyrazole-3-carboxylic acid [2-(3-chloro-phenyl)-imidazo[1,2-a]pyrimidin-7-yl]-amide,
4-(Azetidine-1-carbonyl)-2-ethyl-2H-pyrazole-3-carboxylic acid (2-phenyl-imidazo[1,2-a]pyrimidin-7-yl)-amide,
2-Ethyl-2H-pyrazole-3,4-dicarboxylic acid 4-(ethyl-methyl-amide) 3-[(2-phenyl-imidazo[1,2-a]pyrimidin-7-yl)-amide], and
2-Methyl-2H-pyrazole-3,4-dicarboxylic acid 4-dimethylamide 3-[(2-phenyl-imidazo[1,2-a]pyrimidin-7-yl)-amide],
or pharmaceutically acceptable salts thereof.

Yet particular compounds of formula (Ia') are those selected from the group consisting of:
4-(Azetidine-1-carbonyl)-2-methyl-2H-pyrazole-3-carboxylic acid [2-(5-chloro-thiophen-2-yl)-imidazo[1,2-a]pyrimidin-7-yl]-amide, or pharmaceutically acceptable salts thereof.

Another embodiment of the present invention provides compounds of formula (I') as described above, wherein $R^2$ is

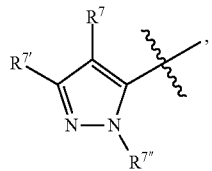

wherein
$R^7$ is hydrogen, halogen, lower alkoxy-C(O)— or heteroaryl;
$R^{7'}$ is hydrogen, lower alkyl or nitro; and
$R^{7''}$ is lower alkyl, cycloalkyl or aryl.

Particular compounds of formula (I') are those selected from the group consisting of:
4-Chloro-2-methyl-2H-pyrazole-3-carboxylic acid (2-phenyl-imidazo[1,2-a]pyrimidin-7-yl)-amide,
4-Chloro-2,5-dimethyl-2H-pyrazole-3-carboxylic acid (2-phenyl-imidazo[1,2-a]pyrimidin-7-yl)-amide,
2-Phenyl-2H-pyrazole-3-carboxylic acid (2-phenyl-imidazo[1,2-a]pyrimidin-7-yl)-amide,
4-Bromo-2,5-dimethyl-2H-pyrazole-3-carboxylic acid (2-phenyl-imidazo[1,2-a]pyrimidin-7-yl)-amide,
4-Bromo-2-methyl-2H-pyrazole-3-carboxylic acid (2-phenyl-imidazo[1,2-a]pyrimidin-7-yl)-amide,
4-Chloro-2-ethyl-2H-pyrazole-3-carboxylic acid (2-phenyl-imidazo[1,2-a]pyrimidin-7-yl)-amide,
4-Chloro-2-propyl-2H-pyrazole-3-carboxylic acid (2-phenyl-imidazo[1,2-a]pyrimidin-7-yl)-amide,
2-Butyl-4-chloro-2H-pyrazole-3-carboxylic acid (2-phenyl-imidazo[1,2-a]pyrimidin-7-yl)-amide,
4-Chloro-2-isopropyl-2H-pyrazole-3-carboxylic acid (2-phenyl-imidazo[1,2-a]pyrimidin-7-yl)-amide,
2-sec-Butyl-4-chloro-2H-pyrazole-3-carboxylic acid (2-phenyl-imidazo[1,2-a]pyrimidin-7-yl)-amide,
4-Chloro-2-isobutyl-2H-pyrazole-3-carboxylic acid (2-phenyl-imidazo[1,2-a]pyrimidin-7-yl)-amide,
2-Isobutyl-5-nitro-2H-pyrazole-3-carboxylic acid (2-phenyl-imidazo[1,2-a]pyrimidin-7-yl)-amide,
2-Cyclopentyl-5-nitro-2H-pyrazole-3-carboxylic acid (2-phenyl-imidazo[1,2-a]pyrimidin-7-yl)-amide,
2-Ethyl-5-nitro-2H-pyrazole-3-carboxylic acid (2-phenyl-imidazo[1,2-a]pyrimidin-7-yl)-amide,
2-Isopropyl-5-nitro-2H-pyrazole-3-carboxylic acid (2-phenyl-imidazo[1,2-a]pyrimidin-7-yl)-amide,
4-Isoxazol-5-yl-2-methyl-2H-pyrazole-3-carboxylic acid (2-phenyl-imidazo[1,2-a]pyrimidin-7-yl)-amide, and
1-Ethyl-5-(2-phenyl-imidazo[1,2-a]pyrimidin-7-ylcarbamoyl)-1H-pyrazole-4-carboxylic acid ethyl ester, or pharmaceutically acceptable salts thereof.

Yet particular compounds of formula (I') are those selected from the group consisting of:
Isoxazole-5-carboxylic acid (2-phenyl-imidazo[1,2-a]pyrimidin-7-yl)-amide,
4,5,6,7-Tetrahydro-benzo[d] isoxazole-3-carboxylic acid (2-phenyl-imidazo[1,2-a]pyrimidin-7-yl)-amide,
5-(2-Phenyl-imidazo[1,2-a]pyrimidin-7-ylcarbamoyl)-3H-[1,2,3]triazole-4-carboxylic acid methyl ester, and
1-Methyl-3-(pyrimidin-5-ylamino)-1H-pyrazole-4-carboxylic acid (2-phenyl-imidazo[1,2-a]pyrimidin-7-yl)-amide, or pharmaceutically acceptable salts thereof.

Another embodiment of the present invention provides compounds of formula (I') as described above, wherein $R^2$ is 6-membered heteroaryl selected from the group consisting of:

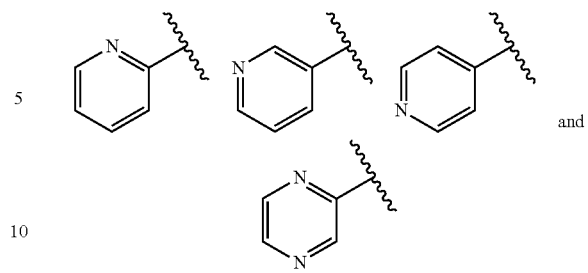

and wherein said heteroaryl is substituted by 1 to 3 substituents independently selected from the group consisting of bromo, chloro, methyl, methoxy, cyclopropyl, —C(O)NHCH$_2$CF$_3$,

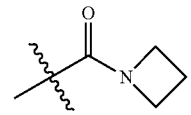 [SMILES: *C(=O)N1CCC1]

and pyrimidin-5-ylamino.

Particular compounds of formula (I') are those selected from the group consisting of:
3,6-Dimethyl-pyridine-2-carboxylic acid (2-phenyl-imidazo[1,2-a]pyrimidin-7-yl)-amide,
2-Chloro-N-(2-phenyl-imidazo[1,2-a]pyrimidin-7-yl)-isonicotinamide,
6-Chloro-pyridine-2-carboxylic acid (2-phenyl-imidazo[1,2-a]pyrimidin-7-yl)-amide,
6-Methoxy-pyridine-2-carboxylic acid (2-phenyl-imidazo[1,2-a]pyrimidin-7-yl)-amide,
5-Bromo-3-methyl-pyridine-2-carboxylic acid (2-phenyl-imidazo[1,2-a]pyrimidin-7-yl)-amide,
4-Bromo-3,6-dimethyl-pyridine-2-carboxylic acid (2-phenyl-imidazo[1,2-a]pyrimidin-7-yl)-amide,
6-Methyl-pyridine-2-carboxylic acid (2-phenyl-imidazo[1,2-a]pyrimidin-7-yl)-amide,
Pyrazine-2,3-dicarboxylic acid 2-[(2-phenyl-imidazo[1,2-a]pyrimidin-7-yl)-amide]3-[(2,2,2-trifluoro-ethyl)-amide],
2-(Azetidine-1-carbonyl)-N-(2-phenyl-imidazo[1,2-a]pyrimidin-7-yl)-nicotinamide, and
6-Cyclopropyl-3-(pyrimidin-5-ylamino)-pyridine-2-carboxylic acid (2-phenyl-imidazo[1,2-a]pyrimidin-7-yl)-amide, or pharmaceutically acceptable salts thereof.

It will be appreciated that the compounds of general formula (I) in this invention may be derivatized at functional groups to provide derivatives which are capable of conversion back to the parent compound in vivo.

The invention further provides a process for the manufacture of compounds of formula (I) as defined above, which process comprises:
reacting a compound of formula 3

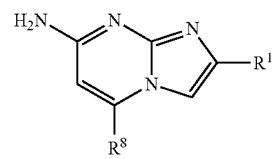

with a compound of formula 2

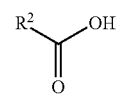

wherein $R^1$, $R^2$ and $R^8$ are as defined above, and if desired, converting the compounds into pharmaceutically acceptable salts thereof.

The reaction described above can be carried out under conditions as described in the description and examples or under conditions well known to the person skilled in the art.

The compounds of formula 2 and 3 can be prepared by methods known in the art or as described below or in analogy thereto.

The present invention also provides compounds of formula (I) as defined above, when prepared by a process as described above.

Compounds of formula 1 can be prepared from building blocks 2 and 3 according to Scheme 1. The conversion, commonly known as amide coupling, can be achieved in several ways. In one method, the acid 2 is activated with a coupling reagent, such as 2-(1H-benzotriazole-1-yl)-1,1,3,3-tetramethyluronium tetrafluoroborate (TBTU), or propylphosphonic anhydride, and converted by addition of amine 3 to the desired product, 1. In another method, the acid 2 is activated by transformation into an acid chloride, e.g. by reaction with thionyl chloride. The acid chloride is then converted by addition of the amine 3 to the desired product, 1. A base, e.g. diisopropylethylamine (DIPEA), is usually added to bind liberated HCl.

Scheme 1

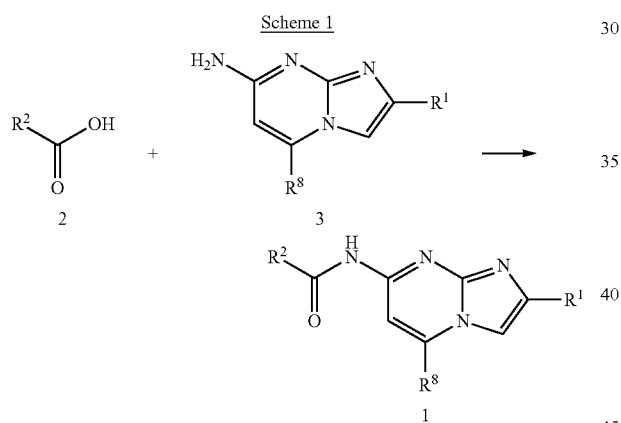

Compounds of formula 3 can be prepared according to Scheme 2: 2,4-diaminopyrimidine (4) is reacted with a compound 5, such as a (substituted) 2-bromoacetophenone, or such as a (substituted) 2-bromo-1-thiophen-2-yl-ethanone, with a suitable base, such as NaHCO$_3$, to give 3. 2,4-Diaminopyrimidine 4 is commercially available; compounds 5 are either commercially available, or can be prepared by methods well known in the art.

Scheme 2

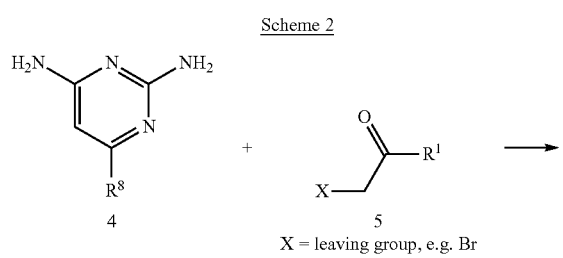

X = leaving group, e.g. Br

-continued

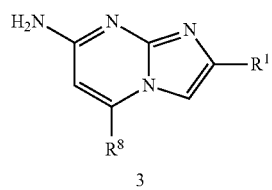

Compounds of formula 2, with $R^2$ being a pyrazolyl carboxylic acid derivative, can be prepared according to Scheme 3, wherein $R^{6''}$ is as defined above: Compound 6 is reacted with a hydrazine 7, or a salt thereof, to give a pyrazole 8 (similar to the method of A. Hanzlowsky, B. Jelencic, S. Recnik, J. Svete, A. Golobic, B. Stanovnik *J. Heterocyclic Chem.* 2003, 40(3), 487-498). Selective mono-saponification of the diester 8 yields, depending on the reaction conditions, compound 2a or its isomer, compound 2b.

Scheme 3

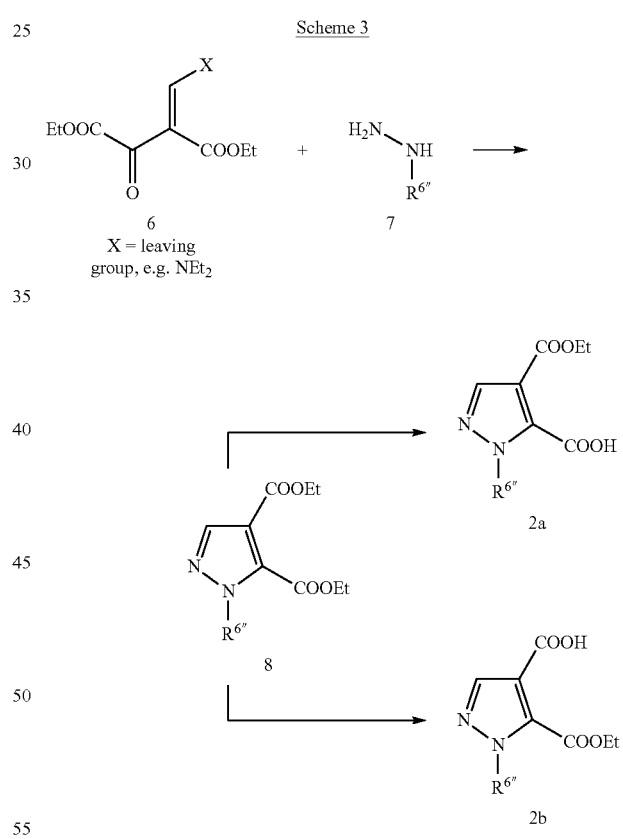

Compounds of formula 1, with $R^2$ being a lower alkoxycarbonyl-substituted heteroaromatic ring, can be further transformed according to Scheme 4, wherein $R^3$ and $R^{3'}$ are as defined above. For instance, compounds of the general formula 1-COOEt can be saponified by suitable methods, e.g. by reaction with KOH, to give 1-COOH. Upon activation with a suitable reagent such as TBTU, 1-COOH can be converted with a primary or secondary amine to 1-CONR$^3$R$^{3'}$. Alternatively, 1-COOEt can be directly converted into 1-CO NR$^3$R$^{3'}$, e.g. by reaction with an amine such as methylamine.

Scheme 4

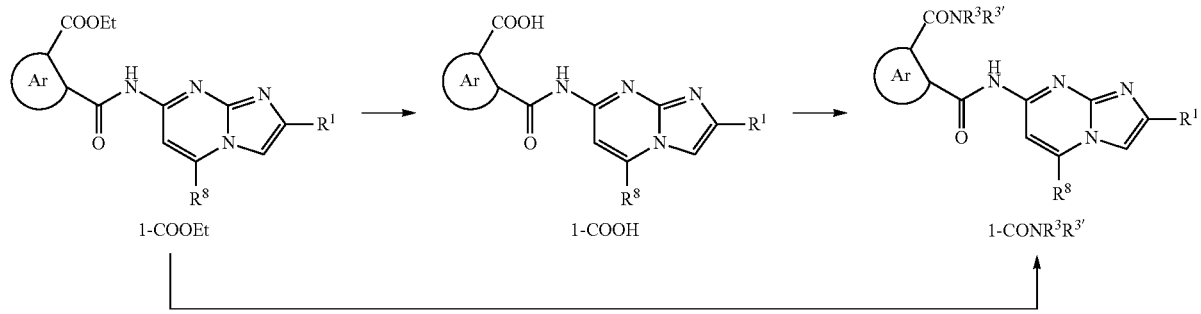

Alternatively, compounds of formula 1, with $R^2$ being an amide-substituted pyrazole ring, can be obtained according to Scheme 5: Upon activation with a suitable reagent such as TBTU, 1-methyl-1H-pyrazole-4-carboxylic acid (9) can be converted with a primary or secondary amine to 10. A suitable base, such as triethylamine, may be added. Metallation with a suitable agent such as tBuLi, and subsequent reaction with $CO_2$ yields carboxylic acid 11. A complexing agent, such as pentamethyldiethylenetriamine, may be added in the metallation step. Coupling of 11 with 3, in close analogy to Scheme 1, delivers 1-pyrazolylamide.

Scheme 5

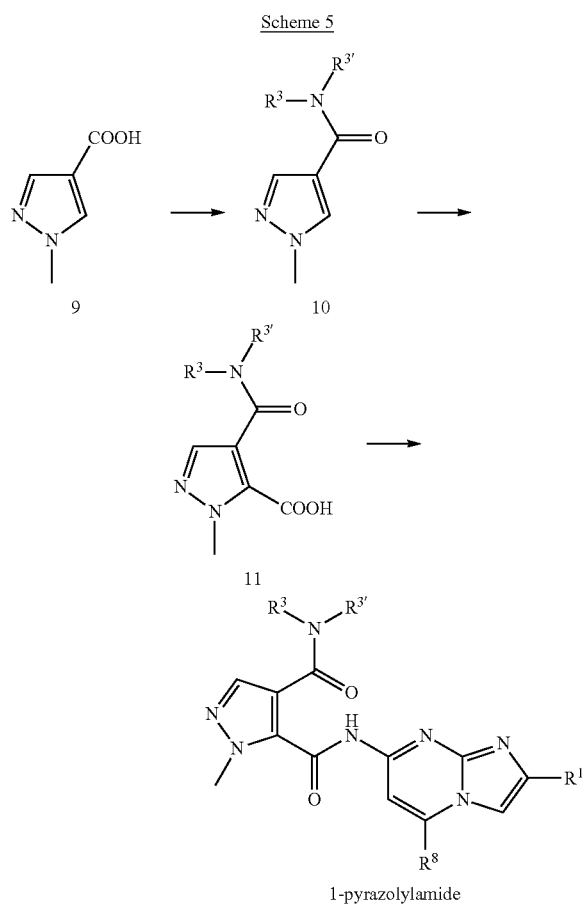

All reactions are typically performed in a suitable solvent and under an atmosphere of argon or nitrogen.

The corresponding salts with acids can be obtained by standard methods known to the person skilled in the art, e.g. by dissolving the compound of formula (I) in a suitable solvent such as e.g. dioxane or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M is metal or ammonium cation and n is number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of a suitable carboxy group present in the molecule with a suitable alcohol using e.g. a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or o-(1,2-dihydro-2-oxo-1-pyridyl)-N,N,N,N-tetra-methyluronium-tetrafluoroborate (TPTU), or by direct reaction with a suitable alcohol under acidic conditions, as for example in the presence of a strong mineral acid like hydrochloric acid, sulfuric acid and the like. Compounds having a hydroxyl group can be converted to esters with suitable acids by analogous methods.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

As described above, the novel compounds of the present invention have been found to inhibit PDE10A activity. The compounds of the present invention can therefore be used, either alone or in combination with other drugs, for the treatment and/or prophylaxis of diseases which are modulated by PDE10A inhibitors. These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive/compulsive disorders, acute stress disorder or generalized anxiety disorder, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Other disorders are diabetes and related disorders, such as type 2 diabetes mellitus, neurodegenerative disorders such as Alzheimer's disease, Huntington's disease, Parkinson's disease, multiple sclerosis, stroke or spinal cord injury, solid tumors and hematological malignancies such as renal cell carcinoma or breast cancer.

The invention therefore also provides pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases which are modulated by PDE10A inhibitors, particularly as therapeutically active substances for the treatment and/or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

In another embodiment, the invention provides a method for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer, which method comprises administering a compound as defined above to a human being or animal.

The invention also embraces the use of compounds as defined above for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer.

The invention also provides the use of compounds as described above for the preparation of medicaments for the therapeutic and/or prophylactic treatment of diseases which are modulated by PDE10A inhibitors, particularly for the therapeutic and/or prophylactic treatment of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma and breast cancer. Such medicaments comprise a compound as described above.

In another embodiment, the invention provides a compound or a pharmaceutically acceptable salt thereof as defined above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Prevention and/or treatment of schizophrenia is a particular indication. Yet particular indication is prevention and/or treatment of positive, negative and/or cognitive symptoms associated with schizophrenia.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7):3702-3707).

The human PDE10A full length assay was performed in 96-well micro titer plates. The reaction mixture of 50 µl contained 20 mM HEPES pH=7.5/10 mM $MgCl_2$/0.05 mg/ml BSA (Sigma cat. #A-7906), 50 nM cGMP (Sigma, cat. #G6129) and 50 nM [$^3$H]-cGMP (GE Healthcare, cat. #TRK392 S.A. 13.2 Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. $IC_{50}$, the concentration of the competitor inhibiting PDE10A activity by 50%). Non-specific activity was tested without the enzyme. The reaction was initiated by the addition of the substrate solution (cGMP and [$^3$H]-cGMP) and allowed to progress for 20 minutes at room temperature. The reaction was terminated by adding 25 µl of YSi-SPA scintillation beads (GE Healthcare, cat. #RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer TopCount Scintillation plate reader.

The compounds according to formula (I) have an $IC_{50}$ value below 10 µM, more specifically below 5 µM, yet more specifically below 1 µM. The following table shows data for some examples.

| Example | PDE10A inhibition $IC_{50}$ [µmol/l] |
|---|---|
| 2 | 0.9513 |
| 3 | 0.097 |
| 4 | 0.6709 |
| 5 | 0.0268 |
| 6 | 0.3841 |
| 7 | 0.1404 |
| 8 | 0.0647 |
| 9 | 0.0446 |
| 10 | 0.105 |
| 11 | 0.1053 |
| 12 | 0.0188 |
| 13 | 0.0479 |
| 14 | 0.1252 |
| 15 | 0.7485 |
| 16 | 0.0821 |
| 17 | 0.0283 |
| 18 | 0.1475 |
| 19 | 0.5529 |
| 20 | 0.6431 |
| 21 | 0.3136 |
| 22 | 0.042 |
| 23 | 0.0643 |
| 24 | 0.3207 |
| 25 | 0.324 |
| 26 | 0.024 |
| 27 | 0.1627 |
| 28 | 0.2509 |
| 29 | 0.0033 |
| 30 | 0.0331 |
| 32 | 0.0228 |
| 34 | 0.035 |
| 36 | 0.032 |
| 38 | 0.0229 |
| 39 | 0.0864 |
| 43 | 0.8996 |
| 44 | 0.8128 |
| 45 | 0.0083 |
| 46 | 0.7848 |
| 47 | 0.0152 |
| 48 | 0.0035 |
| 49 | 0.0019 |
| 50 | 0.0244 |
| 51 | 0.0148 |
| 52 | 0.0029 |
| 53 | 0.0236 |
| 54 | 0.0343 |
| 55 | 0.0085 |
| 56 | 0.0173 |
| 57 | 0.023 |
| 58 | 0.0273 |
| 59 | 0.0211 |
| 60 | 0.0806 |
| 61 | 0.0235 |
| 62 | 0.0129 |
| 63 | 0.0048 |
| 64 | 0.0065 |
| 65 | 0.0348 |
| 66 | 0.0115 |
| 67 | 0.0257 |
| 68 | 0.0377 |
| 69 | 0.0044 |
| 70 | 0.0332 |
| 71 | 0.0176 |
| 72 | 0.4634 |
| 73 | 0.0028 |
| 74 | 0.004 |
| 75 | 0.0049 |
| 77 | 0.0063 |
| 78 | 0.1246 |
| 79 | 0.2467 |
| 80 | 0.4963 |
| 81 | 0.7034 |
| 82 | 0.0034 |
| 83 | 0.0034 |
| 84 | 0.0038 |
| 85 | 0.004 |
| 86 | 0.0052 |
| 87 | 0.0055 |
| 88 | 0.0057 |
| 89 | 0.0061 |
| 90 | 0.0061 |
| 91 | 0.0061 |
| 92 | 0.0065 |
| 93 | 0.0083 |
| 94 | 0.0112 |
| 95 | 0.0122 |
| 96 | 0.0126 |
| 97 | 0.0147 |
| 98 | 0.0147 |
| 99 | 0.019 |
| 100 | 0.0218 |
| 101 | 0.022 |
| 102 | 0.0279 |
| 103 | 0.0287 |
| 104 | 0.0296 |
| 105 | 0.0366 |
| 106 | 0.0433 |
| 107 | 0.0519 |
| 108 | 0.0817 |
| 109 | 0.089 |
| 110 | 0.2219 |
| 111 | 0.3644 |
| 112 | 0.0013 |
| 113 | 0.0026 |
| 114 | 0.0028 |
| 115 | 0.0051 |
| 116 | 0.0051 |
| 117 | 0.0062 |
| 118 | 0.0119 |
| 119 | 0.0133 |
| 120 | 0.0137 |
| 121 | 0.0167 |
| 122 | 0.0169 |
| 123 | 0.0173 |
| 124 | 0.0177 |
| 125 | 0.0187 |
| 126 | 0.0247 |
| 127 | 0.0259 |
| 128 | 0.026 |
| 129 | 0.0332 |
| 130 | 0.0349 |
| 131 | 0.0351 |
| 132 | 0.0486 |
| 133 | 0.0522 |
| 134 | 0.0576 |
| 135 | 0.0641 |
| 136 | 0.0997 |
| 137 | 0.1173 |
| 138 | 0.1305 |
| 139 | 0.1484 |
| 140 | 0.1506 |
| 141 | 0.1509 |
| 142 | 0.1517 |
| 143 | 0.162 |
| 144 | 0.1984 |
| 145 | 0.2105 |
| 146 | 0.2123 |
| 147 | 0.2345 |
| 148 | 0.2439 |
| 149 | 0.2602 |

| Example | PDE10A inhibition IC$_{50}$ [µmol/l] |
|---|---|
| 150 | 0.2634 |
| 151 | 0.2875 |
| 152 | 0.3022 |
| 153 | 0.3053 |
| 154 | 0.3148 |
| 155 | 0.346 |
| 156 | 0.359 |
| 157 | 0.3895 |
| 158 | 0.427 |
| 159 | 0.4508 |
| 160 | 0.4585 |
| 161 | 0.5471 |
| 162 | 0.6236 |
| 163 | 0.636 |
| 164 | 0.725 |
| 165 | 0.7759 |
| 166 | 0.8121 |
| 167 | 0.8247 |
| 168 | 0.8654 |
| 169 | 0.9633 |
| 170 | 0.9693 |
| 171 | 0.9886 |

The compounds of formula (I) and/or their pharmaceutically acceptable salts can be used as medicaments, e.g. in the form of pharmaceutical compositions for enteral, parenteral or topical administration. They can be administered, for example, perorally, e.g. in the form of tablets, coated tablets, dragées, hard and soft gelatin capsules, solutions, emulsions or suspensions, rectally, e.g. in the form of suppositories, parenterally, e.g. in the form of injection solutions or suspensions or infusion solutions, or topically, e.g. in the form of ointments, creams or oils.

The production of the pharmaceutical compositions can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical compositions are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage at which compounds of formula (I) can be administered can vary within wide limits depending on the disease to be controlled, the age and the individual condition of the patient and the mode of administration, and will, of course, be fitted to the individual requirements in each particular case. For adult patients a daily dosage of about 0.1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical compositions conveniently contain about 0.1-500 mg, more specifically 1-200 mg, of a compound of formula (I).

The following examples serve to illustrate the present invention in more detail. They are, however, not intended to limit its scope in any manner.

EXAMPLES

Example 1

4-Chloro-2-methyl-2H-pyrazole-3-carboxylic acid (2-phenyl-imidazo[1,2-a]pyrimidin-7-yl)-amide

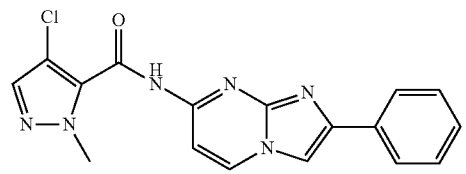 [SMILES: Cn1ncc(Cl)c1C(=O)Nc1ccn2cc(-c3ccccc3)nc2n1]

Step 1: 2-Phenyl-imidazo[1,2-a]pyrimidin-7-ylamine

Bromoacetophenone (2.71 g, 14 mmol) was added to a solution of 2,4-diaminopyrimidine (1.00 g, 9 mmol) in acetone (40 ml), and the mixture was heated to reflux for 5 h. The cooled suspension was filtered, the precipitate was washed (acetone), and then stirred for 15 min in a mixture of 10 ml water and 15 ml NH$_4$OH (25%). The suspension was filtered, washed (water), and dried under vacuum. The crude product (1.9 g, quant.) was used in the next step without further purification.

MS (m/e)=211.1 [M+H$^+$].

Step 2: 4-Chloro-2-methyl-2H-pyrazole-3-carboxylic acid (2-phenyl-imidazo[1,2-a]pyrimidin-7-yl)-amide TBTU (2-[1H-benzotriazole-1-yl]-1,1,3,3-tetramethyluronium tetrafluoroborate, 180 mg, 0.56 mmol) and diisopropylethylamine (181 mg, 1.4 mmol) were added to a solution of 4-chlor-2-methyl-2H-pyrazole-3-carboxylsäure (ArtChem, 75 mg, 0.47 mmol) in DMF (2 ml), and the mixture was stirred for 30 min. 2-Phenyl-imidazo[1,2-a]pyrimidin-7-ylamine (100 mg, 0.48 mmol) was added to the black solution, and the mixture was stirred overnight at RT. Due to incomplete conversion, additional amounts of 4-chloro-2-methyl-2H-pyrazole-3-carboxylic acid (2-phenyl-imidazo[1,2-a]pyrimidin-7-yl)-amide, TBTU, and diisopropylethylamine were added, and the mixture was stirred for an additional 24 h. The reaction mixture was taken up in ethyl acetate, washed (water), dried (Na$_2$SO$_4$), and concentrated under reduced pressure. The title compound (17 mg, 10%) was obtained from the residue by preparative HPLC (254 nm, Agilent Zorbax XdB-C18, Run: 7 min, Flow: 30 ml/min, Gradient: 0.0 min: 95/5 H$_2$O/CH$_3$CN; 0.5 min: 95/5 H$_2$O/CH$_3$CN 4.5 min: 5/95 H$_2$O/CH$_3$CN; 6.9 min 5/95 H$_2$O/CH$_3$CN; 7 min 95/5 H$_2$O/CH$_3$CN). MS (m/e)=353.2 [M+H$^+$].

Example 2

Isoxazole-5-carboxylic acid (2-phenyl-imidazo[1,2-a]pyrimidin-7-yl)-amide

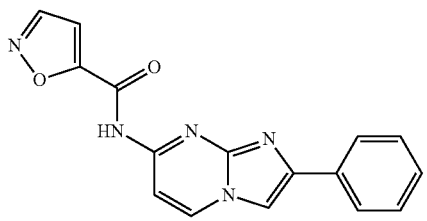 [SMILES: O=C(Nc1ccn2cc(-c3ccccc3)nc2n1)c1ccno1]

Triethylamine and 5-ethyl-isoxazole-3-carbonyl chloride were added to a solution of 2-phenyl-imidazo[1,2-a]pyrimidin-7-ylamine (example 1, step 1) in dichloromethane, and the mixture was stirred at RT overnight. The title compound (29 mg, 16%) was isolated from the mixture by preparative HPLC (254 nm, Agilent Zorbax XdB-C18, Run: 7 min, Flow: 30 ml/min, Gradient: 0.0 min: 95/5 H$_2$O/CH$_3$CN; 0.5 min: 95/5 H$_2$O/CH$_3$CN 4.5 min: 5/95 H$_2$O/CH$_3$CN; 6.9 min 5/95 H$_2$O/CH$_3$CN; 7 min 95/5 H$_2$O/CH$_3$CN).

MS (m/e)=306.3 [M+H$^+$].

Example 3

4-Chloro-2,5-dimethyl-2H-pyrazole-3-carboxylic acid (2-phenyl-imidazo[1,2-a]pyrimidin-7-yl)-amide

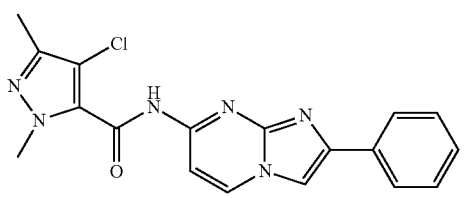

4-Chloro-2,5-dimethyl-2H-pyrazole-3-carboxylic acid (100 mg, 0.57 mmol) and diisopropylethylamine (369 mg, 2.86 mmol) were added to a solution of 2-phenyl-imidazo[1,2-a]pyrimidin-7-ylamine (example 1, step 1, 100 mg, 0.48 mmol) in ethyl acetate (3 ml). At 0° C., propylphosphonic acid anhydride (1-propanephosphonic acid cyclic anhydride, 50% in ethyl acetate, 0.7 ml, 2.5 eq.) was added dropwise to the mixture. After stirring for 30 min at 0° C., the mixture was stirred overnight at RT. The mixture was taken up in ethyl acetate, washed (water), dried (Na$_2$SO$_4$), and concentrated under reduced pressure. The title compound (16 mg, 9%) was obtained from the residue by preparative HPLC (254 nm, Agilent Zorbax XdB-C18, Run: 7 min, Flow: 30 ml/min, Gradient: 0.0 min: 95/5 H$_2$O/CH$_3$CN; 0.5 min: 95/5 H$_2$O/CH$_3$CN 4.5 min: 5/95 H$_2$O/CH$_3$CN; 6.9 min 5/95 H$_2$O/CH$_3$CN; 7 min 95/5 H$_2$O/CH$_3$CN).

MS (m/e)=367.1 [M+H$^+$].

Example 4

2-Phenyl-2H-pyrazole-3-carboxylic acid (2-phenyl-imidazo[1,2-a]pyrimidin-7-yl)-amide

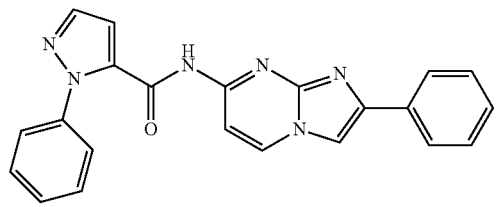 [SMILES: O=C(Nc1ccn2cc(-c3ccccc3)nc2n1)c1ccnn1-c1ccccc1]

The title compound was obtained in analogy to example 3 from 4-chloro-2,5-dimethyl-2H-pyrazole-3-carboxylic acid. MS (m/e)=381.2 [M+H$^+$].

Example 5

4-Bromo-2,5-dimethyl-2H-pyrazole-3-carboxylic acid (2-phenyl-imidazo[1,2-a]pyrimidin-7-yl)-amide

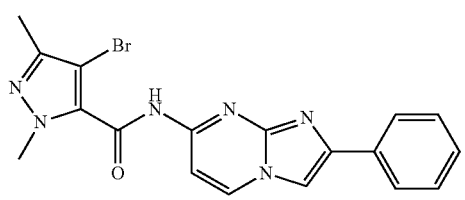 [SMILES: Cc1nn(C)c(C(=O)Nc2ccn3cc(-c4ccccc4)nc3n2)c1Br]

The title compound was obtained in analogy to example 3 from 4-bromo-2,5-dimethyl-2H-pyrazole-3-carboxylic acid. MS (m/e)=411.2 [M+H$^+$].

Example 6

4-Bromo-2-methyl-2H-pyrazole-3-carboxylic acid (2-phenyl-imidazo[1,2-a]pyrimidin-7-yl)-amide

The title compound was obtained in analogy to example 3 from 4-bromo-2-methyl-2H-pyrazole-3-carboxylic acid. MS (m/e)=397.2 [M+H$^+$].

Example 7

4-Chloro-2-ethyl-2H-pyrazole-3-carboxylic acid (2-phenyl-imidazo[1,2-a]pyrimidin-7-yl)-amide

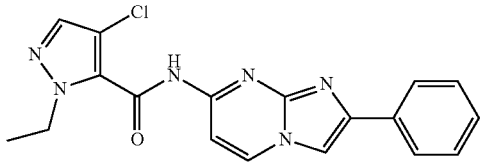 [SMILES: CCn1ncc(Cl)c1C(=O)Nc1ccn2cc(-c3ccccc3)nc2n1]

The title compound was obtained in analogy to example 3 from 4-chloro-2-ethyl-2H-pyrazole-3-carboxylic acid (ArtChem). MS (m/e)=367.2 [M+H$^+$].

Example 8

4-Chloro-2-propyl-2H-pyrazole-3-carboxylic acid (2-phenyl-imidazo[1,2-a]pyrimidin-7-yl)-amide

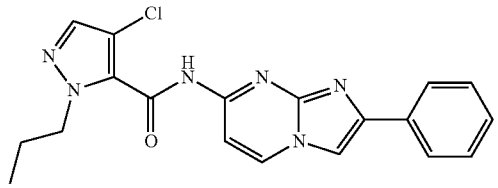 [SMILES: CCCn1ncc(Cl)c1C(=O)Nc1ccn2cc(-c3ccccc3)nc2n1]

The title compound was obtained in analogy to example 3 from 4-chloro-2-propyl-2H-pyrazole-3-carboxylic acid (ArtChem). MS (m/e)=381.2 [M+H$^+$].

Example 9

2-Butyl-4-chloro-2H-pyrazole-3-carboxylic acid (2-phenyl-imidazo[1,2-a]pyrimidin-7-yl)-amide

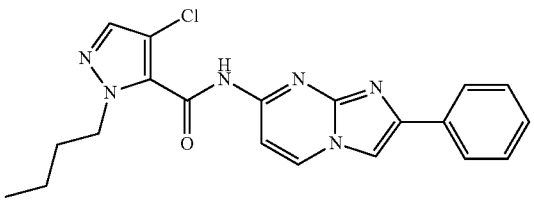 [SMILES: CCCCn1ncc(Cl)c1C(=O)Nc1ccn2cc(-c3ccccc3)nc2n1]

The title compound was obtained in analogy to example 3 from 4-Chloro-2-butyl-2H-pyrazole-3-carboxylic acid (ArtChem). MS (m/e)=395.1 [M+H$^+$].

Example 10

4-Chloro-2-isopropyl-2H-pyrazole-3-carboxylic acid (2-phenyl-imidazo[1,2-a]pyrimidin-7-yl)-amide

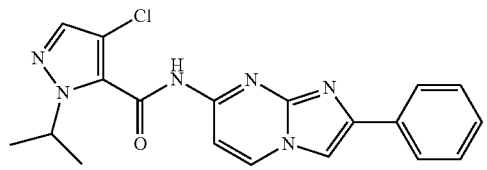 [SMILES: CC(C)n1ncc(Cl)c1C(=O)Nc1ccn2cc(-c3ccccc3)nc2n1]

The title compound was obtained in analogy to example 3 from 4-chloro-2-isopropyl-2H-pyrazole-3-carboxylic acid (ArtChem). MS (m/e)=381.3 [M+H$^+$].

Example 11

2-sec-Butyl-4-chloro-2H-pyrazole-3-carboxylic acid (2-phenyl-imidazo[1,2-a]pyrimidin-7-yl)-amide

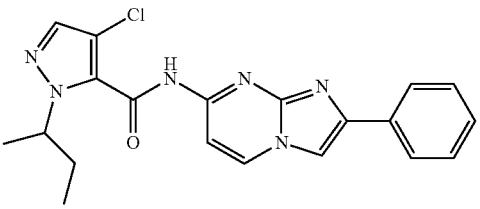 [SMILES: CCC(C)n1ncc(Cl)c1C(=O)Nc1ccn2cc(-c3ccccc3)nc2n1]

The title compound was obtained in analogy to example 3 from 2-sec-butyl-4-chloro-2H-pyrazole-3-carboxylic acid (ArtChem). MS (m/e)=395.2 [M+H$^+$].

Example 12

4-Chloro-2-isobutyl-2H-pyrazole-3-carboxylic acid (2-phenyl-imidazo[1,2-a]pyrimidin-7-yl)-amide

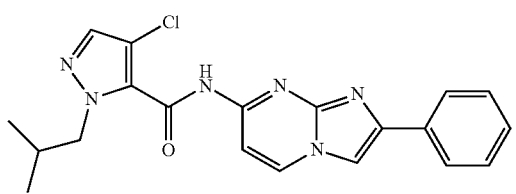 [SMILES: CC(C)Cn1ncc(Cl)c1C(=O)Nc1ccn2cc(-c3ccccc3)nc2n1]

The title compound was obtained in analogy to example 3 from 4-chloro-2-isobutyl-2H-pyrazole-3-carboxylic acid (ArtChem). MS (m/e)=395.1 [M+H$^+$].

Example 13

2-Isobutyl-5-nitro-2H-pyrazole-3-carboxylic acid (2-phenyl-imidazo[1,2-a]pyrimidin-7-yl)-amide

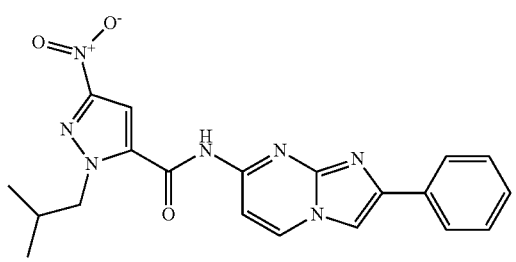 [SMILES: CC(C)Cn1nc([N+](=O)[O-])cc1C(=O)Nc1ccn2cc(-c3ccccc3)nc2n1]

The title compound was obtained in analogy to example 3 from 2-isobutyl-5-nitro-2H-pyrazole-3-carboxylic acid (ArtChem). MS (m/e)=406.3 [M+H⁺].

Example 14

2-Cyclopentyl-5-nitro-2H-pyrazole-3-carboxylic acid (2-phenyl-imidazo[1,2-a]pyrimidin-7-yl)-amide

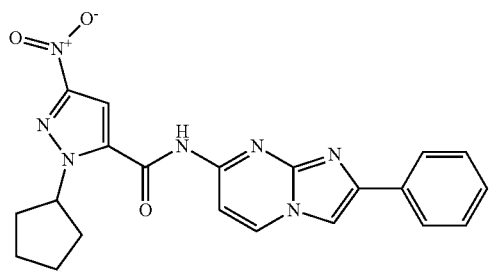 [SMILES: O=C(Nc1ccn2cc(-c3ccccc3)nc2n1)c1cc([N+](=O)[O-])nn1C1CCCC1]

The title compound was obtained in analogy to example 3 from 2-cyclopentyl-5-nitro-2H-pyrazole-3-carboxylic acid (ArtChem). MS (m/e)=418.3 [M+H⁺].

Example 15

2-Ethyl-5-nitro-2H-pyrazole-3-carboxylic acid (2-phenyl-imidazo[1,2-a]pyrimidin-7-yl)-amide

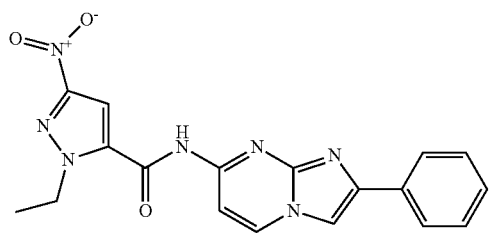 [SMILES: CCn1nc([N+](=O)[O-])cc1C(=O)Nc1ccn2cc(-c3ccccc3)nc2n1]

The title compound was obtained in analogy to example 3 from 2-ethyl-5-nitro-2H-pyrazole-3-carboxylic acid (ArtChem). MS (m/e)=378.3 [M+H⁺].

Example 16

2-Isopropyl-5-nitro-2H-pyrazole-3-carboxylic acid (2-phenyl-imidazo[1,2-a]pyrimidin-7-yl)-amide

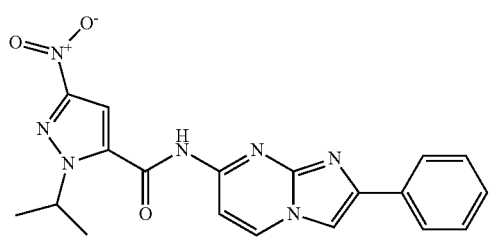 [SMILES: CC(C)n1nc([N+](=O)[O-])cc1C(=O)Nc1ccn2cc(-c3ccccc3)nc2n1]

The title compound was obtained in analogy to example 3 from 2-isopropyl-5-nitro-2H-pyrazole-3-carboxylic acid (ArtChem). MS (m/e)=392.2 [M+H⁺].

Example 17

3,6-Dimethyl-pyridine-2-carboxylic acid (2-phenyl-imidazo[1,2-a]pyrimidin-7-yl)-amide

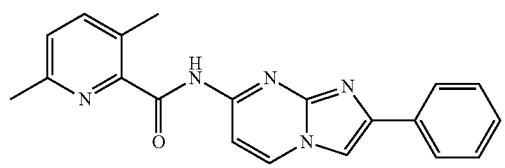 [SMILES: Cc1ccc(C)c(C(=O)Nc2ccn3cc(-c4ccccc4)nc3n2)n1]

Step 1: 3,6-Dimethyl-pyridine-2-carboxylic acid methyl ester

Trimethylsilyldiazomethane 2M in ether (5.7 ml, 11.4 mmole, 1.4 eq.) is added dropwise at RT to a suspension of 3,6-dimethyl-pyridine-2-carboxylic acid (containing potassium chloride) (3.07 g à 25%, 8.12 mmole, 1 eq.) in benzene (24 ml) and methanol (8 ml), and the yellow suspension is stirred at RT for 1.5 h. The yellow mixture is diluted with ethyl actate, washed once with sat. aqueous sodium bicarbonate sol., once with water, once with brine, dried with magnesium sulfate and the solvents are removed in vacuo. Purification of the residue (914 mg) by chromatography on a 20 g Silicycle silica cartridge (eluent heptane/ethyl acetate 5-40% 20 min) affords 3,6-dimethyl-pyridine-2-carboxylic acid methyl ester (714 mg, 53.2%) as a colorless liquid. MS (m/e)=166.3 [M+H⁺].

Step 2: 3,6-Dimethyl-pyridine-2-carboxylic acid (2-phenyl-imidazo[1,2-a]pyrimidin-7-yl)-amide To a white suspension of 2-phenyl-imidazo[1,2-a]pyrimidin-7-ylamine (example 1, step 1, 80 mg, 0.38 mmole) in dioxane (3 ml) is added at RT trimethyl aluminium sol. 2M in toluene (0.8 ml, 1.52 mmole, 4 eq.). The mixture is stirred for 45 min at RT. A solution of 3,6-dimethyl-pyridine-2-carboxylic acid methyl ester (63 mg, 0.38 mmole, 1 eq.) in dioxane (0.4 ml) is then added and the light brown solution is refluxed overnight. The brown solution is loaded on 2 g silica and purified by chromatography on a 12 g RediSep silica cartridge (eluent heptane/ethyl acetate 30-70% 15 min) affording 3,6-dimethyl-N-(2-phenylimidazo[1,2-a]pyrimidin-7-yl) picolinamide (57 mg, 43.6%) as a white solid. MS (m/e)=344.2 [M+H⁺].

Example 18

4,5,6,7-Tetrahydro-benzo[d] isoxazole-3-carboxylic acid (2-phenyl-imidazo[1,2-a]pyrimidin-7-yl)-amide

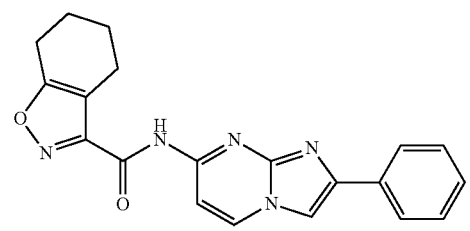 [SMILES: O=C(Nc1ccn2cc(-c3ccccc3)nc2n1)c1noc2c1CCCC2]

The title compound was obtained in analogy to example 3 from 4,5,6,7-tetrahydro-1,2-benzisoxazole-3-carboxylic acid (ArtChem). MS (m/e)=360.3 [M+H$^+$].

Example 19

2-Chloro-N-(2-phenyl-imidazo[1,2-a]pyrimidin-7-yl)-isonicotinamide

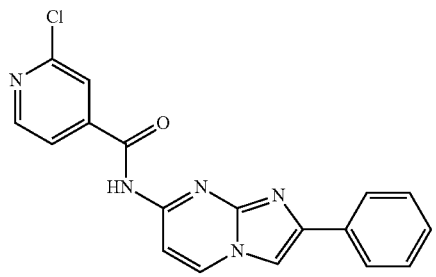 [SMILES: O=C(Nc1ccn2cc(-c3ccccc3)nc2n1)c1ccnc(Cl)c1]

The title compound was obtained in analogy to example 3 from 2-chloroisonicotinic acid. MS (m/e)=350.3 [M+H$^+$].

Example 20

4-Isoxazol-5-yl-2-methyl-2H-pyrazole-3-carboxylic acid (2-phenyl-imidazo[1,2-a]pyrimidin-7-yl)-amide

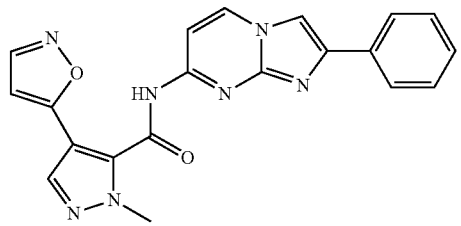 [SMILES: Cn1ncc(-c2ccno2)c1C(=O)Nc1ccn2cc(-c3ccccc3)nc2n1]

The title compound was obtained in analogy to example 3 from 4-(5-isoxazolyl)-1-methyl-1H-pyrazole-5-carboxylic acid. MS (m/e)=386.1 [M+H$^+$].

Example 21

6-Chloro-pyridine-2-carboxylic acid (2-phenyl-imidazo[1,2-a]pyrimidin-7-yl)-amide

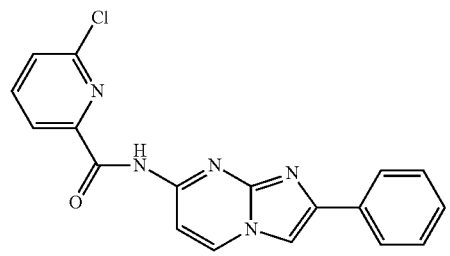 [SMILES: O=C(Nc1ccn2cc(-c3ccccc3)nc2n1)c1cccc(Cl)n1]

The title compound was obtained in analogy to example 3 from 6-chloropicolinic acid. MS (m/e)=350.1 [M+H$^+$].

Example 22

6-Methoxy-pyridine-2-carboxylic acid (2-phenyl-imidazo[1,2-a]pyrimidin-7-yl)-amide

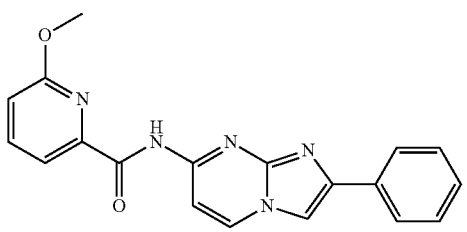 [SMILES: COc1cccc(C(=O)Nc2ccn3cc(-c4ccccc4)nc3n2)n1]

The title compound was obtained in analogy to example 3 from 6-methoxypicolinic acid. MS (m/e)=346.1 [M+H$^+$].

Example 23

5-Bromo-3-methyl-pyridine-2-carboxylic acid (2-phenyl-imidazo[1,2-a]pyrimidin-7-yl)-amide

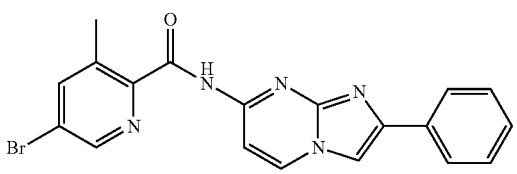 [SMILES: Cc1cc(Br)cnc1C(=O)Nc1ccn2cc(-c3ccccc3)nc2n1]

To an argon purged solution of 2-phenylimidazo[1,2-a]pyrimidin-7-amine (example 1, step 1, 80 mg, 0.381 mmol) in dioxane (5 ml) was added trimethyl aluminum solution (0.571 ml, 1.14 mmol, 3 eq). The resulting solution was stirred for 1 hour at RT. Then methyl 5-bromo-3-methylpicolinate (88 mg, 0.381 mmol) was added and the mixture was heated to reflux and stirred for 18 hours. The title compound (84 mg, 54%) was isolated from the crude product by flash chromatography on a 20 g SiO$_2$ column using dichloromethane/methanol 0-10% as eluent. MS (m/e)=408.2 [M+H$^+$].

Example 24

4-Bromo-3,6-dimethyl-pyridine-2-carboxylic acid (2-phenyl-imidazo[1,2-a]pyrimidin-7-yl)-amide

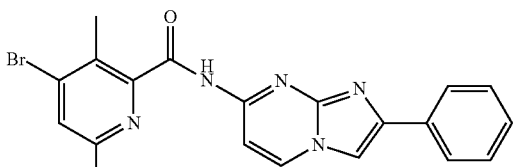

The title compound was obtained in analogy to example 23 from ethyl 4-bromo-3,6-dimethylpicolinate.

(Ethyl 4-bromo-3,6-dimethylpicolinate can be prepared by the method of G. Jaeschke, W. Spooren, E. Vieira, PCT Int. Appl. WO 2007093542.) MS (m/e)=424.0 [M+H⁺].

Example 25

6-Methyl-pyridine-2-carboxylic acid (2-phenyl-imidazo[1,2-a]pyrimidin-7-yl)-amide

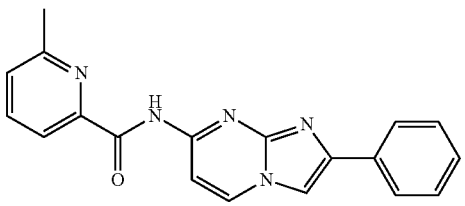 [SMILES: Cc1cccc(C(=O)Nc2ccn3cc(-c4ccccc4)nc3n2)n1]

The title compound was obtained in analogy to example 23 from ethyl 4-bromo-3,6-dimethylpicolinate. MS (m/e)=330.2 [M+H⁺].

Example 26

5-(2-Phenyl-imidazo[1,2-a]pyrimidin-7-ylcarbamoyl)-3H-[1,2,3]triazole-4-carboxylic acid methyl ester

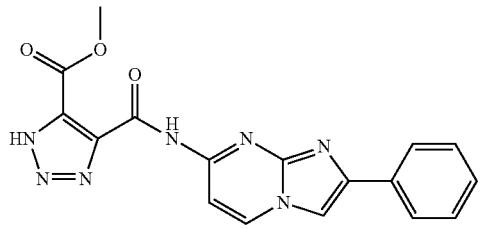 [SMILES: COC(=O)c1[nH]nnc1C(=O)Nc1ccn2cc(-c3ccccc3)nc2n1]

The title compound was obtained in analogy to example 3 from 1H-[1,2,3]triazole-4,5-dicarboxylic acid 5-methyl ester. (1H-[1,2,3]Triazole-4,5-dicarboxylic acid 5-methyl ester can be prepared by the method of J. Aszodi, M. Lampilas, B. Musicki, D. A. Rowlands, P. Collette, PCT Int. Appl. WO 2002100860.) MS (m/e)=364.1 [M+H⁺].

Example 27

5-(Azetidine-1-carbonyl)-1H-[1,2,3]triazole-4-carboxylic acid (2-phenyl-imidazo[1,2-a]pyrimidin-7-yl)-amide

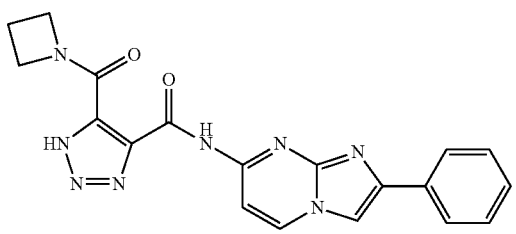 [SMILES: O=C(Nc1ccn2cc(-c3ccccc3)nc2n1)c1nn[nH]c1C(=O)N1CCC1]

Step 1: 5-(2-Phenyl-imidazo[1,2-a]pyrimidin-7-yl-carbamoyl)-3H-[1,2,3]triazole-4-carboxylic acid NaOH (3N, 1.47 ml) was added to a solution of 5-(2-phenyl-imidazo[1,2-a]pyrimidin-7-ylcarbamoyl)-3H-[1,2,3]triazole-4-carboxylic acid methyl ester (example 26, 800 mg, 2.2 mmol) in methanol/THF=1:1 (16 ml), and the mixture was stirred for 6 h at RT. The mixture was acidified (pH=3) with HCl (2N), the suspension was stirred for 15 min, and filtered. The precipitated title compound (590 mg, 77%) was dried under vacuum, and used in the next step without further purification.
MS (m/e)=348.3 [M–H⁺].

Step 2: 5-(Azetidine-1-carbonyl)-1H-[1,2,3]triazole-4-carboxylic acid (2-phenyl-imidazo[1,2-a]pyrimidin-7-yl)-amide Diisopropylethylamine (89 mg, 0.69 mmol) and TBTU (88 mg, 0.27 mmol) were added to a solution of 5-(2-phenyl-imidazo[1,2-a]pyrimidin-7-ylcarbamoyl)-3H-[1,2,3]triazole-4-carboxylic acid (80 mg, 0.23 mmol) in DMF (1 ml), and the dark brown solution was stirred for 30 min at RT. Azetidine (39 mg, 0.68 mmol) was added, and the mixture was stirred at RT overnight. The title compound (25 mg, 28%) was obtained from the reaction mixture by preparative HPLC (254 nm, Agilent Zorbax XdB-C18, Run: 7 min, Flow: 30 ml/min, Gradient: 0.0 min: 95/5 H₂O/CH₃CN; 0.5 min: 95/5 H₂O/CH₃CN 4.5 min: 5/95 H₂O/CH₃CN; 6.9 min 5/95 H₂O/CH₃CN; 7 min 95/5 H₂O/CH₃CN). MS (m/e)=389.3 [M+H⁺].

Example 28

1H-[1,2,3]Triazole-4,5-dicarboxylic acid 5-(ethyl-methyl-amide) 4-[(2-phenyl-imidazo[1,2-a]pyrimidin-7-yl)-amide]

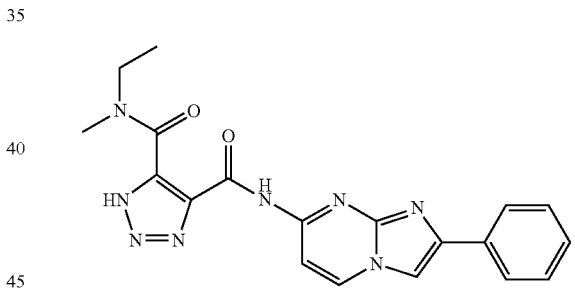

The title compound was obtained in analogy to example 27 from ethylmethylamine. MS (m/e)=391.2 [M+H⁺].

Example 29

4-(Azetidine-1-carbonyl)-2-methyl-2H-pyrazole-3-carboxylic acid (2-phenyl-imidazo[1,2-a]pyrimidin-7-yl)-amide

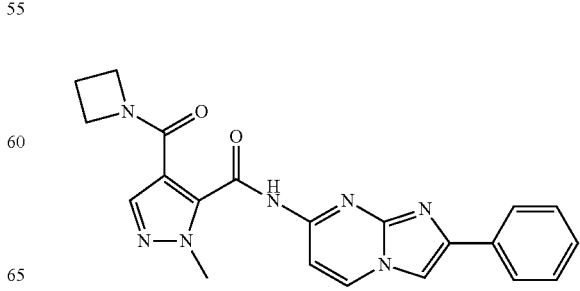

Step 1: 2-Methyl-2H-pyrazole-3,4-dicarboxylic acid diethyl ester

Under an atmosphere of argon, methylhydrazine (1.15 g, 25 mmol) and HCl (36.5% in water, 2.5 ml) were added to a solution of 2-dimethylaminomethylene-3-oxo-succinic acid diethyl ester (6.07 g, 25 mmol, obtained by the method of Hanzlowsky et al., *J. Heterocyclic Chem.* 2003, 40(3), 487-498) in ethanol (200 ml). The mixture was heated to 60° C. until HPLC analysis indicated the disappearance of the starting material (2 h). The solvent was evaporated, and the residue was taken up in dichloromethane and washed (water). The organic layer was dried ($Na_2SO_4$), the solvent was evaporated and the title compound (2.06 mg, 36%) was isolated from the mixture by column chromatography (silica gel, heptane:ethyl acetate=100:0-60:40). (The regioisomeric 1-methyl-1H-pyrazole-3,4-dicarboxylic acid diethyl ester can also be isolated, and can be distinguished from the desired product by NOE-$^1$H-NMR.) MS (m/e)=227.2 [M+H$^+$].

Step 2: 2-Methyl-2H-pyrazole-3,4-dicarboxylic acid 4-ethyl ester (This compound was prepared in close analogy to the method of Perez et al., Spanish patent appl. ES 493459.) 2-Methyl-2H-pyrazole-3,4-dicarboxylic acid diethyl ester (2.06 g, 9.1 mmol) was suspended in a NaOH solution (0.5M in water, 20 ml, 10 mmol) and heated to reflux (30 min). If the conversion was incomplete after this time, as indicated by HPLC control, small amounts of NaOH were added in 30 min intervals. The reaction mixture was cooled, and HCl was added, and stirred for an additional 30 min (r.t.). The precipitate was filtered, washed (water, small amount) and dried under vacuum. The title compound was obtained as a white solid (1.27 g, 70%), and was used in the next step without further purification. MS (m/e)=198 [M+H$^+$].

Step 3: 5-Chlorocarbonyl-1-methyl-1H-pyrazole-4-carboxylic acid ethyl ester

A mixture of 2-methyl-2H-pyrazole-3,4-dicarboxylic acid 4-ethyl ester (6.00 g) and thionyl chloride (82.8 g) was refluxed for 4 h. Excess thionyl chloride was removed under reduced pressure; the obtained crude product (7.26 g, assumed purity ~60%, 66%) was used in the next step without further purification.

Step 4: 1-Methyl-5-(2-phenyl-imidazo[1,2-a]pyrimidin-7-ylcarbamoyl)-1H-pyrazole-4-carboxylic acid ethyl ester 5-Chlorocarbonyl-1-methyl-1H-pyrazole-4-carboxylic acid ethyl ester (3.60 g, assumed purity 60%, 10 mmol) was added slowly to a cooled (0° C.) solution of 2-phenylimidazo[1,2-a]pyrimidin-7-amine (example 1, step 1, 2.52 g, 12 mmol) and triethylamine (2.02 g, 20 mmol) in dichloromethane (50 ml), and the suspension was stirred overnight at RT. The mixture was taken up in dichloromethane, and washed with water. The combined organic layers were dried ($Na_2SO_4$), filtered, and the solvent was evaporated under reduced pressure. The title compound (2.75 g, 71%) was isolated from the residue by column chromatography (silica gel, heptane:ethyl acetate=100:0-60:40). MS (m/e)=391.2 [M+H$^+$].

Step 5: 1-Methyl-5-(2-phenyl-imidazo[1,2-a]pyrimidin-7-ylcarbamoyl)-1H-pyrazole-4-carboxylic acid NaOH (3N, 6.9 ml) was added to a solution of 1-methyl-5-(2-phenyl-imidazo[1,2-a]pyrimidin-7-ylcarbamoyl)-1H-pyrazole-4-carboxylic acid ethyl ester (2.70 g, 6.9 mmol) in THF/ethanol=1:1 (40 ml), an mixture was stirred at RT overnight. Water (10 ml) and HCl (conc., approx. 3 ml) were added to the cooled (0° C.) mixture, until the mixture had a pH of 3. The suspension was stirred for 15 min, and filtered. The precipitate was washed with a small amount of water, and dried under vacuum. The thus obtained product (910 mg, 36%) was used in the next step without further purification. MS (m/e)=361.3 [M−H$^+$].

Step 6: 4-(Azetidine-1-carbonyl)-2-methyl-2H-pyrazole-3-carboxylic acid (2-phenyl-imidazo[1,2-a]pyrimidin-7-yl)-amide TBTU (213 mg, 0.66 mmol) and diisopropylethylamine (214 mg, 1.66 mmol) were added to a solution of 1-methyl-5-(2-phenyl-imidazo[1,2-a]pyrimidin-7-ylcarbamoyl)-1H-pyrazole-4-carboxylic acid (200 mg, 0.55 mmol) in DMF (2 ml), and the mixture was stirred for 30 min. Azetidine (95 mg, 1.66 mmol) was added, and the mixture was stirred at RT overnight. Water (6 ml) was added, and the suspension was stirred for 15 min at RT, and then filtered. The precipitate was suspended in a mixture of DMF (2 ml) and methanol (1 ml). The suspension was stirred for 15 min, and filtered. The obtained title compound was dried under vacuum.

MS (m/e)=402.4 [M+H$^+$].

Example 30

2-Methyl-4-(morpholine-4-carbonyl)-2H-pyrazole-3-carboxylic acid (2-phenyl-imidazo[1,2-a]pyrimidin-7-yl)-amide

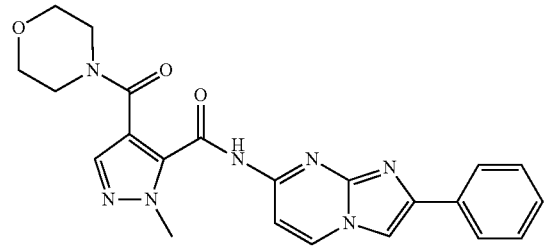 [SMILES: Cn1ncc(C(=O)N2CCOCC2)c1C(=O)Nc1ccn2cc(-c3ccccc3)nc2n1]

The title compound was obtained in analogy to example 29, using morpholine in the last step. MS (m/e)=432.3 [M+H$^+$].

Example 31

2-Methyl-2H-pyrazole-3,4-dicarboxylic acid 4-methylamide 3-[(2-phenyl-imidazo[1,2-a]pyrimidin-7-yl)-amide]

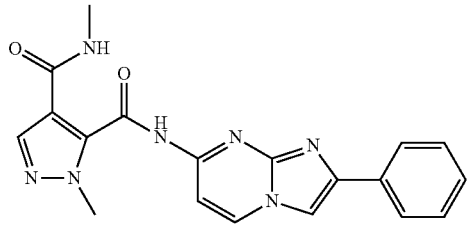 [SMILES: CNC(=O)c1cnn(C)c1C(=O)Nc1ccn2cc(-c3ccccc3)nc2n1]

Methylamine (2N in methanol, 1.54 ml, 3.1 mmol) was added to a solution of 1-methyl-5-(2-phenyl-imidazo[1,2-a]pyrimidin-7-ylcarbamoyl)-1H-pyrazole-4-carboxylic acid ethyl ester (example 29, Step 4, 100 mg, 0.26 mmol) in THF (1.5 ml), and the mixture was stirred over the weekend at RT. The solvent was evaporated, DMF (1.5 ml) was added to the residue, and the mixture was stirred for 5 min. The precipitated title compound (20 mg, 21%) was collected by filtration, and residual DMF was removed under vacuum. MS (m/e)=376.4 [M+H$^+$].

Example 32

2-Methyl-2H-pyrazole-3,4-dicarboxylic acid 3-{[2-(3-chloro-phenyl)-imidazo[1,2-a]pyrimidin-7-yl]-amide}4-methylamide

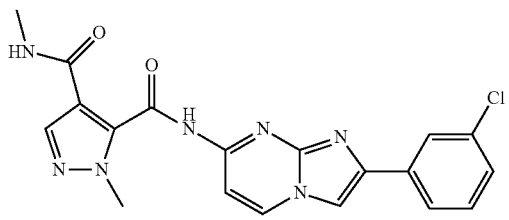 [SMILES: CNC(=O)c1cnn(C)c1C(=O)Nc1ccn2cc(-c3cccc(Cl)c3)nc2n1]

The title compound was prepared in analogy to example 31 from 5-[2-(3-chloro-phenyl)-imidazo[1,2-a]pyrimidin-7-ylcarbamoyl]-1-methyl-1H-pyrazole-4-carboxylic acid ethyl ester. 5-[2-(3-Chloro-phenyl)-imidazo[1,2-a]pyrimidin-7-ylcarbamoyl]-1-methyl-1H-pyrazole-4-carboxylic acid ethyl ester was prepared in analogy to example 29, using 2-(3-chloro-phenyl)-imidazo[1,2-a]pyrimidin-7-ylamine in step 4. 2-(3-Chloro-phenyl)-imidazo[1,2-a]pyrimidin-7-ylamine was prepared in analogy to example 1, step 1, from 2-bromo-1-(3-chloro-phenyl)-ethanone. MS (m/e)=410.2 [M+H$^+$].

Example 33

2-Methyl-2H-pyrazole-3,4-dicarboxylic acid 3-{[2-(4-fluoro-phenyl)-imidazo[1,2-a]pyrimidin-7-yl]amide}4-methylamide

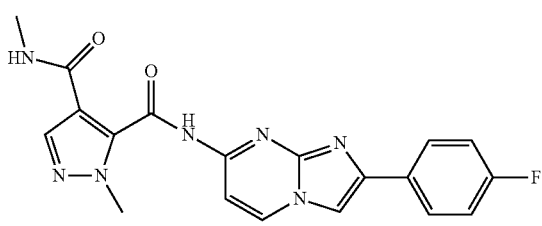 [SMILES: CNC(=O)c1cnn(C)c1C(=O)Nc1ccn2cc(-c3ccc(F)cc3)nc2n1]

The title compound was prepared in analogy to example 31 from 5-[2-(4-fluoro-phenyl)-imidazo[1,2-a]pyrimidin-7-ylcarbamoyl]-1-methyl-1H-pyrazole-4-carboxylic acid ethyl ester. 5-[2-(4-Fluoro-phenyl)-imidazo[1,2-a]pyrimidin-7-ylcarbamoyl]-1-methyl-1H-pyrazole-4-carboxylic acid ethyl ester was prepared in analogy to example 29, using 2-(4-fluoro-phenyl)-imidazo[1,2-a]pyrimidin-7-ylamine in step 4. 2-(4-Fluoro-phenyl)-imidazo[1,2-a]pyrimidin-7-ylamine was prepared in analogy to example 1, step 1, from 2-bromo-1-(4-fluoro-phenyl)-ethanone. MS (m/e)=394.1 [M+H$^+$].

Example 34

4-(3,3-Difluoro-azetidine-1-carbonyl)-2-methyl-2H-pyrazole-3-carboxylic acid (2-phenyl-imidazo[1,2-a]pyrimidin-7-yl)-amide

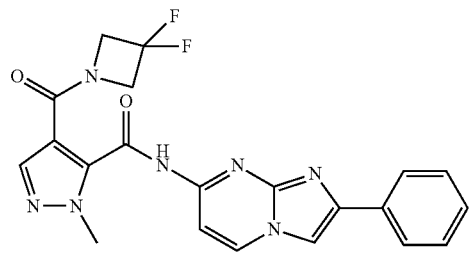 [SMILES: Cn1ncc(C(=O)N2CC(F)(F)C2)c1C(=O)Nc1ccn2cc(-c3ccccc3)nc2n1]

The title compound was obtained in analogy to example 29, using 3,3-difluoro-azetidine in the last step. MS (m/e)=438.3 [M+H$^+$].

Example 35

2-Methyl-2H-pyrazole-3,4-dicarboxylic acid 4-[(2-hydroxy-ethyl)-amide]3-[(2-phenyl-imidazo[1,2-a]pyrimidin-7-yl)-amide]

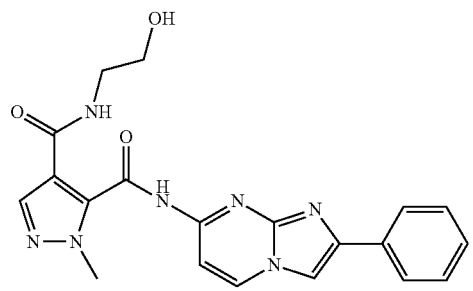 [SMILES: Cn1ncc(C(=O)NCCO)c1C(=O)Nc1ccn2cc(-c3ccccc3)nc2n1]

The title compound was obtained in analogy to example 29, using 2-amino-ethanol in the last step. MS (m/e)=406.4 [M+H$^+$].

Example 36

4-(3-Hydroxy-azetidine-1-carbonyl)-2-methyl-2H-pyrazole-3-carboxylic acid (2-phenyl-imidazo[1,2-a]pyrimidin-7-yl)-amide

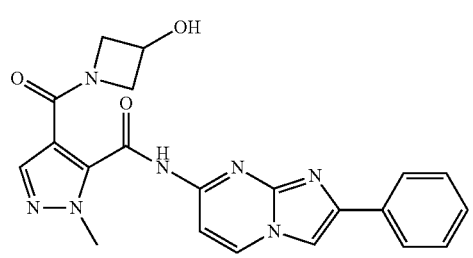 [SMILES: Cn1ncc(C(=O)N2CC(O)C2)c1C(=O)Nc1ccn2cc(-c3ccccc3)nc2n1]

The title compound was obtained in analogy to example 29, using azetidin-3-ol in the last step. MS (m/e)=418.3 [M+H$^+$].

Example 37

4-(1,1-Dioxo-1λ6-thiomorpholine-4-carbonyl)-2-methyl-2H-pyrazole-3-carboxylic acid (2-phenyl-imidazo[1,2-a]pyrimidin-7-yl)-amide

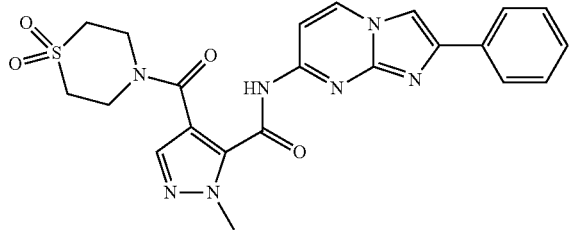 [SMILES: Cn1ncc(C(=O)N2CCS(=O)(=O)CC2)c1C(=O)Nc1ccn2cc(-c3ccccc3)nc2n1]

The title compound was obtained in analogy to example 29, using thiomorpholine 1,1-dioxide in the last step. MS (m/e)=480.2 [M+H$^+$].

Example 38

2-Methyl-2H-pyrazole-3,4-dicarboxylic acid 4-[(3-hydroxy-propyl)-amide]3-[(2-phenyl-imidazo[1,2-a]pyrimidin-7-yl-amide]

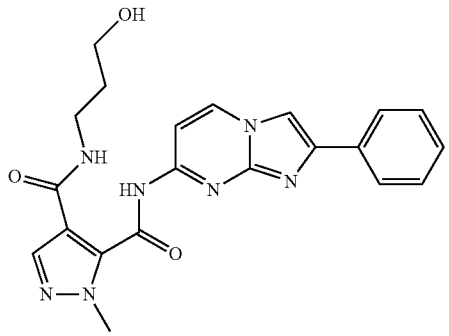 [SMILES: Cn1ncc(C(=O)NCCCO)c1C(=O)Nc1ccn2cc(-c3ccccc3)nc2n1]

The title compound was obtained in analogy to example 29, using 3-amino-propan-1-ol in the last step. MS (m/e)=420.2 [M+H$^+$].

Example 39

2-Methyl-2H-pyrazole-3,4-dicarboxylic acid 4-[(3-methoxy-propyl)-amide]3-[(2-phenyl-imidazo[1,2-a]pyrimidin-7-yl)-amide]

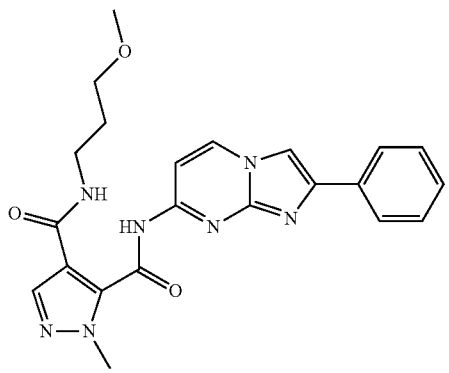 [SMILES: COCCCNC(=O)c1cnn(C)c1C(=O)Nc1ccn2cc(-c3ccccc3)nc2n1]

The title compound was obtained in analogy to example 29, using 3-methoxy-propylamine in the last step. MS (m/e)=434.3 [M+H$^+$].

Example 40

2-Methyl-2H-pyrazole-3,4-dicarboxylic acid 3-[(2-phenyl-imidazo[1,2-a]pyrimidin-7-yl)-amide]-4-[(tetrahydro-furan-3-yl)-amide]

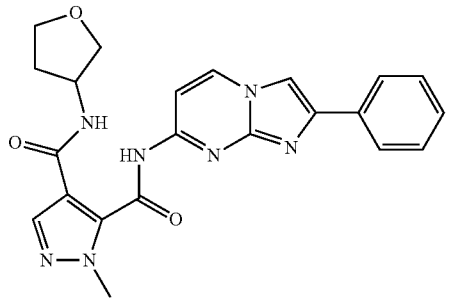 [SMILES: Cn1ncc(C(=O)NC2CCOC2)c1C(=O)Nc1ccn2cc(-c3ccccc3)nc2n1]

The title compound was obtained in analogy to example 29, using tetrahydro-furan-3-ylamine in the last step. MS (m/e)=432.3 [M+H$^+$].

Example 41

2-Methyl-2H-pyrazole-3,4-dicarboxylic acid 4-[(2-hydroxy-1-methyl-ethyl)-amide]3-[(2-phenyl-imidazo[1,2-a]pyrimidin-7-yl)-amide]

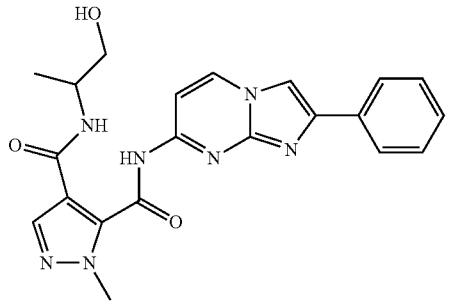 [SMILES: CC(CO)NC(=O)c1cnn(C)c1C(=O)Nc1ccn2cc(-c3ccccc3)nc2n1]

The title compound was obtained in analogy to example 29, using 2-amino-propan-1-ol in the last step. MS (m/e)=420.1 [M+H$^+$].

Example 42

2-Methyl-2H-pyrazole-3,4-dicarboxylic acid 4-[(2-hydroxy-propyl)-amide]3-[(2-phenyl-imidazo[1,2-a]pyrimidin-7-yl)-amide]

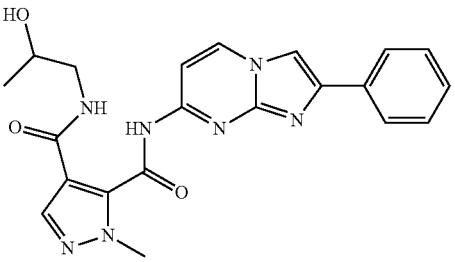 [SMILES: CC(O)CNC(=O)c1cnn(C)c1C(=O)Nc1ccn2cc(-c3ccccc3)nc2n1]

The title compound was obtained in analogy to example 29, using 1-amino-propan-2-ol in the last step. MS (m/e)=420.2 [M+H$^+$].

Example 43

Pyrazine-2,3-dicarboxylic acid 2-[(2-phenyl-imidazo[1,2-a]pyrimidin-7-yl)-amide]3-[(2,2,2-trifluoro-ethyl)-amide]

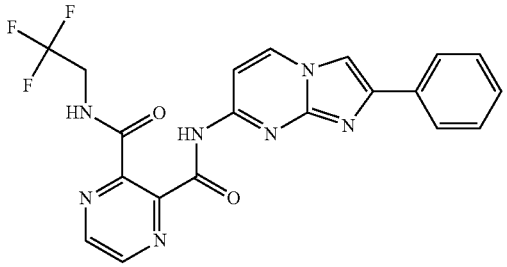 [SMILES: O=C(NCC(F)(F)F)c1nccnc1C(=O)Nc1ccn2cc(-c3ccccc3)nc2n1]

Step 1: 3-(2-Phenyl-imidazo[1,2-a]pyrimidin-7-yl-carbamoyl)-pyrazine-2-carboxylic acid Furo[3,4-b]pyrazine-5,7-dione (736 mg, 4.9 mmol) and DMAP (58 mg, cat.) were added to a solution of 2-phenyl-imidazo[1,2-a]pyrimidin-7-ylamine (example 1, step 1, 1.00 g, 4.8 mmol) in DMF (25 ml). The mixture was heated to 78° C. overnight, and cooled to RT. The formed precipitate was collected by filtration, and residual solvent was removed under vacuum. The thus obtained crude product (800 mg, 47%) was used in the next step without further purification. MS (m/e)=361.3 [M+H$^+$].

Step 2: Pyrazine-2,3-dicarboxylic acid 2-[(2-phenyl-imidazo[1,2-a]pyrimidin-7-yl)-amide]3-[(2,2,2-trifluoro-ethyl)-amide]

In a sealable tube, TBTU (75 mg, 0.23 mmol), 3-(2-phenyl-imidazo[1,2-a]pyrimidin-7-ylcarbamoyl)-pyrazine-2-carboxylic acid (70 mg, 0.19 mmol), and diisopropylethylamine (75 mg, 0.58 mmol) were dissolved in DMF (2 ml) and shaken for 1 h at RT. Trifluoroethylamine (23 mg, 0.23 mmol) was then added, and the mixture was shaken at RT overnight. The title compound was isolated from the reaction mixture by preparative HPLC (254 nm, Agilent Zorbax XdB-C18, Run: 7 min, Flow: 30 ml/min, Gradient: 0.0 min: 95/5 H$_2$O/CH$_3$CN; 0.5 min: 95/5 H$_2$O/CH$_3$CN 4.5 min: 5/95 H$_2$O/CH$_3$CN; 6.9 min 5/95 H$_2$O/CH$_3$CN; 7 min 95/5 H$_2$O/CH$_3$CN).
MS (m/e)=442.2 [M+H$^+$].

Example 44

2-(Azetidine-1-carbonyl)-N-(2-phenyl-imidazo[1,2-a]pyrimidin-7-yl)-nicotinamide

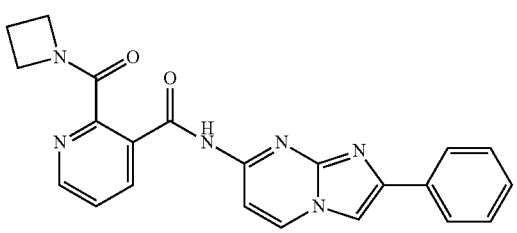 [SMILES: O=C(Nc1ccn2cc(-c3ccccc3)nc2n1)c1cccnc1C(=O)N1CCC1]

Step 1: 3-Chlorocarbonyl-pyridine-2-carboxylic acid methyl ester

Pyridine-2,3-dicarboxylic acid 2-methyl ester (500 mg, 2.76 mmol) was dissolved in thionyl chloride (8.21 g, 68 mmol) and heated to reflux for 4 h. Excess thionyl chloride was removed under vacuum. The obtained crude product (620 mg, assumed purity 60%, 68% yield) was used in the next step without further purification.

Step 2: 3-[(2-Phenyl-imidazo[1,2-a]pyrimidin-7-yl)-(pyridine-2-[carboxylic acid methyl ester]-3-carbonyl)-carbamoyl]pyridine-2-carboxylic acid methyl ester 3-Chlorocarbonyl-pyridine-2-carboxylic acid methyl ester (620 mg, 3.1 mmol) was added slowly to a solution of 2-phenyl-imidazo[1,2-a]pyrimidin-7-ylamine (step 1, example 1, 470 mg, 2.2 mmol) and triethylamine (566 mg) in dichloromethane (7 ml), and the mixture was stirred overnight at RT. The mixture was diluted with additional dichloromethane, and washed with water. The combined organic layers were dried (Na$_2$SO$_4$), the solvent was evaporated, and the title compound (490 mg, 49%) was obtained from the residue by column chromatography (silica gel, dichloromethane:methanol=50:50-0:100). MS (m/e)=374.2 [M+H$^+$].

Step 3: 3-(2-Phenyl-imidazo[1,2-a]pyrimidin-7-yl-carbamoyl)-pyridine-2-carboxylic acid NaOH (3N, 2.2 ml, 6.6 mmol) was added to a solution of 3-[(2-phenyl-imidazo[1,2-a]pyrimidin-7-yl)-(pyridine-2-[carboxylic acid methyl ester]-3-carbonyl)-carbamoyl]-pyridine-2-carboxylic acid methyl ester (1.18 g, 2.2 mmol) in methanol/THF=1:1, and the mixture was stirred for 5 h at RT. The mixture was acidified to pH=3 by addition of HCl (conc.), and the volatile solvents were evaporated under reduced pressure. Water was added to the obtained suspension, and the mixture was stirred for 15 min at RT. The precipitate was collected by filtration, washed with water, and dried under vacuum. The thus obtained product (290 mg, 37%) was used in the next step without further purification. MS (m/e)=358.3 [M−H$^+$].

Step 4: 2-(Azetidine-1-carbonyl)-N-(2-phenyl-imidazo[1,2-a]pyrimidin-7-yl)-nicotinamide TBTU (107 mg, 0.33 mmol), 3-(2-phenyl-imidazo[1,2-a]pyrimidin-7-ylcarbamoyl)-pyridine-2-carboxylic acid (70 mg, 0.19 mmol), and diisopropylethylamine (108 mg, 0.3 mmol) were dissolved in DMF (1 ml) and shaken for 30 min at RT. Azetidine (48 mg, 0.84 mmol) was then added, and the mixture was shaken at RT overnight. The title compound (9 mg, 8%) was isolated from the reaction mixture by preparative HPLC (254 nm, Agilent Zorbax XdB-C18, Run: 7 min, Flow: 30 ml/min, Gradient: 0.0 min: 95/5 H$_2$O/CH$_3$CN; 0.5 min: 95/5 H$_2$O/CH$_3$CN 4.5 min: 5/95 H$_2$O/CH$_3$CN; 6.9 min 5/95 H$_2$O/CH$_3$CN; 7 min 95/5 H$_2$O/CH$_3$CN).
MS (m/e)=399.2 [M+H$^+$].

Example 45

4-(Azetidine-1-carbonyl)-2-methyl-2H-pyrazole-3-carboxylic acid [2-(3-methoxy-phenyl)-imidazo[1,2-a]pyrimidin-7-yl]-amide

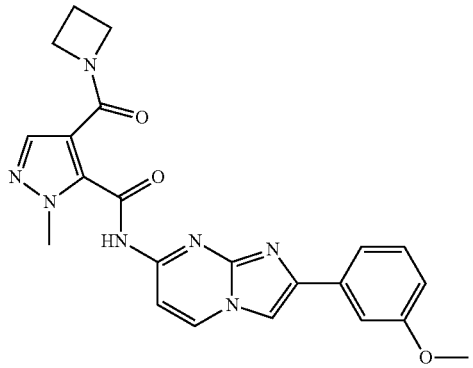 [SMILES: COc1cccc(-c2cn3ccc(NC(=O)c4c(C(=O)N5CCC5)cnn4C)nc3n2)c1]

The title compound was prepared in analogy to example 29, using 2-(3-methoxy-phenyl)-imidazo[1,2-a]pyrimidin-7-ylamine in the first step. 2-(3-Methoxy-phenyl)-imidazo[1,2-a]pyrimidin-7-ylamine can be prepared in analogy to example 1, step 1, from 2-bromo-1-(3-methoxy-phenyl)-ethanone. MS (m/e)=432.2 [M+H$^+$].

Example 46

2-Methyl-2H-pyrazole-3,4-dicarboxylic acid 4-[(2-methoxy-ethyl)-amide]3-[(2-phenyl-imidazo[1,2-a]pyrimidin-7-yl)-amide]

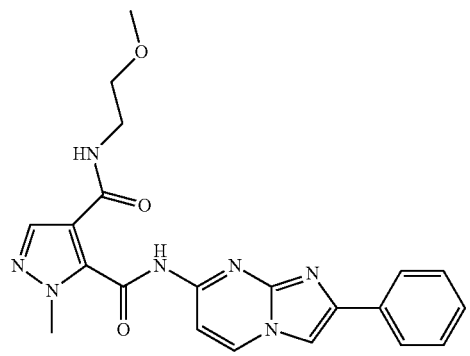 [SMILES: COCCNC(=O)c1cnn(C)c1C(=O)Nc1ccn2cc(-c3ccccc3)nc2n1]

The title compound was obtained in analogy to example 29, using 2-methoxy-ethylamine in the last step. MS (m/e)=420.2 [M+H$^+$].

Example 47

2-Methyl-2H-pyrazole-3,4-dicarboxylic acid 4-diethylamide 3-[(2-phenyl-imidazo[1,2-a]pyrimidin-7-yl)-amide]

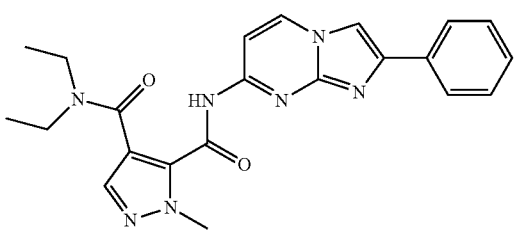 [SMILES: CCN(CC)C(=O)c1cnn(C)c1C(=O)Nc1ccn2cc(-c3ccccc3)nc2n1]

The title compound was obtained in analogy to example 29, using diethylamine in the last step. MS (m/e)=418.3 [M+H$^+$].

Example 48

2-Methyl-4-(pyrrolidine-1-carbonyl)-2H-pyrazole-3-carboxylic acid (2-phenyl-imidazo[1,2-a]pyrimidin-7-yl)-amide

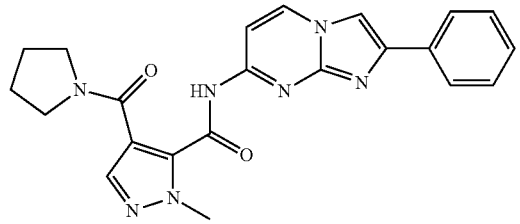 [SMILES: Cn1ncc(C(=O)N2CCCC2)c1C(=O)Nc1ccn2cc(-c3ccccc3)nc2n1]

The title compound was obtained in analogy to example 29, using pyrrolidine in the last step. MS (m/e)=416.3 [M+H$^+$].

Example 49

2-Methyl-2H-pyrazole-3,4-dicarboxylic acid 4-(ethyl-methyl-amide) 3-[(2-phenyl-imidazo[1,2-a]pyrimidin-7-yl)-amide]

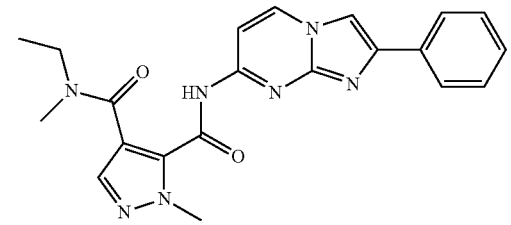 [SMILES: CCN(C)C(=O)c1cnn(C)c1C(=O)Nc1ccn2cc(-c3ccccc3)nc2n1]

The title compound was obtained in analogy to example 29, using ethylmethylamine in the last step. MS (m/e)=404.4 [M+H$^+$].

Example 50

2-Methyl-2H-pyrazole-3,4-dicarboxylic acid 4-ethylamide 3-[(2-phenyl-imidazo[1,2-a]pyrimidin-7-yl)-amide]

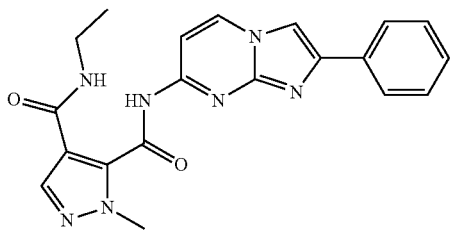 [SMILES: CCNC(=O)c1cnn(C)c1C(=O)Nc1ccn2cc(-c3ccccc3)nc2n1]

The title compound was obtained in analogy to example 29, using ethylamine in the last step. MS (m/e)=390.3 [M+H⁺].

Example 51

2-Methyl-2H-pyrazole-3,4-dicarboxylic acid 4-cyclopropylamide 3-[(2-phenyl-imidazo[1,2-a]pyrimidin-7-yl)-amide]

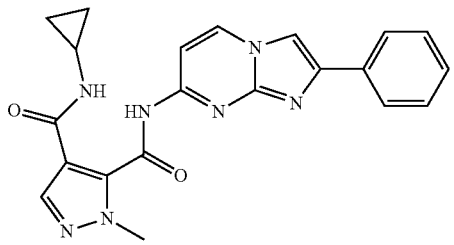 [SMILES: Cn1ncc(C(=O)NC2CC2)c1C(=O)Nc1ccn2cc(-c3ccccc3)nc2n1]

The title compound was obtained in analogy to example 29, using cyclopropylamine in the last step. MS (m/e)=402.4 [M+H⁺].

Example 52

2-Methyl-4-(piperidine-1-carbonyl)-2H-pyrazole-3-carboxylic acid (2-phenyl-imidazo[1,2-a]pyrimidin-7-yl)-amide

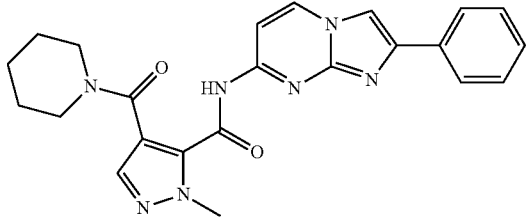 [SMILES: Cn1ncc(C(=O)N2CCCCC2)c1C(=O)Nc1ccn2cc(-c3ccccc3)nc2n1]

The title compound was obtained in analogy to example 29, using piperidine in the last step. MS (m/e)=430.4 [M+H⁺].

Example 53

2-Methyl-2H-pyrazole-3,4-dicarboxylic acid 4-[(2-hydroxy-ethyl)-methyl-amide]3-[(2-phenyl-imidazo[1,2-a]pyrimidin-7-yl)-amide]

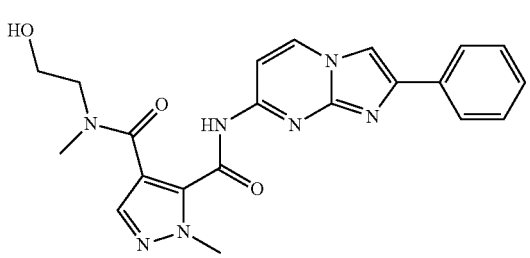 [SMILES: CN(CCO)C(=O)c1cnn(C)c1C(=O)Nc1ccn2cc(-c3ccccc3)nc2n1]

The title compound was obtained in analogy to example 29, using 2-methylamino-ethanol in the last step. MS (m/e)=420.2 [M+H⁺].

Example 54

2-Methyl-2H-pyrazole-3,4-dicarboxylic acid 4-(isopropyl-methyl-amide) 3-[(2-phenyl-imidazo[1,2-a]pyrimidin-7-yl)-amide]

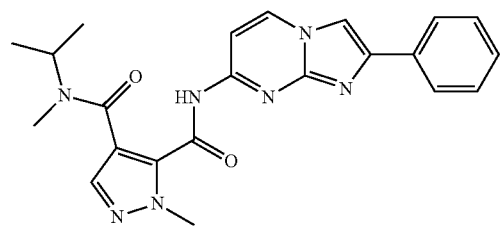 [SMILES: CC(C)N(C)C(=O)c1cnn(C)c1C(=O)Nc1ccn2cc(-c3ccccc3)nc2n1]

The title compound was obtained in analogy to example 29, using isopropyl-methyl-amine in the last step. MS (m/e)=418.3 [M+H⁺].

Example 55

2-Methyl-2H-pyrazole-3,4-dicarboxylic acid 4-[(2-methoxy-ethyl)-methyl-amide]3-[(2-phenyl-imidazo[1,2-a]pyrimidin-7-yl)-amide]

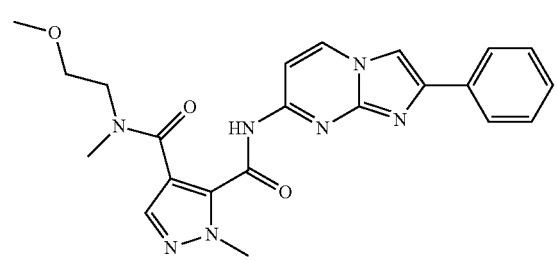 [SMILES: COCCN(C)C(=O)c1cnn(C)c1C(=O)Nc1ccn2cc(-c3ccccc3)nc2n1]

The title compound was obtained in analogy to example 29, using (2-methoxy-ethyl)-methyl-amine in the last step. MS (m/e)=434.4 [M+H⁺].

Example 56

2-Methyl-2H-pyrazole-3,4-dicarboxylic acid 4-(methyl-propyl-amide) 3-[(2-phenyl-imidazo[1,2-a]pyrimidin-7-yl)-amide]

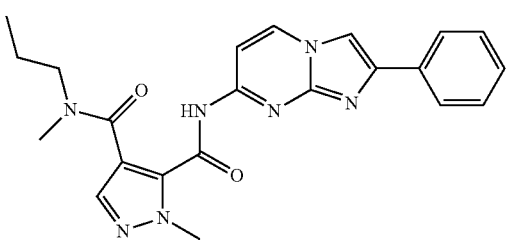 [SMILES: CCCN(C)C(=O)c1cnn(C)c1C(=O)Nc1ccn2cc(-c3ccccc3)nc2n1]

The title compound was obtained in analogy to example 29, using methyl-propyl-amine in the last step. MS (m/e)=418.3 [M+H⁺].

Example 57

2-Methyl-2H-pyrazole-3,4-dicarboxylic acid 3-[(2-phenyl-imidazo[1,2-a]pyrimidin-7-yl)-amide]-4-propylamide

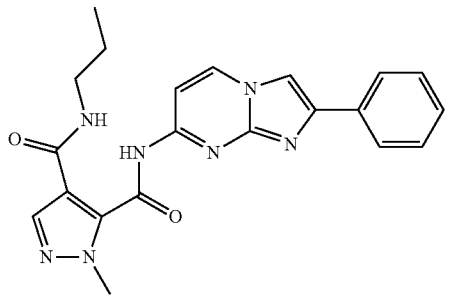 [SMILES: CCCNC(=O)c1cnn(C)c1C(=O)Nc1ccn2cc(-c3ccccc3)nc2n1]

The title compound was obtained in analogy to example 29, using propylamine in the last step. MS (m/e)=404.4 [M+H$^+$].

Example 58

2-Methyl-2H-pyrazole-3,4-dicarboxylic acid 4-cyclopropylmethyl-amide 3-[(2-phenyl-imidazo[1,2-a]pyrimidin-7-yl)-amide]

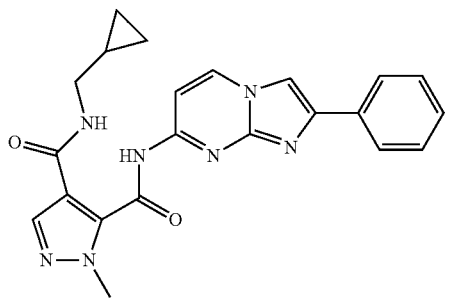 [SMILES: Cn1ncc(C(=O)NCC2CC2)c1C(=O)Nc1ccn2cc(-c3ccccc3)nc2n1]

The title compound was obtained in analogy to example 29, using cyclopropylmethylamine in the last step. MS (m/e)=416.4 [M+H$^+$].

Example 59

2-Methyl-2H-pyrazole-3,4-dicarboxylic acid 4-cyclobutylamide 3-[(2-phenyl-imidazo[1,2-a]pyrimidin-7-yl)-amide]

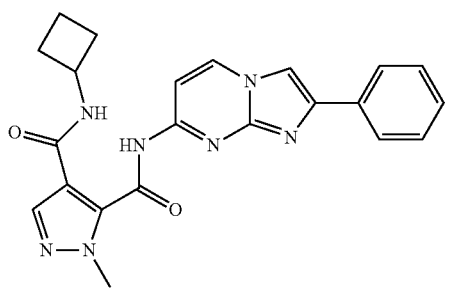 [SMILES: Cn1ncc(C(=O)NC2CCC2)c1C(=O)Nc1ccn2cc(-c3ccccc3)nc2n1]

The title compound was obtained in analogy to example 29, using cyclobutylamine in the last step. MS (m/e)=416.4 [M+H$^+$].

Example 60

2-Methyl-2H-pyrazole-3,4-dicarboxylic acid 4-isopropylamide 3-[(2-phenyl-imidazo[1,2-a]pyrimidin-7-yl)-amide]

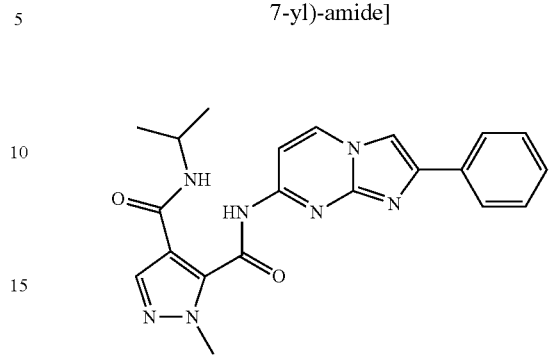

The title compound was obtained in analogy to example 29, using isopropylamine in the last step. MS (m/e)=404.4 [M+H$^+$].

Example 61

4-(Azetidine-1-carbonyl)-2-methyl-2H-pyrazole-3-carboxylic acid [2-(3-trifluoromethoxy-phenyl)-imidazo[1,2-a]pyrimidin-7-yl]-amide

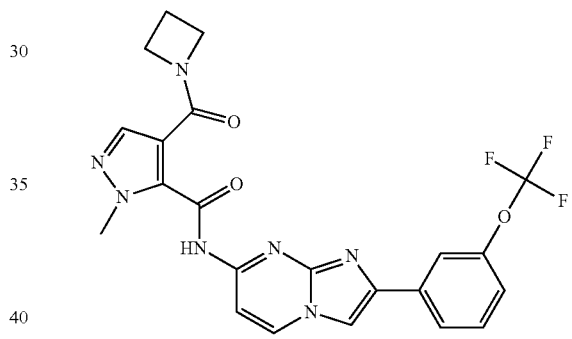

The title compound was prepared in analogy to example 29, using 2-(3-trifluoromethoxy-phenyl)-imidazo[1,2-a]pyrimidin-7-ylamine. 2-(3-Trifluoromethoxy-phenyl)-imidazo[1,2-a]pyrimidin-7-ylamine can be prepared in analogy to example 1, step 1, from 2-bromo-1-(3-trifluoromethoxy-phenyl)-ethanone. MS (m/e)=486.3 [M+H$^+$].

Example 62

1-Ethyl-5-(2-phenyl-imidazo[1,2-a]pyrimidin-7-ylcarbamoyl)-1H-pyrazole-4-carboxylic acid ethyl ester

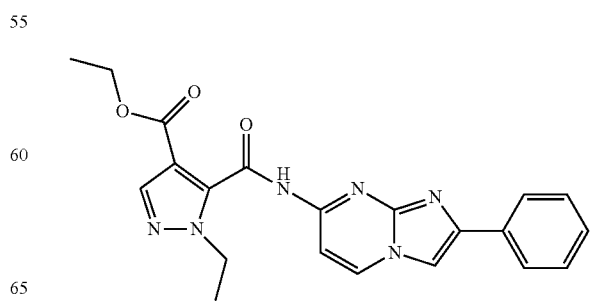

Step 1: 2H-Pyrazole-3,4-dicarboxylic acid diethyl ester

Under an atmosphere of argon, hydrazine monohydrate hydrochloride (1.91 g, 28 mmol) and HCl (36.5% in water, 2.8 ml) were added to a solution of 2-dimethylaminomethylene-3-oxo-succinic acid diethyl ester (6.8 g, 28 mmol) in ethanol (100 ml). The mixture was heated to 60° C. (3 h). The solvent was evaporated, and the residue was taken up in dichloromethane and washed (water). The organic layer was dried (Na$_2$SO$_4$), the solvent was evaporated and the title compound (1.81 mg, 31%) was isolated from the mixture by column chromatography (silica gel, heptane:ethyl acetate=100:0-60:40). MS (m/e)=383.3 [M+H$^+$].

Step 2: 2-Ethyl-2H-pyrazole-3,4-dicarboxylic acid diethyl ester

Sodium ethanolate solution was freshly prepared by dissolving sodium (240 mg) in ethanol (30 ml). 2H-Pyrazole-3,4-dicarboxylic acid diethyl ester (800 mg, 3.77 mmol) was dissolved in this sodium ethanolate solution (11 ml) and stirred for 10 min at RT, before ethyl iodide (1.4 g, 9 mmol) was added dropwise. After the completion of the addition, the mixture was heated to reflux until all starting material was consumed (1 h). The solvent was then evaporated, the residue was taken up in ethyl acetate and washed (water). The organic layer was dried (Na$_2$SO$_4$), evaporated, and the title compound (280 mg, 31%) was isolated from the mixture by column chromatography (silica gel, heptane:ethyl acetate=100:0-60:40). (The regioisomeric 1-ethyl-1H-pyrazole-3,4-dicarboxylic acid diethyl ester can also be isolated, and can be distinguished from the desired product by NOE-'H-NMR.)
MS (m/e)=241.1 [M+H$^+$].

Step 3: 2-Ethyl-2H-pyrazole-3,4-dicarboxylic acid 4-ethyl ester

2-Ethyl-2H-pyrazole-3,4-dicarboxylic acid diethyl ester (280 mg, 1.2 mmol) was suspended in a NaOH solution (0.5 M in water, 2.8 ml) and stirred at RT until HPLC analysis indicated the consumption of the starting material (4 h). HCl (1 N, 1 ml) was added, and the mixture was extracted with ethyl acetate. The combined organic layers were dried (Na$_2$SO$_4$), evaporated, and the title compound (200 mg, 81%) was isolated from the mixture by column chromatography (silica gel, heptane:ethyl acetate=100:0-60:40). MS (m/e)=211.1 [M–H$^+$].

Step 4: 1-Ethyl-5-(2-phenyl-imidazo[1,2-a]pyrimidin-7-ylcarbamoyl)-1H-pyrazole-4-carboxylic acid ethyl ester TBTU (1.1 g) and diisopropylethylamine (1.1 g) were added to a solution of 2-ethyl-2H-pyrazole-3,4-dicarboxylic acid 4-ethyl ester (610 mg) in DMF (7 ml), and the mixture was stirred for 30 min at RT. 2-Phenyl-imidazo[1,2-a]pyrimidin-7-ylamine (example 1, step 1, 725 mg) was added to the light yellow solution, and the mixture was stirred over the weekend at RT. Water (15 ml) was added, and the mixture was stirred for an additional 15 min. For purification, the precipitate was suspended in DMF (5 ml) and water (10 ml), and filtered; this process was repeated 4 times. The thus obtained title compound (150 mg, 13%) was dried under vacuum.
MS (m/e)=405.4 [M+H$^+$].

Example 63

4-(Azetidine-1-carbonyl)-2-methyl-2H-pyrazole-3-carboxylic acid [2-(3-chloro-phenyl)-imidazo[1,2-a]pyrimidin-7-yl]-amide

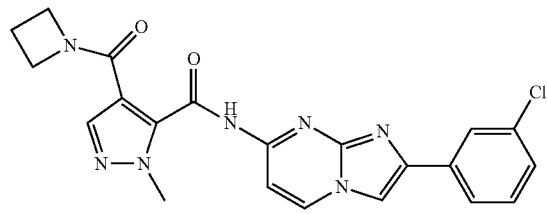 [SMILES: Cn1ncc(C(=O)N2CCC2)c1C(=O)Nc1ccn2cc(-c3cccc(Cl)c3)nc2n1]

The title compound was prepared in analogy to example 29, using 2-(3-chloro-phenyl)-imidazo[1,2-a]pyrimidin-7-ylamine in the first step. 2-(3-Chloro-phenyl)-imidazo[1,2-a]pyrimidin-7-ylamine can be prepared in analogy to example 1, step 1, from 2-Bromo-1-(3-chloro-phenyl)-ethanone. MS (m/e)=436.2 [M+H$^+$].

Example 64

2-Ethyl-2H-pyrazole-3,4-dicarboxylic acid 4-methylamide 3-[(2-phenyl-imidazo[1,2-a]pyrimidin-7-yl)-amide]

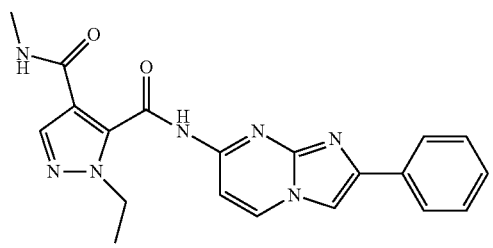 [SMILES: CCn1ncc(C(=O)NC)c1C(=O)Nc1ccn2cc(-c3ccccc3)nc2n1]

Step 1: Ethyl 5-(chlorocarbonyl)-1-ethyl-1H-pyrazole-4-carboxylate

2-Ethyl-2H-pyrazole-3,4-dicarboxylic acid 4-ethyl ester (example 62, step 3, 1.47 g, 6.93 mmol) and thionyl chloride (19.0 g, 11.6 ml, 159 mmol) were combined to give a light yellow solution. The reaction mixture was stirred at reflux for 5 h. Excess thionyl chloride was removed under reduced pressure, and residual thionyl chloride was removed under vacuum. The title compound (1.6 g, estimated purity 37%, 37% yield) was used without further purification in the next step. MS (m/e)=390.3 [M+H$^+$].

Step 2: Ethyl 1-ethyl-5-(2-phenylimidazo[1,2-a]pyrimidin-7-ylcarbamoyl)-1H-pyrazole-4-carboxylate 2-Phenylimidazo[1,2-a]pyrimidin-7-amine (example 1, step 1, 648 mg, 3.08 mmol) and triethylamine (519 mg, 715 µA, 5.13 mmol) were combined with dichloromethane (15 ml) to give a light brown solution. Ethyl 5-(chlorocarbonyl)-1-ethyl-1H-pyrazole-4-carboxylate (1.6 g, 2.57 mmol) was diluted in dichloromethan and was added dropwise at 0° C. The reaction was stirred overnight. The reaction mixture was poured into 20 mL water and extracted with dichloromethan (2×50 mL). The organic layers were dried over Na$_2$SO$_4$ and concentrated in vacuo. The crude material was purified by flash chromatography (silica gel, 50 g, 50% to 100% EtOAc in heptane). The obtained product contained the imide (2 acid chlorides added to amine) as an impurity, but was used in the next step (where the title compound and the impurity give the same product). The title compound was obtained as a light brown solid (510 mg, 49.1%).

MS (m/e)=405.4 [M+H$^+$].

Step 3: 2-Ethyl-2H-pyrazole-3,4-dicarboxylic acid 4-methylamide 3-[(2-phenyl-imidazo[1,2-a]pyrimidin-7-yl)-amide]

Methylamine (2N solution in methanol, 0.61 ml) was added to a solution of ethyl 1-ethyl-5-(2-phenylimidazo[1,2-a]pyrimidin-7-ylcarbamoyl)-1H-pyrazole-4-carboxylate (33 mg) in THF (0.6 ml), and the mixture was stirred at RT overnight. The solvent was evaporated, and the title compound (16 mg, 50%) was isolated from the residue by preparative HPLC (254 nm, Agilent Zorbax XdB-C18, Run: 7 min, Flow: 30 ml/min, Gradient: 0.0 min: 95/5 H$_2$O/CH$_3$CN; 0.5 min: 95/5 H$_2$O/CH$_3$CN 4.5 min: 5/95 H$_2$O/CH$_3$CN; 6.9 min 5/95 H$_2$O/CH$_3$CN; 7 min 95/5 H$_2$O/CH$_3$CN). MS (m/e)=390.3 [M+H$^+$].

Example 65

1H-[1,2,3]Triazole-4,5-dicarboxylic acid 5-methylamide 4-[(2-phenyl-imidazo[1,2-a]pyrimidin-7-yl)-amide]

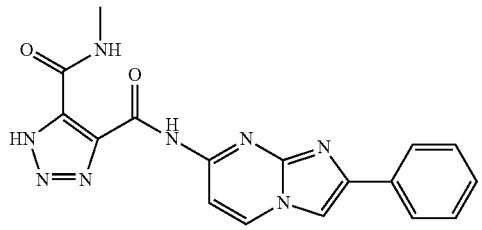 [SMILES: CNC(=O)c1[nH]nnc1C(=O)Nc1ccn2cc(-c3ccccc3)nc2n1]

The title compound was obtained in analogy to example 31 from 5-(2-phenyl-imidazo[1,2-a]pyrimidin-7-ylcarbamoyl)-3H-[1,2,3]triazole-4-carboxylic acid methyl ester (example 26). MS (m/e)=363.2 [M+H$^+$].

Example 66

3-(Azetidine-1-carbonyl)-1-methyl-1H-pyrazole-4-carboxylic acid (2-phenyl-imidazo[1,2-a]pyrimidin-7-yl)-amide

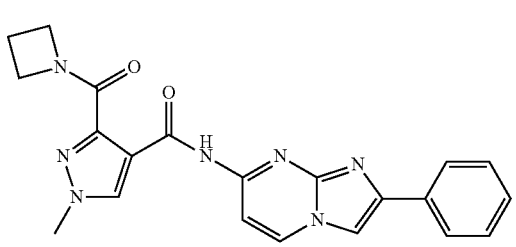 [SMILES: Cn1cc(C(=O)Nc2ccn3cc(-c4ccccc4)nc3n2)c(C(=O)N2CCC2)n1]

Step 1: 1-Methyl-4-(2-phenyl-imidazo[1,2-a]pyrimidin-7-ylcarbamoyl)-1H-pyrazole-3-carboxylic acid ethyl ester At 0° C., propylphosphonic acid anhydride (1-propanephosphonic acid cyclic anhydride, 50% in ethyl acetate, 7.4 ml, 2.5 eq.) was added slowly to a solution of 2-phenylimidazo[1,2-a]pyrimidin-7-amine (example 1, step 1, 1.27 g, 6 mmol), 1-methyl-1H-pyrazole-3,4-dicarboxylic acid 3-ethyl ester (1.00 g, 5 mmol), and ethyldiisopropylethylamine (2.0 ml, 15 mmol) in ethyl acetate (20 ml). The mixture was stirred for 30 min at 0° C., and subsequently at RT for 48 h. The mixture was taken up in ethyl acetate, and washed with water. The combined water layers were adjusted to pH=9 (NaOH), and extracted with dichloromethane. All organic layers were combined, dried (Na$_2$SO$_4$), and evaporated. The title compound (580 mg, 29%) was obtained from the residue by column chromatography (silica gel, heptane:ethyl acetate=100:0-80:20). (1-Methyl-1H-pyrazole-3,4-dicarboxylic acid 3-ethyl ester was obtained by the method of Pérez et al., Spanish patent appl. ES 493459.)

MS (m/e)=391.2 [M+H$^+$].

Step 2: 1-Methyl-4-(2-phenyl-imidazo[1,2-a]pyrimidin-7-ylcarbamoyl)-1H-pyrazole-3-carboxylic acid NaOH (3N, 1.5 ml) was added to a solution of 1-methyl-4-(2-phenyl-imidazo[1,2-a]pyrimidin-7-ylcarbamoyl)-1H-pyrazole-3-carboxylic acid ethyl ester (390 mg, 1.5 mmol) in a mixture of THF (5 ml) and methanol (5 ml), and the mixture was stirred for 3 h at RT. Water (10 ml) was added, and the mixture was acidified (pH=3) by addition of HCl. The mixture was stirred for 30 min and filtered. The obtained precipitate was washed with a small amount of water, and was dried under vacuum. The thus obtained title compound (240 mg, 45%) was pure enough to be used in the next step. MS (m/e)=363.3 [M+H$^+$].

Step 3: 3-(Azetidine-1-carbonyl)-1-methyl-1H-pyrazole-4-carboxylic acid (2-phenyl-imidazo[1,2-a]pyrimidin-7-yl)-amide The title compound was obtained in analogy to example 29, step 6, from 1-Methyl-4-(2-phenyl-imidazo[1,2-a]pyrimidin-7-ylcarbamoyl)-1H-pyrazole-3-carboxylic acid.

MS (m/e)=402.3 [M+H$^+$].

Example 67

1-Methyl-1H-pyrazole-3,4-dicarboxylic acid 3-(ethyl-methyl-amide) 4-[(2-phenyl-imidazo[1,2-a]pyrimidin-7-yl)-amide]

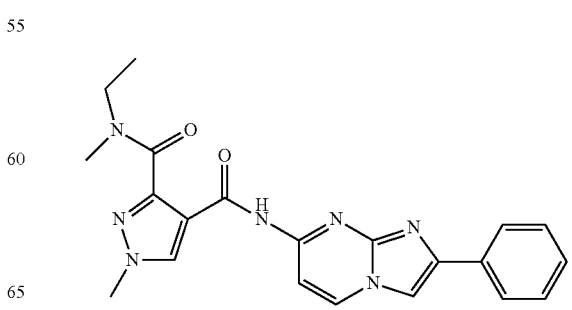

The title compound was prepared in analogy to example 66 from ethyl-methyl-amine. MS (m/e)=404.2 [M+H⁺].

Example 68

1-Methyl-1H-pyrazole-3,4-dicarboxylic acid 4-(ethyl-methyl-amide) 3-[(2-phenyl-imidazo[1,2-a]pyrimidin-7-yl)-amide]

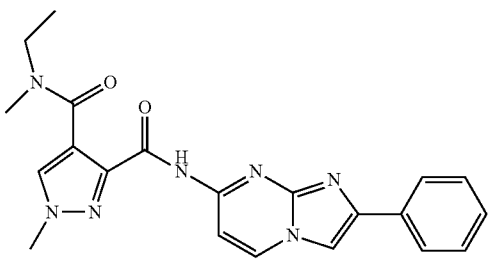 [SMILES: CCN(C)C(=O)c1cn(C)nc1C(=O)Nc1ccn2cc(-c3ccccc3)nc2n1]

The title compound was obtained as a by-product during the preparation of example 67, presumably via an imide-type intermediate during the final coupling step.

MS (m/e)=404.2 [M+H⁺].

Example 69

4-(Azetidine-1-carbonyl)-2-ethyl-2H-pyrazole-3-carboxylic acid (2-phenyl-imidazo[1,2-a]pyrimidin-7-yl)-amide

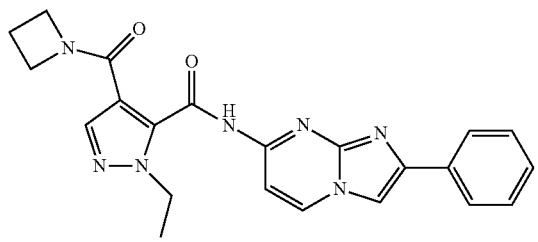 [SMILES: CCn1ncc(C(=O)N2CCC2)c1C(=O)Nc1ccn2cc(-c3ccccc3)nc2n1]

Step 1: 1-Ethyl-5-(2-phenyl-imidazo[1,2-a]pyrimidin-7-ylcarbamoyl)-1H-pyrazole-4-carboxylic acid The title compound was prepared in analogy to example 29, step 5, from ethyl 1-ethyl-5-(2-phenylimidazo[1,2-a]pyrimidin-7-ylcarbamoyl)-1H-pyrazole-4-carboxylate (example 56, step 2). MS (m/e)=377.3 [M+H⁺].

Step 2: 4-(Azetidine-1-carbonyl)-2-ethyl-2H-pyrazole-3-carboxylic acid (2-phenyl-imidazo[1,2-a]pyrimidin-7-yl)-amide The title compound was prepared in analogy to example 29, step 6, from 1-ethyl-5-(2-phenyl-imidazo[1,2-a]pyrimidin-7-ylcarbamoyl)-1H-pyrazole-4-carboxylic acid. MS (m/e)=416.3 [M+H⁺].

Example 70

2-Methyl-2H-pyrazole-3,4-dicarboxylic acid 4-[(2-cyano-ethyl)-methyl-amide]3-[(2-phenyl-imidazo[1,2-a]pyrimidin-7-yl)-amide]

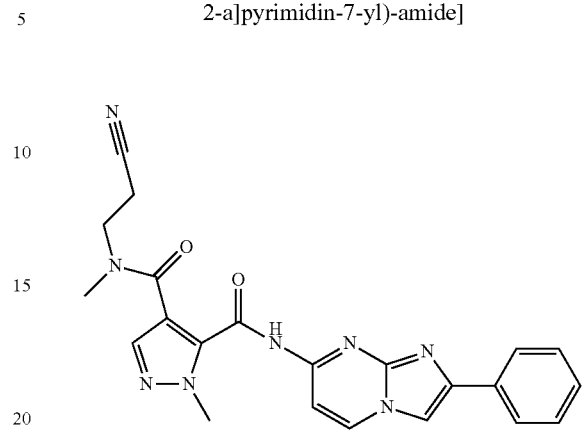

The title compound was prepared in analogy to example 29, step 6, from (2-cyano-ethyl)-methyl-amine. MS (m/e)=429.3 [M+H⁺].

Example 71

2-Methyl-2H-pyrazole-3,4-dicarboxylic acid 4-(isobutyl-methyl-amide) 3-[(2-phenyl-imidazo[1,2-a]pyrimidin-7-yl)-amide]

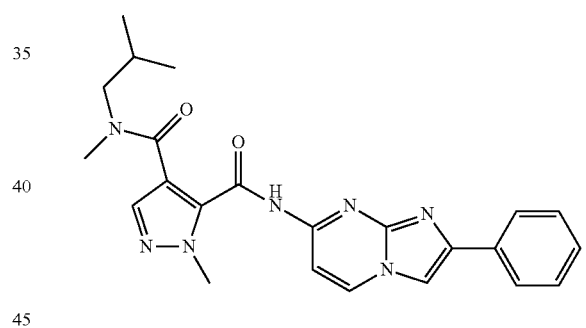

The title compound was prepared in analogy to example 29, step 6, from isobutyl-methyl-amine. MS (m/e)=432.4 [M+H⁺].

Example 72

2-Methyl-2H-pyrazole-3,4-dicarboxylic acid 4-[(2-hydroxy-2-methyl-propyl)-amide]3-[(2-phenyl-imidazo[1,2-a]pyrimidin-7-yl)-amide]

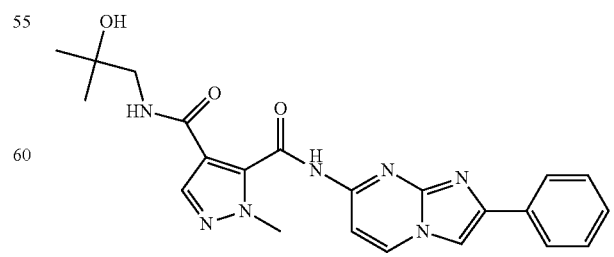

The title compound was prepared in analogy to example 29, step 6, from 2-hydroxy-2-methyl-propyl-amine. MS (m/e)=434.3 [M+H⁺].

Example 73

2-Ethyl-2H-pyrazole-3,4-dicarboxylic acid 4-(ethyl-methyl-amide) 3-[(2-phenyl-imidazo[1,2-a]pyrimidin-7-yl)-amide]

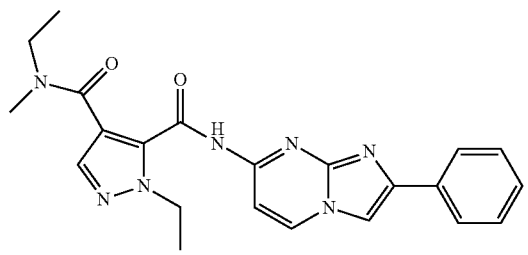 [SMILES: CCN(C)C(=O)c1cnn(CC)c1C(=O)Nc1ccn2cc(-c3ccccc3)nc2n1]

The title compound was prepared in analogy to example 69, step 2, from ethyl-methyl-amine. MS (m/e)=418.3 [M+H$^+$].

Example 74

4-(Azetidine-1-carbonyl)-2-methyl-2H-pyrazole-3-carboxylic acid [2-(5-chloro-thiophen-2-yl)-imidazo[1,2-a]pyrimidin-7-yl]-amide

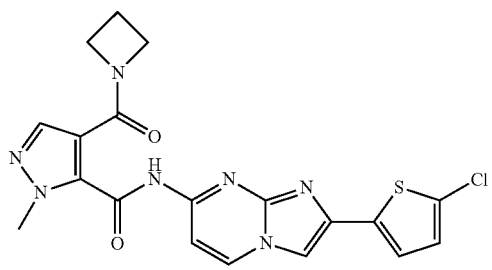 [SMILES: Cn1ncc(C(=O)N2CCC2)c1C(=O)Nc1ccn2cc(-c3ccc(Cl)s3)nc2n1]

The title compound was prepared in analogy to example 29, using 2-(5-chloro-thiophen-2-yl)-imidazo[1,2-a]pyrimidin-7-ylamine. 2-(5-Chloro-thiophen-2-yl)-imidazo[1,2-a]pyrimidin-7-ylamine can be prepared in analogy to example 1, step 1, from 2-bromo-1-(5-chloro-thiophen-2-yl)-ethanone. MS (m/e)=442.2 [M+H$^+$].

Example 75

2-Methyl-2H-pyrazole-3,4-dicarboxylic acid 4-dimethylamide 3-[(2-phenyl-imidazo[1,2-a]pyrimidin-7-yl)-amide]

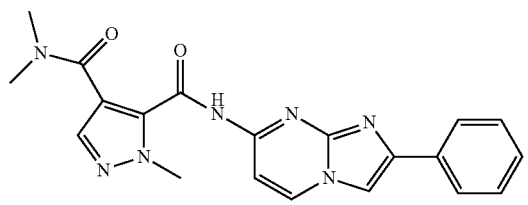 [SMILES: CN(C)C(=O)c1cnn(C)c1C(=O)Nc1ccn2cc(-c3ccccc3)nc2n1]

The title compound was prepared in analogy to example 29, step 6, from dimethylamine hydrochloride. MS (m/e)=390.3 [M+H$^+$].

Example 76

1-Methyl-3-(pyrimidin-5-ylamino)-1H-pyrazole-4-carboxylic acid (2-phenyl-imidazo[1,2-a]pyrimidin-7-yl)-amide

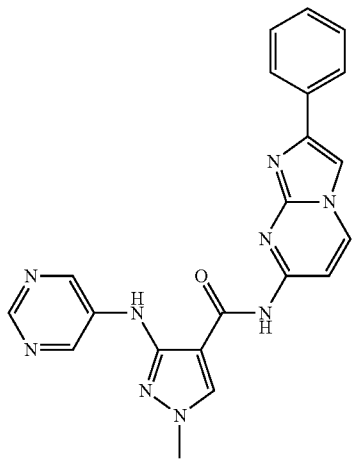 [SMILES: Cn1cc(C(=O)Nc2ccn3cc(-c4ccccc4)nc3n2)c(Nc2cncnc2)n1]

Step 1: 1-Methyl-3-(pyrimidin-5-ylamino)-1H-pyrazole-4-carboxylic acid ethyl ester Under an atmosphere of argon, palladium(II) acetate (79 mg), and subsequently xantphos (4,5-bis(diphenylphosphino)-9,9-dimethylxanthene, 256 mg) was added to a mixture of 5-bromopyridine (2.0 g), 3-amino-1-methyl-1H-pyrazole-4-carboxylic acid ethyl ester (1.5 g), K$_2$CO$_3$ (2.2 g), water (0.33 ml), and o-xylene (20 ml). The mixture was heated to 140° C. for 17 h. Upon cooling and addition of dichloromethane (50 ml), the mixture was filtered and concentrated under vacuum. The title compound (1.52 g, 69%) was obtained from the residue by column chromatography (silica gel, cyclohexane/ethyl acetate gradient).
MS (m/e)=248.2 [M+H$^+$].

Step 2: 1-Methyl-3-(pyrimidin-5-ylamino)-1H-pyrazole-4-carboxylic acid (2-phenyl-imidazo[1,2-a]pyrimidin-7-yl)-amide Trimethylaluminum (2M solution in toluene, 0.3 ml) was added to a stirred suspension of 2-phenyl-imidazo[1,2-a]pyrimidin-7-ylamine (example 1, step 1, 128 mg) in dioxane (5 ml), and the mixture was stirred for 2 h at RT. 1-Methyl-3-(pyrimidin-5-ylamino)-1H-pyrazole-4-carboxylic acid ethyl ester (50 mg) was then added in one portion, and the mixture was heated to 100° C. for 17 h. Upon cooling, water (0.5 ml) was added, followed by small amounts of methanol and dichloromethane to get an almost clear solution. Some MgSO$_4$ was added, the mixture was stirred for 15 min, and filtered. The filtrate was concentrated, and the title compound (23 mg, 28%) was isolated from the residue by column chromatography (silica gel, dichloromethane/methanol gradient), followed by trituration (methanol).
MS (m/e)=412.2 [M+H$^+$].

Example 77

6-Cyclopropyl-3-(pyrimidin-5-ylamino)-pyridine-2-carboxylic acid (2-phenyl-imidazo[1,2-a]pyrimidin-7-yl)-amide

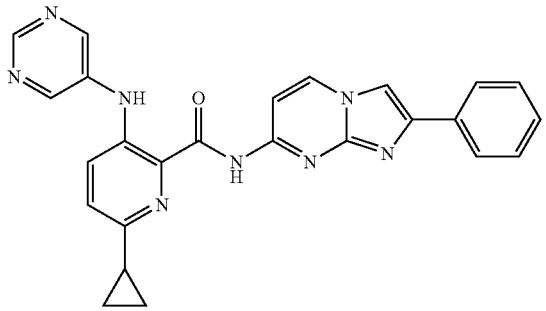 [SMILES: O=C(Nc1ccn2cc(-c3ccccc3)nc2n1)c1nc(C2CC2)ccc1Nc1cncnc1]

Step 1: 6-Cyclopropyl-3-(pyrimidin-5-ylamino)-pyridine-2-carboxylic acid ethyl ester Under an atmosphere of argon, palladium(II) acetate (101 mg), and subsequently xantphos (4,5-bis(diphenylphosphino)-9,9-dimethylxanthene, 325 mg) was added to a mixture of 5-bromopyridine (2.5 g), 3-amino-6-cyclopropyl-pyridine-2-carboxylic acid ethyl ester (2.32 g), $K_2CO_3$ (2.8 g), water (0.43 ml), and o-xylene (30 ml). The mixture was heated to 140° C. for 17 h. Upon cooling and addition of dichloromethane (50 ml), the mixture was filtered and concentrated under vacuum. The title compound (2.59 g, 81%) was obtained from the residue by column chromatography (silica gel, cyclohexane/ethyl acetate gradient). (3-Amino-6-cyclopropyl-pyridine-2-carboxylic acid ethyl ester can be prepared by the method of Georg Jaeschke et al., U.S. Pat. Appl. Publ. (2006) US 2006199960.)
MS (m/e)=285.2 [M+H$^+$].

Step 2: 6-Cyclopropyl-3-(pyrimidin-5-ylamino)-pyridine-2-carboxylic acid (2-phenyl-imidazo[1,2-a]pyrimidin-7-yl)-amide Trimethylaluminum (2M solution in toluene, 0.26 ml) was added to a stirred suspension of 2-phenyl-imidazo[1,2-a]pyrimidin-7-ylamine (example 1, step 1, 111 mg) in dioxane (5 ml), and the mixture was stirred for 2 h at RT. 6-Cyclopropyl-3-(pyrimidin-5-ylamino)-pyridine-2-carboxylic acid ethyl ester (50 mg) was then added in one portion, and the mixture was heated to 100° C. for 17 h. Upon cooling, water (0.5 ml) was added, followed by small amounts of methanol and dichloromethane to get an almost clear solution. Some MgSO$_4$ was added, the mixture was stirred for 15 min, and filtered. The filtrate was concentrated, and the title compound (44 mg, 56%) was isolated from the residue by column chromatography (silica gel, dichloromethane/methanol gradient), followed by trituration (methanol). MS (m/e)=449.2 [M+H$^+$].

Example 78

2-Methoxy-N-(2-phenylimidazo[1,2-a]pyrimidin-7-yl)nicotinamide

A mixture of 2-phenylimidazo[1,2-a]pyrimidin-7-amine (200 mg, 951 μmol, Eq: 1.00), 2-methoxynicotinic acid (146 mg, 951 μmol, Eq: 1.00), diisopropylethylamine (369 mg, 498 μl, 2.85 mmol, Eq: 3) and propylphosphonic anhydride in ethyl acetate 50% (1.21 g, 1.12 ml, 1.9 mmol, Eq: 2) in tetrahydrofuran (10 ml) is stirred for 18 hours at 60° C. The mixture is diluted with ethyl acetate and washed 2 times with water and once with brine, the organic layer was separated, dried over magnesium sulfate, filtrated and evaporated. The crude material was applied on silicagel and purified by flash chromatography over a 20 g silicagel column using ethyl acetate/methanol 0-10% as eluent affording 2-methoxy-N-(2-phenylimidazo[1,2-a]pyrimidin-7-yl)nicotinamide (36 mg, 11%) as a light yellow solid. MS: m/e=346.1 (M+H+), mp: 225-226° C.

Example 79

5-Chloro-2-methyl-N-(2-phenylimidazo[1,2-a]pyrimidin-7-yl)pyrimidine-4-carboxamide

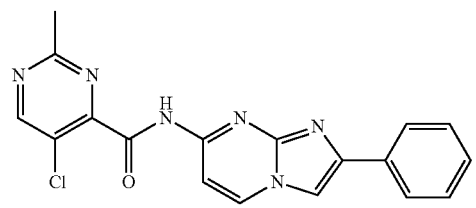 [SMILES: Cc1ncc(Cl)c(C(=O)Nc2ccn3cc(-c4ccccc4)nc3n2)n1]

A mixture of 5-chloro-2-methylpyrimidine-4-carboxylic acid (100 mg, 0.579 mmol), 2-phenylimidazo[1,2-a]pyrimidin-7-amine (146 mg, 0.695 mmol, 1.2 eq), diisopropylethylamine (304 ul, 1.74 mmol, 3 eq) and propylphosphonic anhydride in ethyl acetate 50% (854 ul, 1.45 mmol, 2.5 eq) in tetrahydrofuran (6 ml) is stirred for 1 day at 25° C. The mixture is diluted with ethyl acetate and washed 2 times with water, the organic layer is dried over magnesium sulfate and evapoarted. The crude material was purified by flash chromatography over a 20 g silicagel column using ethyl acetate 100% as eluent to afford 5-chloro-2-methyl-N-(2-phenylimidazo[1,2-a]pyrimidin-7-yl)pyrimidine-4-carboxamide (64 mg, 30.3%) as a yellow solid. MS: m/e=365.1 (M+H$^+$), mp: >250° C.

Example 80

2-Methyl-N-(2-phenylimidazo[1,2-a]pyrimidin-7-yl)isonicotinamide

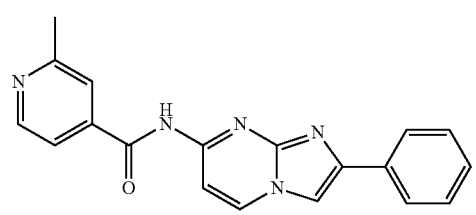 [SMILES: Cc1cc(C(=O)Nc2ccn3cc(-c4ccccc4)nc3n2)ccn1]

A mixture of 2-phenylimidazo[1,2-a]pyrimidin-7-amine (156 mg, 0.766 mmol, 1 eq.), 2-methylisonicotinic acid (116 mg, 0.842 mmol, 1.1 eq.), propylphosphonic anhydride in ethyl acetate 50% (1.13 ml, 1.91 mmol, 2.5 eq) and ethyldiisopropylamine (0.535 ml, 3.06 mmol, 4 eq) in tetrahydrofuran (10 ml) is stirred for 18 hours at roomtemperature. The solution is then refluxed for 4 hours. The mixture is diluted with ethyl acetate and washed with sat. aqueous sodium bicarbonate, with water, dried over magnesium sulfate and the solvent is removed in vacuo. Purification of the residue by chromatography on a 12 g RediSep silica cartridge using dichloromethane+5% methanol as eluent affords 2-methyl-N-(2-phenyl-imidazo[1,2-a]pyrimidin-7-yl)-isonicotinamide (45 mg, 17.8%) as a yellow solid. MS: m/e=330.2 (M+H+)

mp.: 255-7° C.

Example 81

2-Chloro-6-methyl-N-(2-phenylimidazo[1,2-a]pyrimidin-7-yl)isonicotinamide

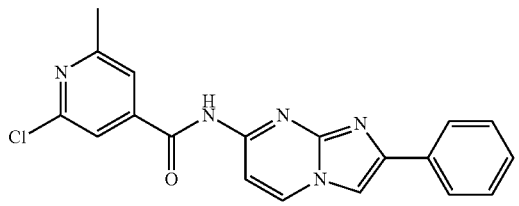 [SMILES: Cc1cc(C(=O)Nc2ccn3cc(-c4ccccc4)nc3n2)cc(Cl)n1]

A mixture of 2-phenylimidazo[1,2-a]pyrimidin-7-amine (141 mg, 0.671 mmol, 1 eq.), 2-chroro-6-methylisonicotinic acid (127 mg, 0.738 mmol, 1.1 eq.), propylphosphonic anhydride in ethyl acetate 50% (0.98 ml, 1.68 mmol, 2.5 eq) and ethyldiisopropylamine (0.47 ml, 2.68 mmol, 4 eq) in tetrahydrofurane (10 ml) is refluxed for 4 hours. The mixture is diluted with ethyl acetate and washed with sat. aqueous sodium bicarbonate, twice with water, dried over magnesium sulfate and the solvent is removed in vacuo. Purification of the residue by chromatography on a 20 g Silicycle silica cartridge using ethyl acetate a eluent affords 2-chloro-6-methyl-N-(2-phenyl-imidazo[1,2-a]pyrimidin-7-yl)-isonicotinamide (129 mg, 52.9%) as a yellow solid (cryst. form heptane/ethlyl acetate 7/3). MS: m/e=364.0 (M+H+), mp.: 148-151° C.
Intermediate Compounds of Formula 3, used in Examples 82-111

2-(3-Fluoro-phenyl)-imidazo[1,2-a]pyrimidin-7-ylamine

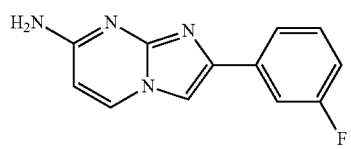 [SMILES: Nc1ccn2cc(-c3cccc(F)c3)nc2n1]

2-Bromo-1-(3-fluorophenyl)ethanone (10.9 g, 50 mmol) was added to a solution of 2,4-diaminopyrimidine (3.70 g, 34 mmol) in acetone (185 ml), and the mixture was heated to reflux for 6 h. The cooled suspension was filtered and the precipitate was washed with acetone (50 ml). The solid was re-suspended in water (35 ml) and NH4OHaq. (25%, 50 ml), then it was collected over a glass fiber paper and the filtrate was washed with H2O (75 ml). After drying under vacuum, the product was obtained (5.56 g, 72%) as a yellow solid.
MS (m/z)=229.1 [M+H+].

3-(7-Amino-imidazo[1,2-a]pyrimidin-2-yl)-phenol hydrobromide

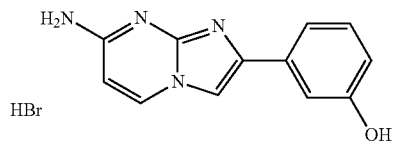 [SMILES: Br ; Nc1ccn2cc(-c3cccc(O)c3)nc2n1]

2-(3-Methoxy-phenyl)-imidazo[1,2-c]pyrimidin-7-ylamine (2.5 g, 10.4 mmol; intermediate to example 45) was combined with 25 ml HBr$_{aq.}$ (48%) to give a light yellow suspension. The reaction mixture was refluxed for 48 h. After cooling to RT, H2O was added and the brown suspension was filtered. The solid was washed with H2O and dried in HV at 40° C. to yield the title compound (2.75 g, 86%) as a white solid.
MS (m/z)=227.2 [M+H+].

2-(3-Fluoromethoxy-phenyl)-imidazo[1,2-a]pyrimidin-7-ylamine

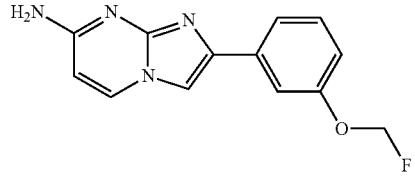 [SMILES: Nc1ccn2cc(-c3cccc(OCF)c3)nc2n1]

In a sealed tube 3-(7-aminoimidazo[1,2-a]pyrimidin-2-yl) phenol hydrobromide (260 mg, 0.85 mmol) was combined in DMF (3 ml) to give a brown solution. Toluene-4-sulfonic acid fluoromethyl ester (249 mg, 1.22 mmol; CAS Nr. 114435-86-8) was dissolved in DMF and added. Cs2CO3 (527 mg, 1.62 mmol) was added. The reaction mixture was heated under argon to 70° C. for 9 h, then stirring was continued overnight at RT. The reaction mixture was diluted with H2O (30 ml) and extracted with EtOAc (3×30 ml). The combined organic layers were dried (MgSO4) and concentrated under vacuum and the crude product was purified by flash chromatography (50 g SiO2, DCM/MeOH/NH$_{3aq.}$ 140:10:1). The title compound (105 mg, 48%) was obtained as a yellow solid.
MS (m/z)=259.1 [M+H+].

2-[3-(2-Fluoro-ethoxy)-phenyl]-imidazo[1,2-a]pyrimidin-7-ylamine

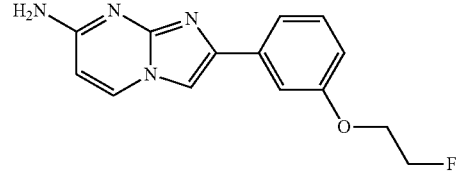 [SMILES: Nc1ccn2cc(-c3cccc(OCCF)c3)nc2n1]

In a sealed tube 3-(7-aminoimidazo[1,2-a]pyrimidin-2-yl)phenol hydrobromide (800 mg, 2.6 mmol) was combined with DMF (4.0 ml) to give a light brown solution. 1-Bromo-2-fluoroethane (476 mg, 3.75 mmol) dissolved in DMF (4.0 ml) and Cs$_2$CO$_3$ (1.62 g, 4.97 mmol) were added. The reaction mixture was stirred 23 h at 70° C. H$_2$O (50 ml) was added to the reaction mixture and the product was extracted with EtOAc (3×40 ml). After drying over MgSO$_4$, filtration and concentration in vacuum, the crude product (orange oil) was purified by flash chromatography (50 g SiO$_2$—NH$_2$ cartridge, eluent: CH$_2$Cl$_2$ to CH$_2$Cl$_2$/MeOH 95:5) to yield the title compound (150 mg, 21%).

MS (m/z)=273.1 [M+H+].

Acetic acid
3-(7-amino-imidazo[1,2-a]pyrimidin-2-yl)-phenyl ester

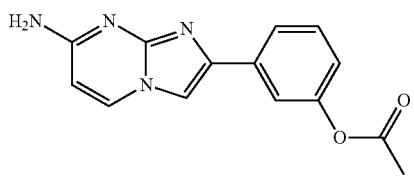 [SMILES: CC(=O)Oc1cccc(-c2cn3ccc(N)nc3n2)c1]

To a microwave vial were added 3-(7-aminoimidazo[1,2-a]pyrimidin-2-yl)phenol hydrobromide (500 mg, 1.63 mmol), acetic anhydride (199 mg, 185 µA, 1.95 mmol) and pyridine (5.00 ml). The vial was capped and heated in the microwave at 120° C. for 15 min. H$_2$O was added to the reaction mixture and the pH was installed around 7-8 by addition of 10% NaHCO$_3$ aq. solution. The product was extracted with CH$_2$Cl$_2$, then the solvent was partially evaporated and the formed solid was collected and purified by flash chromatography (SiO$_2$ cartridge; eluent: CH$_2$Cl$_2$/MeOH/ NH$_3$aq. 140:10:1). White solid (207 mg, 45%).

MS (m/z)=269.1 [M+H+].

[3-(7-Amino-imidazo[1,2-a]pyrimidin-2-yl)-phenoxy]acetic acid methyl ester

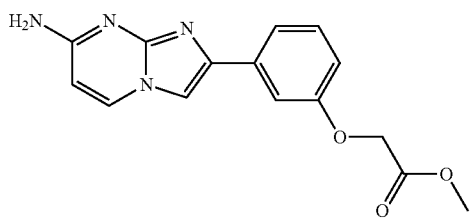 [SMILES: COC(=O)COc1cccc(-c2cn3ccc(N)nc3n2)c1]

3-(7-Aminoimidazo[1,2-c]pyrimidin-2-yl)phenol hydrobromide (100 mg, 0.33 mmol) was combined with DMF (0.2 ml) to give a light brown suspension. Methyl-2-bromoacetate (55 mg, 0.36 mmol) and Cs$_2$CO$_3$ (424 mg, 1.3 mmol) were added, and the reaction mixture was stirred 2 h in a sealed tube at 65° C. The reaction mixture was directly put on a column and the product was isolated by flash chromatography (SiO$_2$—NH$_2$ cartridge; eluent: CH$_2$Cl$_2$/MeOH 95:05) to yield the title compound (57 mg, 58%) as a light yellow solid.

MS (m/z)=299.1 [M+H+].

Carboxylic Acid Intermediates Used in Examples 82-111

4-(Azetidine-1-carbonyl)-1-methyl-1H-pyrazole-5-carboxylic acid

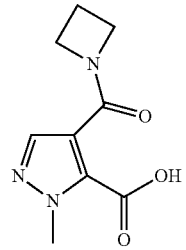

Step 1: Azetidin-1-yl-(1-methyl-1H-pyrazol-4-yl)-methanone

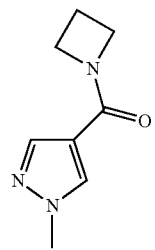

Methyl-1H-pyrazole-4-carboxylic acid (1.0 g, 7.93 mmol; CAS Nr. 5952-92-1) was combined with DMF (10.0 ml) to give a colorless solution. Et$_3$N (2.41 g, 3.32 ml, 23.8 mmol) and 2-(1H-benzo[d][1,2,3]triazol-1-yl)-1,1,3,3-tetramethylisouronium tetrafluoroborate (TBTU, 2.8 g, 8.72 mmol) were added and the reaction mixture was stirred at RT for 1 h. Azetidine (475 mg, 8.33 mmol) was added and the stirring was continued overnight. DMF was partially removed under high vacuum, H$_2$O and 10% NaHCO$_3$ aq. solution were added to the residue, and the compound was extracted with EtOAc. After drying over Na$_2$SO$_4$, filtration and concentration under vacuum, the crude product was purified by flash chromatography (50 g SiO$_2$—NH$_2$ cartridge; eluent: CH$_2$Cl$_2$/MeOH 95:05). More product was isolated from the aqueous phase by full evaporation and a second chromatography. White solid (971 mg, 74%).

MS (m/z)=166.2 [M+H+].

Step 2: 4-(Azetidine-1-carbonyl)-1-methyl-1H-pyrazole-5-carboxylic acid

Azetidin-1-yl(1-methyl-1H-pyrazol-4-yl)methanone (467.2 mg, 2.83 mmol) was combined under N$_2$ with THF (10.0 ml) to give a colorless solution. 1,1,4,7,7-Pentamethyldiethylenetriamine (539 mg, 650 µA, 3.11 mmol) was added, the solution was cooled to −78° C. and 1.6 M tBuLi in heptane (2.65 ml, 4.24 mmol, Eq: 1.50) was added drop by drop. After stirring 30 min an excess of dry ice was added carefully. After 5 min at −78° C. the yellow suspension was allowed to warm up to RT. After stirring 1 h H$_2$O was added to the reaction mixture and an extraction (CH$_2$Cl$_2$) was performed. The H$_2$O layer was acidified using 1N HCl solution, and the acid was extracted (CH$_2$Cl$_2$). After drying over Na₂SO₄, filtration and concentration under vacuum, the product was dried under high vacuum. Off-white solid (496 mg, 84%). MS (m/z)=210.1 [M+H+].

The following calboxylic acid intermediates were prepared in analogy to 4-(azetidine-1-carbonyl)-1-methyl-1H-pyrazole-5-carboxylic acid:

4-(Dimethylcarbamoyl)-1-methyl-1H-pyrazole-5-carboxylic acid

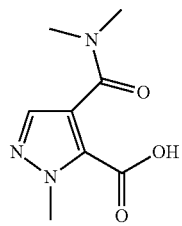

Step 1:
N,N-1-Trimethyl-1H-pyrazole-4-carboxamide

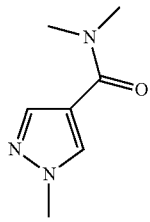

From 1-methyl-1H-pyrazole-4-carboxylic acid (1.00 g, 7.93 mmol) and dimethylamine hydrochloride (679 mg, 8.33 mmol). Off-white solid (1.12 g, 92%).
MS (m/z)=154.1 [M+H+].

Step 2: 4-(Dimethylcarbamoyl)-1-methyl-1H-pyrazole-5-carboxylic acid

From N,N-1-trimethyl-1H-pyrazole-4-carboxamide (300 mg, 1.96 mmol). White solid (329 mg, 82%). MS (m/z)= 198.1 [M+H+].

4-(Ethyl(methyl)carbamoyl)-1-methyl-1H-pyrazole-5-carboxylic acid

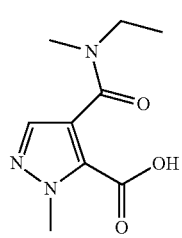

Step 1:
N-Ethyl-N-1-dimethyl-1H-pyrazole-4-carboxamide

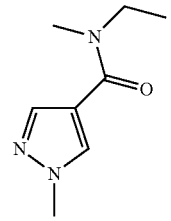

From 1-methyl-1H-pyrazole-4-carboxylic acid (1 g, 7.93 mmol) and N-methylethanamine (492 mg, 715 µA, 8.33 mmol). Off. white solid (995 mg, 75%).
MS (m/z)=168.1 [M+H+].

Step 2: 4-(Ethyl(methyl)carbamoyl)-1-methyl-1H pyrazole-5-carboxylicacid

From N-ethyl-N-1-dimethyl-1H-pyrazole-4-carboxamide (514.4 mg, 3.08 mmol). Light brown solid (460 mg, 69%). MS (m/z)=212.1 [M+H+].

4-β2-Fluoroethyl)(methyl)carbamoyl)-1-methyl-1H-pyrazole-5-carboxylic acid

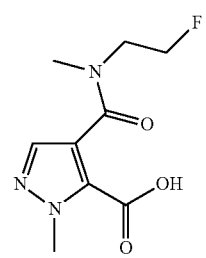 [SMILES: CN(CCF)C(=O)c1cnn(C)c1C(=O)O]

Step 1: 1-Methyl-1H-pyrazole-4-carboxylic acid (2-fluoro-ethyl)-methyl-amide

From 1-methyl-1H-pyrazole-4-carboxylic acid (1.0 g, 7.93 mmol) and 2-fluoro-N-methylethanamine hydrochloride (991 mg, 8.72 mmol). Yellow oil (1.41 g, 92%).
MS (m/z)=186.1 [M+H+].

Step 2: 4((2-Fluoroethyl)(methyl)carbamoyl)-1-methyl-1H-pyrazole-5-carboxylic acid From 1-methyl-1H-pyrazole-4-carboxylic acid (2-fluoro-ethyl)-methyl-amide (500 mg, 2.7 mmol). Light brown viscous oil (307 mg, 50%).
MS (m/z)=230.2 [M+H+].

4-((2-Methoxyethyl)(methyl)carbamoyl)-1-methyl-1H-pyrazole-5-carboxylic acid

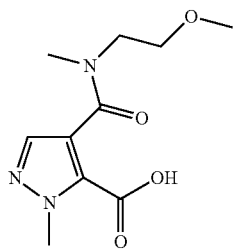 [SMILES: COCCN(C)C(=O)c1cnn(C)c1C(=O)O]

Step 1: N-(2-Methoxyethyl)-N-1-dimethyl-1H-pyrazole-4-carboxamide

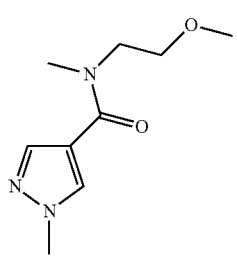

From 1-methyl-1H-pyrazole-4-carboxylic acid (500 mg, 3.96 mmol) and 2-methoxy-N-methylethanamine (389 mg, 4.36 mmol). Colorless liquid (580 mg, 74%).
MS (m/z)=198.2 [M+H+].

Step 2: 4-((2-Methoxyethyl)(methyl)carbamoyl)-1-methyl-1H-pyrazole-5-carboxylic acid From N-(2-methoxyethyl)-N-1-dimethyl-1H-pyrazole-4-carboxamide (550 mg, 2.79 mmol). Colorless waxy solid (590 mg, 88%).
MS (m/z)=240.1 [M−H−].

4-((2-(2-Fluoroethoxy)ethyl)(methyl)carbamoyl)-1-methyl-1H-pyrazole-5-carboxylic acid

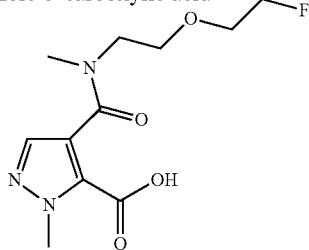 [SMILES: CN(CCOCCF)C(=O)c1cnn(C)c1C(=O)O]

Step 1: [2-(2-Fluoro-ethoxy)-ethyl]-methyl-carbamic acid tert-butyl ester

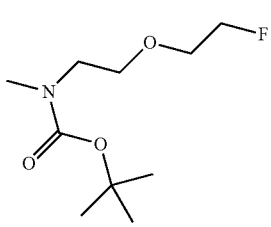

To a solution of (2-hydroxy-ethyl)-methyl-carbamic acid tert-butyl ester (CAS Nr. 57561-39-4; 2.50 g, 14.3 mmol) in toluene (35 ml) was added powered KOH (2.8 g, 50 mmol) and Bu₄NHSO₄ (0.97 mg, 2.86 mmol). The reaction mixture was stirred vigorously and heated to 50° C. while neat 1-bromo-2-fluoro-ethane (2.72 g, 21.4 mmol) was added slowly. The temperature was increased to 80° C. and maintained for 3-5 h. The reaction mixture was cooled to RT, water was added (50 ml) and the pH was adjusted to 7 with 1N HCl solution. Extraction with EtOAc (2×150 ml), washing with brine, drying with Na₂SO₄ and concentrating under vacuum yielded the crude product. The crude material was subjected to column chromatography on silica by EtOAc:hexane (10:90 to 20:80) to give the desired product as light yellow liquid (1.2 g, 38%). MS (m/z)=122.0 [M−Boc+]; 166.2 [M−tBu+].

Step 2: [2-(2-Fluoro-ethoxy)-ethyl]-methyl-amine hydrochloride

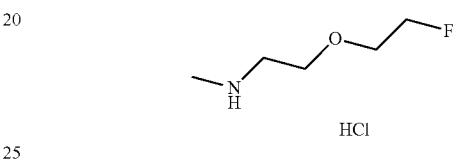

To a stirred solution of [2-(2-fluoro-ethoxy)-ethyl]-methyl-carbamic acid tert-butyl ester (2.00 g, 0.05 mmol) in dry 1,4-dioxane (20 ml) was added 4M HCl in 1,4-dioxane (22.6 ml, 90 mmol) dropwise at 0° C. The reaction mixture was stirred at RT for 5 h. Volatiles were removed under vacuum. The crude material was washed with hexane and dried under vacuum to give desired product [2-(2-fluoro-ethoxy)-ethyl]-methyl-amine hydrochloride as pale yellow solid (1.2 g, 84%).
MS (m/z)=122.0 [M+H+].

Step 3: N-(2-(2-Fluoroethoxy)ethyl)-N-1-dimethyl-1H-pyrazole-4-carboxamide

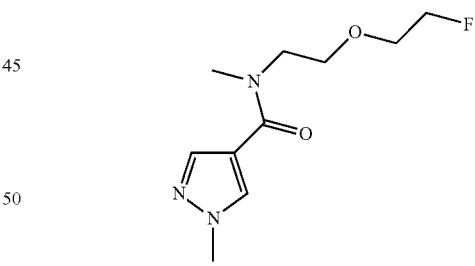

From 1-methyl-1H-pyrazole-4-carboxylic acid (1.00 g, 7.93 mmol) and [2-(2-fluoro-ethoxy)-ethyl]-methyl-amine hydrochloride. Light yellow oil (1.82 g, 95%).
MS (m/z)=230.2 [M+H+].

Step 4: 4-((2-(2-Fluoroethoxy)ethyl)(methyl)carbamoyl)-1-methyl-1H-pyrazole-5-carboxylic acid From N-(2-(2-fluoroethoxy)ethyl)-N-1-dimethyl-1H-pyrazole-4-carboxamide (500 mg, 2.18 mmol). Yellow oil (448 mg, 88%).
MS (m/z)=272.1 [M−H−].

4-(3-Fluoroazetidine-1-carbonyl)-1-methyl-1H-pyrazole-5-carboxylic acid

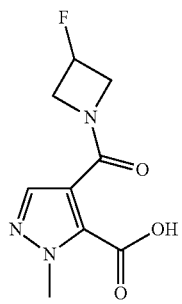 [SMILES: Cn1ncc(C(=O)N2CC(F)C2)c1C(=O)O]

Step 1: (3-Fluoroazetidin-1-yl)(1-methyl-1H-pyrazol-4-yl)methanone

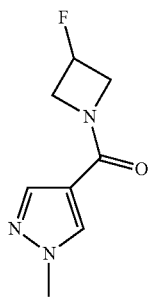

From 1-methyl-1H-pyrazole-4-carboxylic acid (1.0 g, 7.93 mmol) and 3-fluoroazetidine hydrochloride (884 mg, 7.93 mmol). Off-white solid (597 mg, 41%).
MS (m/z)=184.1 [M+H+].

Step 2: 4-(3-Fluoroazetidine-1-carbonyl)-1-methyl-1H-pyrazole-5-carboxylic acid From (3-fluoroazetidin-1-yl)(1-methyl-1H-pyrazol-4-yl)methanone (500 mg, 2.73 mmol). White Solid (352 mg, 57%).
MS (m/z)=226.2 [M+H+].

Example 82

4-(Azetidine-1-carbonyl)-N-(2-(3-(fluoromethoxy)phenyl)imidazo[1,2-a]pyrimidin-7-yl)-1-methyl-1H-pyrazole-5-carboxamide

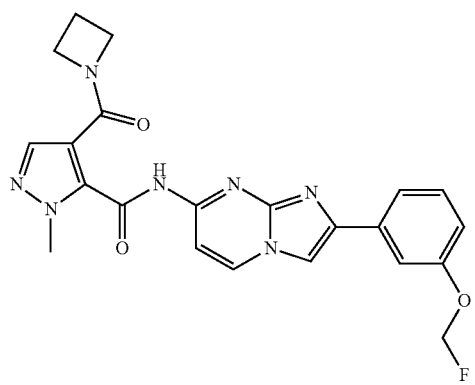 [SMILES: Cn1ncc(C(=O)N2CCC2)c1C(=O)Nc1ccn2cc(-c3cccc(OCF)c3)nc2n1]

2-(3-Fluoromethoxy-phenyl)-imidazo[1,2-c]pyrimidin-7-ylamine (100 mg, 0.387 µmol) was combined with EtOAc (2.0 ml) to give a light yellow suspension. 4-(Azetidine-1-carbonyl)-1-methyl-1H-pyrazole-5-carboxylic acid (97 mg, 465 µmol) and DIPEA (300 mg, 406 µl, 2.32 mmol) were added. The reaction mixture was cooled down to 0° C. and n-propylphosphonic acid anhydride, cyclic trimer (616 mg, 582 µl, 968 µmol) was added drop by drop. After stirring at 0° C. for 30 min the reaction mixture was allowed to warm-up and stirred at RT overnight. The reaction mixture was then diluted with and 10% NaHCO₃ aq. solution and extracted with EtOAc (3×). The combined organic layers were dried (MgSO₄) and concentrated under vacuum. The crude product was purified by flash chromatography (10 g SiO₂; eluent: CH₂Cl₂ to CH₂Cl₂/MeOH/NH₃ 140:10:1). The obtain material was dissolved in CH₂Cl₂ and the product was precipitated with Et₂O, filtered off, washed with Et₂O, and dried overnight at HV. Yellow solid (89 mg, 47%). MS (m/z)=450.2 [M+H+].

Example 83

4-(Azetidine-1-carbonyl)-2-methyl-2H-pyrazole-3-carboxylic acid [2-(3-hydroxy-phenyl)-imidazo[1,2-a]pyrimidin-7-yl]-amide

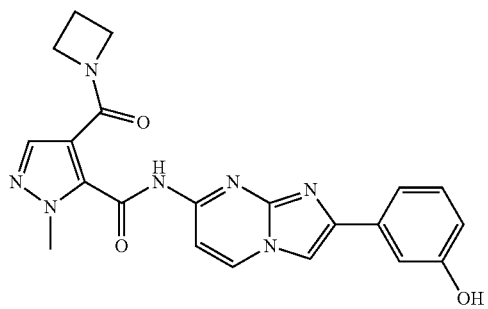 [SMILES: Cn1ncc(C(=O)N2CCC2)c1C(=O)Nc1ccn2cc(-c3cccc(O)c3)nc2n1]

3-(7-(4-(Azetidine-1-carbonyl)-1-methyl-1H-pyrazole-5-carboxamido)imidazo[1,2-a]pyrimidin-2-yl)phenyl acetate (Example 105; 25 mg, 54.4 µmol) was combined with MeOH (0.7 ml), CH₂Cl₂ (0.2 ml) and H₂O to give a yellow solution. NaHCO₃ (4.57 mg, 54.4 µmol) was added and the reaction mixture was stirred at RT over night. The precipitated light yellow solid was filtered and washed with MeOH and H₂O. After drying over night under high vacuum, the product (13 mg, 56%) was obtained as light yellow solid. MS (m/z)=418.2 [M+H+].

Example 84

2-Methyl-2H-pyrazole-3,4-dicarboxylic acid 4-dimethylamide 3-{[2-(3-hydroxy-phenyl)-imidazo[1,2-a]pyrimidin-7-yl]-amide}

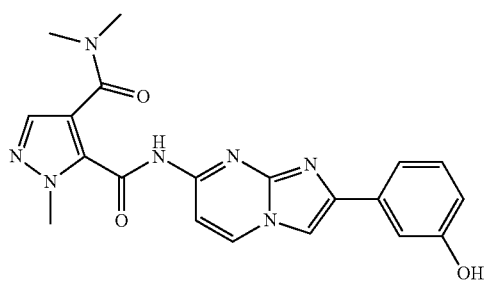 [SMILES: CN(C)C(=O)c1cnn(C)c1C(=O)Nc1ccn2cc(-c3cccc(O)c3)nc2n1]

3-(7-(4-(Dimethylcarbamoyl)-1-methyl-1H-pyrazole-5-carboxamido)imidazo[1,2-a]pyrimidin-2-yl)phenyl acetate (Example 93, 46.7 mg, 104 µmol) was combined with MeOH (1.5 ml), and H$_2$O to give a yellow solution. NaHCO$_3$ (8.77 mg, 0.75 ml, 104 µmol) was added and the reaction mixture was stirred at RT over night. The reaction mixture was quenched to pH 7 with 0.1N HCl solution, the solvents were evaporated until dryness and the residue was purified by two consecutive flash chromatographies (10 g SiO$_2$ cartridge; eluent CH$_2$Cl$_2$/MeOH/NH$_3$aq. 140:10:1; then 10 g SiO$_2$—NH$_2$ cartridge; eluent: CH$_2$Cl$_2$). Light yellow solid (18 mg, 42%). MS (m/z)=406.3 [M+H+].

Example 85

2-Methyl-2H-pyrazole-3,4-dicarboxylic acid 4-dimethylamide 3-{[2-(3-methoxy-phenyl)-imidazo[1,2-a]pyrimidin-7-yl]-amide}

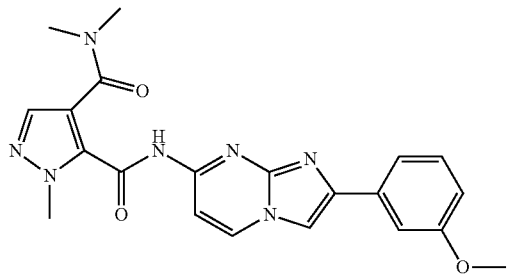 [SMILES: COc1cccc(-c2cn3ccc(NC(=O)c4c(C(=O)N(C)C)cnn4C)nc3n2)c1]

The title compound was prepared in analogy to example 82 from 2-(3-methoxyphenyl)imidazo[1,2-a]pyrimidin-7-amine (100 mg, 416 µmol) and 4-(dimethylcarbamoyl)-1-methyl-1H-pyrazole-5-carboxylic acid (98.5 mg, 499 µmol). Yellow solid (86 mg, 48%). MS (m/z)=420.2 [M+H+].

Example 86

N-4-Ethyl-N5-(2-(3-(fluoromethoxy)phenyl)imidazo[1,2-a]pyrimidin-7-yl)-N4,1-dimethyl-1H-pyrazole-4,5-dicarboxamide

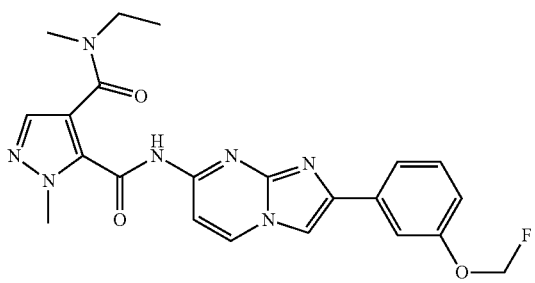 [SMILES: CCN(C)C(=O)c1cnn(C)c1C(=O)Nc1ccn2cc(-c3cccc(OCF)c3)nc2n1]

The title compound was prepared in analogy to example 82 from 2-(3-(fluoromethoxy)phenyl)imidazo[1,2-a]pyrimidin-7-amine (67.0 mg, 259 µmol) and 4-(ethyl(methyl)carbamoyl)-1-methyl-1H-pyrazole-5-carboxylic acid (65.8 mg, 311 µmol). Yellow solid (24 mg, 20%). MS (m/z)=452.2 [M+H+].

Example 87

N-4-ethyl-N5-(2-(3-methoxyphenyl)imidazo[1,2-a]pyrimidin-7-yl)-N-4,1-dimethyl-1H-pyrazole-4,5-dicarboxamide

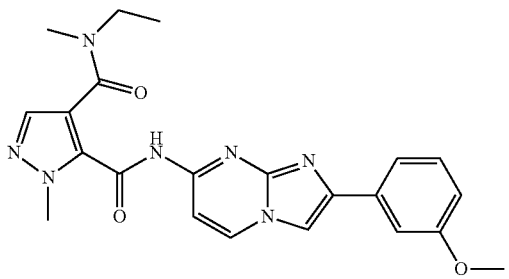 [SMILES: CCN(C)C(=O)c1cnn(C)c1C(=O)Nc1ccn2cc(-c3cccc(OC)c3)nc2n1]

The title compound was prepared in analogy to example 82 from 2-(3-methoxyphenyl)imidazo[1,2-a]pyrimidin-7-amine (65 mg, 271 µmol) and 4-(ethyl(methyl)carbamoyl)-1-methyl-1H-pyrazole-5-carboxylic acid (68.6 mg, 325 µmol). Off-white solid (72 mg, 60%). MS (m/z)=434.9 [M+H+].

Example 88

2-Methyl-2H-pyrazole-3,4-dicarboxylic acid 4-dimethylamide 3-{[2-(3-fluoromethoxy-phenyl)-imidazo[1,2-a]pyrimidin-7-yl]-amide}

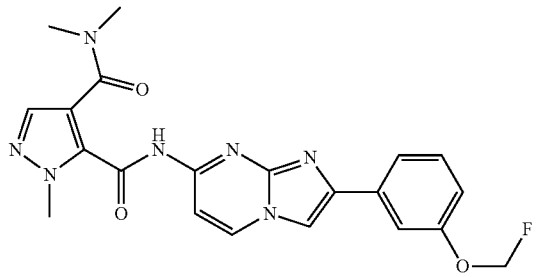 [SMILES: CN(C)C(=O)c1cnn(C)c1C(=O)Nc1ccn2cc(-c3cccc(OCF)c3)nc2n1]

The title compound was prepared in analogy to example 82 from 2-(3-(fluoromethoxy)phenyl)imidazo[1,2-a]pyrimidin-7-amine (105 mg, 407 µmol) and 4-(dimethylcarbamoyl)-1-methyl-1H-pyrazole-5-carboxylic acid (96.2 mg, 488 µmol). Light yellow solid (114 mg, 64%). MS (m/z)=438.2 [M+H+].

Example 89

2-Methyl-2H-pyrazole-3,4-dicarboxylic acid 4-(ethyl-methyl-amide) 3-({2-[3-(2-fluoro-ethoxy)-phenyl]imidazo[1,2-a]pyrimidin-7-yl}-amide)

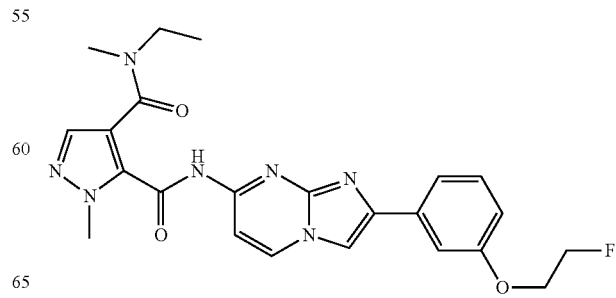

The title compound was prepared in analogy to example 82 from 2-(3-(2-fluoroethoxy)phenyl)imidazo[1,2-a]pyrimidin-7-amine (100 mg, 367 μmol) and 4-(ethyl(methyl)carbamoyl)-1-methyl-1H-pyrazole-5-carboxylic acid (93.1 mg, 441 μmol). Yellow solid (49 mg, 29%). MS (m/z)=466.2 [M+H+].

Example 90

4-(3-Fluoro-azetidine-1-carbonyl)-2-methyl-2H-pyrazole-3-carboxylic acid {2-[3-(2-fluoro-ethoxy)-phenyl]imidazo[1,2-a]pyrimidin-7-yl}-amide

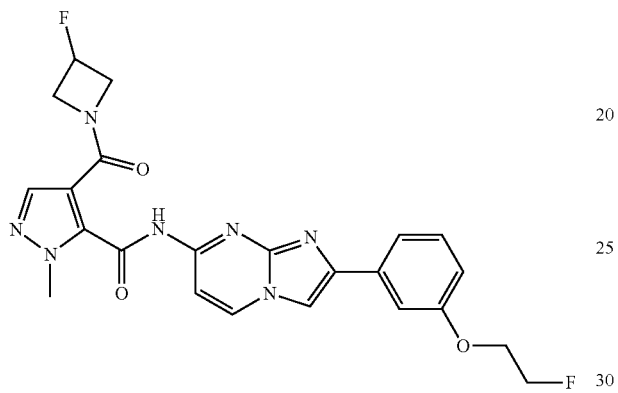

The title compound was prepared in analogy to example 82 from 2-(3-(2-fluoroethoxy)phenyl)imidazo[1,2-a]pyrimidin-7-amine (120 mg) and 4-(3-fluoroazetidine-1-carbonyl)-1-methyl-1H-pyrazole-5-carboxylic acid (100 mg, 440 μmol). Light brown solid (132 mg, 60%). MS (m/z)=482.2 [M+H+].

Example 91

4-(Azetidine-1-carbonyl)-2-methyl-2H-pyrazole-3-carboxylic acid [2-(3-fluoro-phenyl)-imidazo[1,2-a]pyrimidin-7-yl]-amide

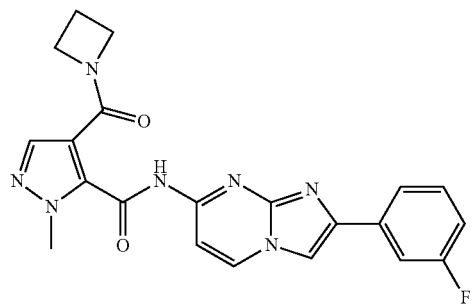 [SMILES: Cn1ncc(C(=O)N2CCC2)c1C(=O)Nc1ccn2cc(-c3cccc(F)c3)nc2n1]

The title compound was prepared in analogy to example 82 from 4-(azetidine-1-carbonyl)-1-methyl-1H-pyrazole-5-carboxylic acid (91.7 mg, 438 μmol) and 2-(3-fluorophenyl)imidazo[1,2-c]pyrimidin-7-amine (100 mg, 438 μmol). Yellow solid (6.5 mg, 3.5%). MS (m/z)=420.1 [M+H+].

Example 92

4-(3-Fluoro-azetidine-1-carbonyl)-2-methyl-2H-pyrazole-3-carboxylic acid [2-(3-fluoro-phenyl)-imidazo[1,2-a]pyrimidin-7-yl]-amide

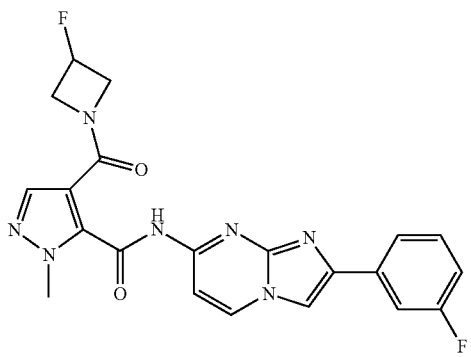 [SMILES: Cn1ncc(C(=O)N2CC(F)C2)c1C(=O)Nc1ccn2cc(-c3cccc(F)c3)nc2n1]

The title compound was prepared in analogy to example 82 from 2-(3-fluorophenyl)imidazo[1,2-c]pyrimidin-7-amine (100 mg) and 4-(3-fluoroazetidine-1-carbonyl)-1-methyl-1H-pyrazole-5-carboxylic acid (100 mg, 440 μmol). Yellow solid (76 mg, 39%).
MS (m/z)=438.1 [M+H+].

Example 93

3-(7-(4-(dimethylcarbamoyl)-1-methyl-1H-pyrazole-5-carboxamido)imidazo[1,2-a]pyrimidin-2-yl)phenyl acetate

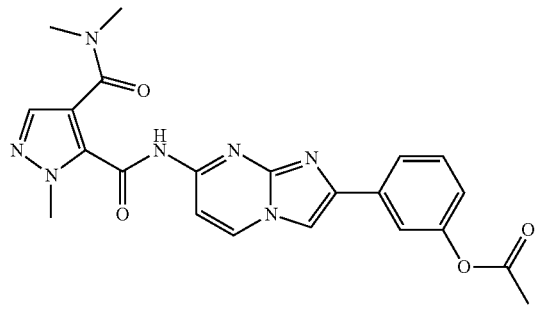 [SMILES: CC(=O)Oc1cccc(-c2cn3ccc(NC(=O)c4c(C(=O)N(C)C)cnn4C)nc3n2)c1]

The title compound was prepared in analogy to example 82, step 3, from 4-dimethylcarbamoyl-2-methyl-2H-pyrazole-3-carboxylic acid (step 2, example 85; 44.1 mg, 224 μmol) and acetic acid 3-(7-amino-imidazo[1,2-a]pyrimidin-2-yl)-phenyl ester (50 mg, 186 μmol). Yield: 53 mg (60%). Yellow solid. MS (m/z)=448.2 [M+H+].

Example 94

2-Methyl-2H-pyrazole-3,4-dicarboxylic acid 4-dimethylamide 3-{[2-(3-fluoro-phenyl)-imidazo[1,2-a]pyrimidin-7-yl]amide}

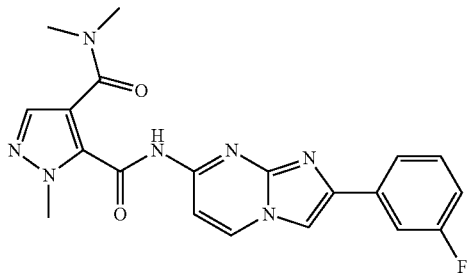 [SMILES: CN(C)C(=O)c1cnn(C)c1C(=O)Nc1ccn2cc(-c3cccc(F)c3)nc2n1]

83

The title compound was prepared in analogy to example 82 from 2-(3-fluorophenyl)imidazo[1,2-a]pyrimidin-7-amine (95 mg, 416 µmol) and 4-(dimethylcarbamoyl)-1-methyl-1H-pyrazole-5-carboxylic acid (98.5 mg, 500 µmol). Light yellow solid (31.9 mg, 19%). MS (m/z)=408.1 [M+H+].

Example 95

2-Methyl-2H-pyrazole-3,4-dicarboxylic acid 4-[(2-fluoro-ethyl)-methyl-amide]3-[(2-phenyl-imidazo[1,2-a]pyrimidin-7-yl)-amide]

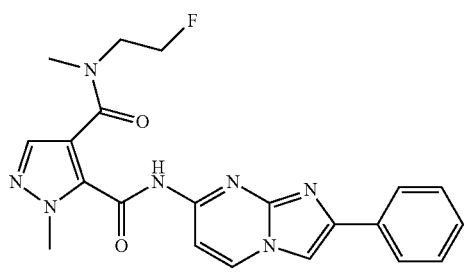 [SMILES: CN(CCF)C(=O)c1cnn(C)c1C(=O)Nc1ccn2cc(-c3ccccc3)nc2n1]

The title compound was prepared in analogy to example 82 from 2-phenylimidazo[1,2-a]pyrimidin-7-amine (90 mg, 428 µmol) and 442-fluoroethyl)(methyl)carbamoyl)-1-methyl-1H-pyrazole-5-carboxylic acid (118 mg, 514 µmol). Light yellow solid (60 mg, 31%).

MS (m/z)=422.2 [M+H+].

Example 96

2-Methyl-2H-pyrazole-3,4-dicarboxylic acid 3-({2-[3-(2-fluoro-ethoxy)-phenyl]-imidazo[1,2-a]pyrimidin-7-yl}-amide) 4-[(2-methoxy-ethyl)-methyl-amide]

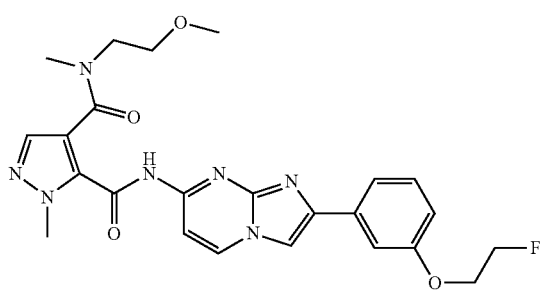 [SMILES: COCCN(C)C(=O)c1cnn(C)c1C(=O)Nc1ccn2cc(-c3cccc(OCCF)c3)nc2n1]

The title compound was prepared in analogy to example 82 from 2-(3-(2-fluoroethoxy)phenyl)imidazo[1,2-a]pyrimidin-7-amine (100 mg, 367 µmol) and 4-[(2-methyl-ethyl)-methyl-carbamoyl]-2-methyl-2H-pyrazole-3-carboxylic acid (106 mg, 441 µmol). Yellow solid (6.7 mg, 3.1%). MS (m/z)=496.2 [M+H+].

84

Example 97

2-Methyl-2H-pyrazole-3,4-dicarboxylic acid 4-(ethyl-methyl-amide) 3-{[2-(3-fluoro-phenyl)-imidazo[1,2-a]pyrimidin-7-yl]-amide}

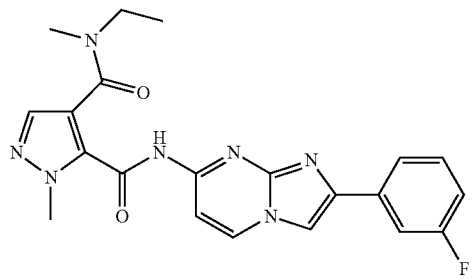 [SMILES: CCN(C)C(=O)c1cnn(C)c1C(=O)Nc1ccn2cc(-c3cccc(F)c3)nc2n1]

The title compound was prepared in analogy to example 82 from 2-(3-fluorophenyl)imidazo[1,2-a]pyrimidin-7-amine (100 mg, 438 µmol) and 4-(ethyl(methyl)carbamoyl)-1-methyl-1H-pyrazole-5-carboxylic acid (111 mg, 526 µmol). Light yellow solid (7.2 mg, 3.9%). MS (m/z)=422.2 [M+H+].

Example 98

4-(3-Fluoro-azetidine-1-carbonyl)-2-methyl-2H-pyrazole-3-carboxylic acid [2-(3-methoxy-phenyl)-imidazo[1,2-a]pyrimidin-7-yl]-amide

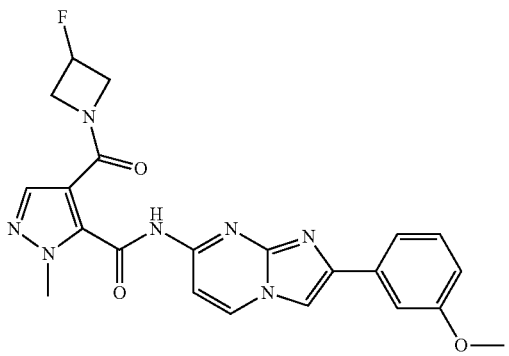 [SMILES: COc1cccc(-c2cn3ccc(NC(=O)c4c(C(=O)N5CC(F)C5)cnn4C)nc3n2)c1]

The title compound was prepared in analogy to example 82 from 4-(3-fluoroazetidine-1-carbonyl)-1-methyl-1H-pyrazole-5-carboxylic acid (100 mg, 440 µmol) and 2-(3-methoxyphenyl)imidazo[1,2-a]pyrimidin-7-amine (106). Yellow solid (142 mg, 72%).
MS (m/z)=450.2 [M+H+].

Example 99

2-Methyl-2H-pyrazole-3,4-dicarboxylic acid 3-{[2-(3-fluoromethoxy-phenyl)-imidazo[1,2-a]pyrimidin-7-yl]-amide}-4-[(2-methoxy-ethyl)-methyl-amide]

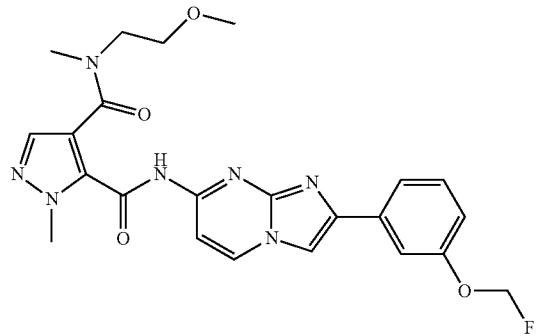

The title compound was prepared in analogy to example 82 from 2-(3-(fluoromethoxy)phenyl)imidazo[1,2-c]pyrimidin-7-amine (100 mg, 387 μmol) and 4-[(2-methyl-ethyl)-methyl-carbamoyl]-2-methyl-2H-pyrazole-3-carboxylic acid (112 mg, 465 μmol). Yellow solid (41 mg, 20%). MS (m/z)=482.3 [M+H+].

Example 100

[3-(7-{[4-(Ethyl-methyl-carbamoyl)-2-methyl-2H-pyrazole-3-carbonyl]-amino}-imidazo[1,2-a]pyrimidin-2-yl)-phenoxy]-acetic acid methyl ester

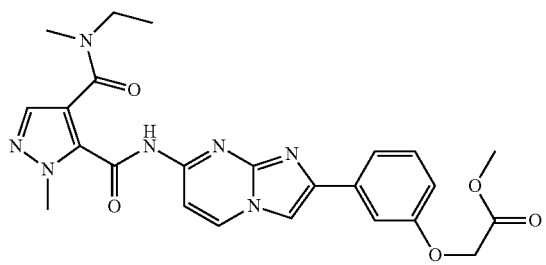 [SMILES: CCN(C)C(=O)c1cnn(C)c1C(=O)Nc1ccn2cc(-c3cccc(OCC(=O)OC)c3)nc2n1]

The title compound was prepared in analogy to example 82 from methyl 2-(3-(7-aminoimidazo[1,2-c]pyrimidin-2-yl)phenoxy)acetate (105 mg, 352 μmol) and 4-(ethyl(methyl)carbamoyl)-1-methyl-1H-pyrazole-5-carboxylic acid (74.3 mg, 352 μmol). Light yellow solid (30 mg, 16%). MS (m/z)=492.2 [M+H+].

Example 101

2-Methyl-2H-pyrazole-3,4-dicarboxylic acid 4-[(2-methoxy-ethyl)-methyl-amide]3-{[2-(3-methoxy-phenyl)-imidazo[1,2-a]pyrimidin-7-yl]amide}

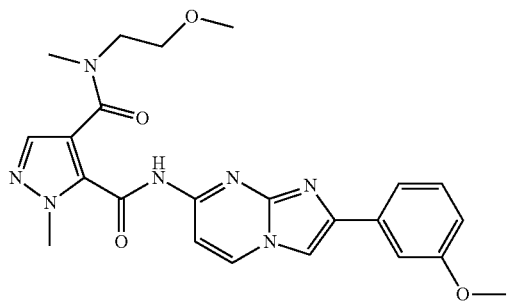 [SMILES: COCCN(C)C(=O)c1cnn(C)c1C(=O)Nc1ccn2cc(-c3cccc(OC)c3)nc2n1]

The title compound was prepared in analogy to example 82 from 2-(3-methoxyphenyl)imidazol[1,2-a]pyrimidin-7-amine (100 mg, 416 μmol) and 4-[(2-methyl-ethyl)-methyl-carbamoyl]-2-methyl-2H-pyrazole-3-carboxylic acid (120 mg, 499 μmol). Light yellow solid (79 mg, 38%). MS (m/z)=464.2 [M+H+].

Example 102

2-Methyl-2H-pyrazole-3,4-dicarboxylic acid 4-dimethylamide 3-({2-[3-(2-fluoro-ethoxy)-phenyl]-imidazo[1,2-a]pyrimidin-7-yl}-amide)

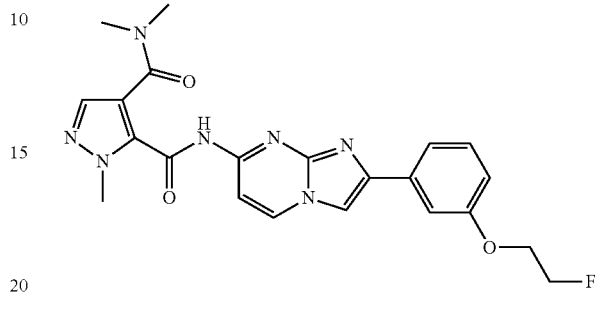

Step 1: 5-{2-[3-(2-Fluoro-ethoxy)-phenyl]-imidazo[1,2-a]pyrimidin-7-ylcarbamoyl}-1-methyl-1H-pyrazole-4-carboxylic acid ethyl ester

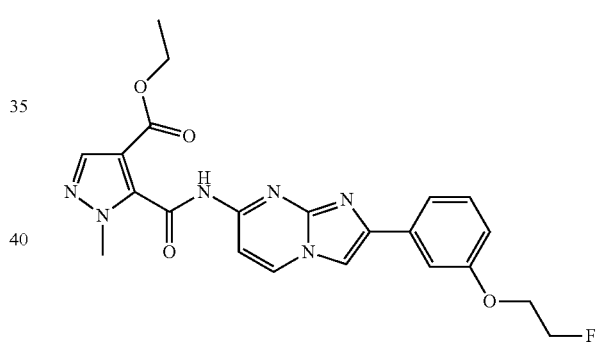

2-(3-(2-Fluoroethoxy)phenyl)imidazo[1,2-a]pyrimidin-7-amine (1 eq.) was combined with EtOAc (7.50 ml) to give a light yellow suspension. 4-(Ethoxycarbonyl)-1-methyl-1H-pyrazole-5-carboxylic acid (1 eq.) and DIPEA (6 eq.) were added. The reaction mixture was cooled down to 0° C. and n-propylphosphonic acid anhydride, cyclic trimer (1.17 g, 1.1 ml, 1.84 mmol, 2.50 eq.) was added dropwise. After stirring at 0° C. during 30 min, the reaction mixture was stirred and allowed to warm-up to RT overnight. The reaction mixture (yellow solution) was poured into 50 ml EtOAc and extracted with H$_2$O (1×30 ml). The aqueous layer was back-extracted with DCM (3×20 ml). The organic layers were combined and washed with sat. NaCl-solution (1×30 ml), dried over MgSO$_4$, filtrated and concentrated under vacuum to give a yellow solid (207 mg). The crude material was purified by flash chromatography (silica gel, 20 g, CH$_2$Cl$_2$ to 50% CH$_2$Cl$_2$/MeOH/NH$_3$ $_{aq.}$ 140:10:1). Yellow solid (332 mg, 31%).

MS (m/z)=453.2 [M+H+].

Step 2: 5-{2-[3-(2-Fluoro-ethoxy)-phenyl]-imidazo[1,2-a]pyrimidin-7-ylcarbamoyl}-1-methyl-1H-pyrazole-4-carboxylic acid

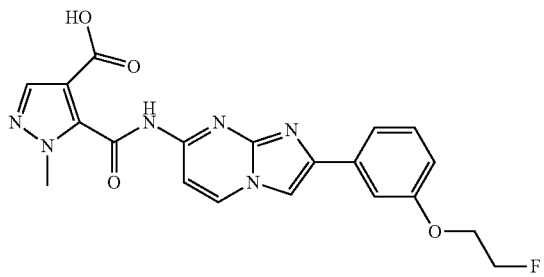 [SMILES: Cn1ncc(C(=O)O)c1C(=O)Nc1ccn2cc(-c3cccc(OCCF)c3)nc2n1]

Ethyl 5-(2-(3-(2-fluoro ethoxy)phenyl)imidazo[1,2-a]pyrimidin-7-ylcarbamoyl)-1-methyl-1H-pyrazole-4-carboxylate (100 mg, 221 µmol) was combined with Ethanol (0.570 ml) and THF (0.570) to give a yellow solution. The reaction was stirred at RT for 6 h. H₂O was added to the suspension and then HCl 1N was added until the mixture was acidic (pH=3). The suspension was stirred for 30 min and then the reaction mixture was filtered. The residual solvent was removed under vacuum. The title compound was obtained as a light yellow solid (73 mg, 78%).
MS (m/z)=425.2 [M+H+].

Step 3: 2-Methyl-2H-pyrazole-3,4-dicarboxylic acid 4-dimethylamide 3-({2-[3-(2-fluoro-ethoxy)-phenyl]-imidazo[1,2-a]pyrimidin-7-yl}-amide)

Dimethylamine hydrochloride (5.76 mg, 70.7 µmol) was combined with EtOAc (0.700 ml) to give a colorless solution. 5-(2-(3-(2-Fluoroethoxy)phenyl)imidazo[1,2-a]pyrimidin-7-ylcarbamoyl)-1-methyl-1H-pyrazole-4-carboxylic acid (30.0 mg, 70.7 µmol) and DIPEA (54.8 mg, 74.1 µl, 424 µmol) were added. The light yellow suspension was cooled down to 0° C., and n-propylphosphonic acid anhydride, cyclic trimer (112 mg, 177 µmol) was added dropwise. After stirring at 0° C. for 30 min, the reaction mixture was stirred and allowed to warm-up to RT overnight. After dilution with H₂O the product was extracted with EtOAc. Drying (MgSO₄) and evaporation of the solvent yielded the crude product. Purification by preparative TLC (silica gel, 1.0 mm, CH₂Cl₂/MeOH/NH₄OH 140:10:1) yielded the title compound (7.5 mg, 23%) as yellow solid. MS (m/z)=452.2 [M+H+].

Example 103

4-(Azetidine-1-carbonyl)-2-methyl-2H-pyrazole-3-carboxylic acid {2-[3-(2-fluoro-ethoxy)-phenyl]imidazo[1,2-a]pyrimidin-7-yl}-amide

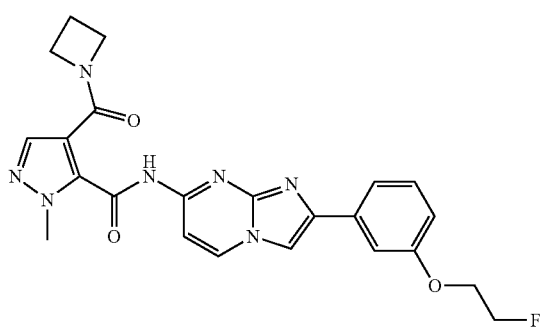 [SMILES: Cn1ncc(C(=O)N2CCC2)c1C(=O)Nc1ccn2cc(-c3cccc(OCCF)c3)nc2n1]

The title compound was prepared in analogy to example 102 from 2-[3-(2-Fluoro-ethoxy)-phenyl]-imidazo[1,2-c]pyrimidin-7-ylamine. Yellow solid. MS (m/z)=464.3 [M+H+].

Example 104

2-Methyl-2H-pyrazole-3,4-dicarboxylic acid 4-[(2-fluoro-ethyl)-methyl-amide]3-{[2-(3-fluoro-phenyl)-imidazo[1,2-a]pyrimidin-7-yl]-amide}

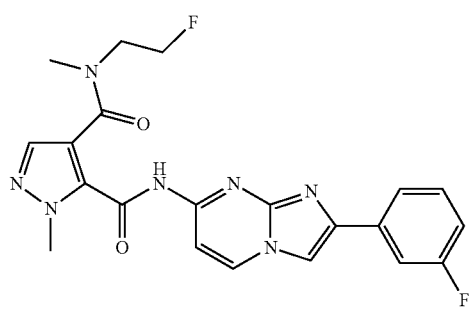 [SMILES: CN(CCF)C(=O)c1cnn(C)c1C(=O)Nc1ccn2cc(-c3cccc(F)c3)nc2n1]

The title compound was prepared in analogy to example 82 from 2-(3-fluorophenyl)imidazo[1,2-a]pyrimidin-7-amine (99 mg, 436 µmol) and 4-((2-fluoroethyl)(methyl)carbamoyl)-1-methyl-1H-pyrazole-5-carboxylic acid (100 mg, 436 µmol) Yellow solid (37 mg, 17%). MS (m/z)=440.2 [M+H+].

Example 105

3-(7-(4-(azetidine-1-carbonyl)-1-methyl-1H-pyrazole-5-carboxamido)imidazo[1,2-a]pyrimidin-2-yl) phenyl acetate

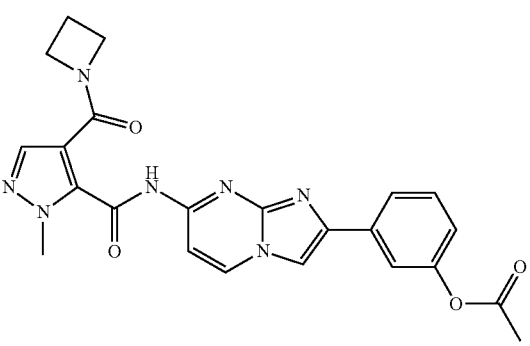 [SMILES: CC(=O)Oc1cccc(-c2cn3ccc(NC(=O)c4c(C(=O)N5CCC5)cnn4C)nc3n2)c1]

The title compound was prepared in analogy to example 82, step 3, from 4-(azetidine-1-carbonyl)-1-methyl-1H-pyrazole-5-carboxylic acid (156 mg, 746 µmol) and acetic acid 3-(7-amino-imidazo[1,2-c]pyrimidin-2-yl)-phenyl ester (200 mg, 746 µmol). Yield: 158 mg (42%). Yellow foam. MS (m/z)=459.2 [M+H+].

Example 106

2-Methyl-2H-pyrazole-3,4-dicarboxylic acid 4-{[2-(2-fluoro-ethoxy)-ethyl]-methyl-amide}3-[(2-phenyl-imidazo[1,2-a]pyrimidin-7-yl)-amide]

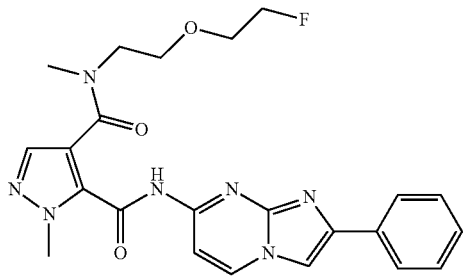 [SMILES: CN(CCOCCF)C(=O)c1cnn(C)c1C(=O)Nc1ccn2cc(-c3ccccc3)nc2n1]

The title compound was prepared in analogy to example 82 from 2-phenylimidazo[1,2-a]pyrimidin-7-amine (77, 366 µmol) and 4-((2-(2-fluoroethoxy)ethyl)(methyl)carbamoyl)-1-methyl-1H-pyrazole-5-carboxylic acid (100 mg, 366 µmol). Light yellow foam (15 mg, 8.1%). MS (m/z)=466.2 [M+H+].

Example 107

2-Methyl-2H-pyrazole-3,4-dicarboxylic acid 3-{[2-(3-fluoro-phenyl)-imidazo[1,2-a]pyrimidin-7-yl]-amide}4-[(2-methoxy-ethyl)-methyl-amide]

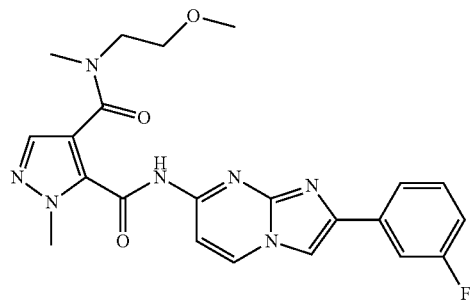 [SMILES: COCCN(C)C(=O)c1cnn(C)c1C(=O)Nc1ccn2cc(-c3cccc(F)c3)nc2n1]

The title compound was prepared in analogy to example 82 from 2-(3-fluorophenyl)imidazo[1,2-c]pyrimidin-7-amine (100 mg, 438 µmol) and 4-[(2-methyl-ethyl)-methyl-carbamoyl]-2-methyl-2H-pyrazole-3-carboxylic acid (127 mg, 526 µmol). Yellow solid (17 mg, 8%). MS (m/z)=452.2 [M+H+].

Example 108

2-Methyl-2H-pyrazole-3,4-dicarboxylic acid 4-[(2-fluoro-ethyl)-methyl-amide]3-{[2-(3-fluoromethoxy-phenyl)-imidazo[1,2-a]pyrimidin-7-yl]-amide}

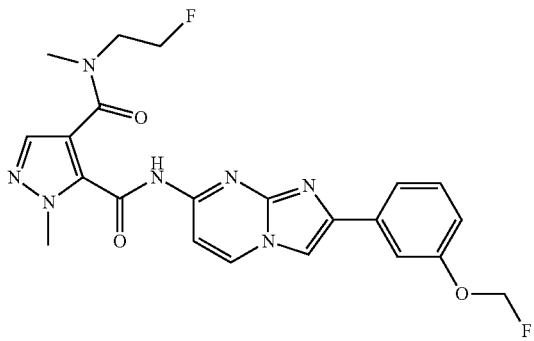 [SMILES: CN(CCF)C(=O)c1cnn(C)c1C(=O)Nc1ccn2cc(-c3cccc(OCF)c3)nc2n1]

The title compound was prepared in analogy to example 82 from 4-((2-fluoroethyl) (methyl)carbamoyl)-1-methyl-1H-pyrazole-5-carboxylic acid (89 mg, 387 µmol and 2-(3-(fluoromethoxy)phenyl)imidazo[1,2-a]pyrimidin-7-amine (100 mg, 387 µmol). Yellow solid (4.7 mg, 2%). MS (m/z)=470.1 [M+H+].

Example 109

2-Methyl-2H-pyrazole-3,4-dicarboxylic acid 4-{[2-(2-fluoro-ethoxy)-ethyl]-methyl-amide}3-({2-[3-(2-fluoro-ethoxy)-phenyl]-imidazo[1,2-a]pyrimidin-7-yl}-amide)

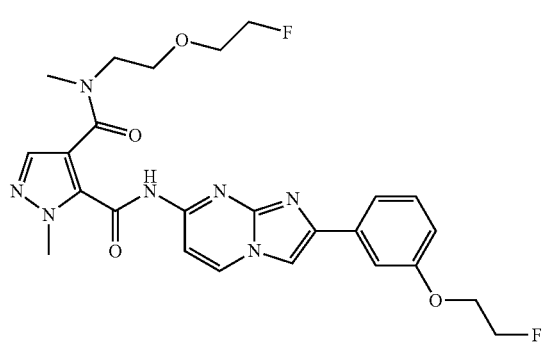 [SMILES: CN(CCOCCF)C(=O)c1cnn(C)c1C(=O)Nc1ccn2cc(-c3cccc(OCCF)c3)nc2n1]

The title compound was prepared in analogy to example 82 from 2-(3-(2-fluoroethoxy)phenyl)imidazo[1,2-a]pyrimidin-7-amine (100, 366 µmol) and 4-((2-(2-fluoroethoxy)ethyl) (methyl)carbamoyl)-1-methyl-1H-pyrazole-5-carboxylic acid (100 mg, 366 µmol). Light yellow foam (18 mg, 9%). MS (m/z)=528.2 [M+H+].

Example 110

2-Methyl-2H-pyrazole-3,4-dicarboxylic acid 4-{[2-(2-fluoro-ethoxy)-ethyl]-methyl-amide}3-{[2-(3-methoxy-phenyl-imidazo[1,2-a]pyrimidin-7-yl]-amide}

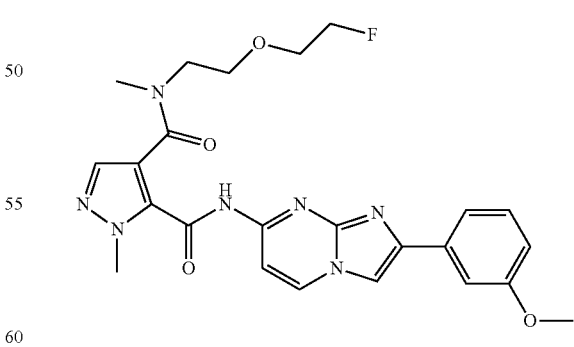

The title compound was prepared in analogy to example 82 from 2-(3-methoxyphenyl)imidazo[1,2-a]pyrimidin-7-amine (88, 366 µmol) and 4-((2-(2-fluoroethoxy)ethyl)(methyl)carbamoyl)-1-methyl-1H-pyrazole-5-carboxylic acid (100 mg, 366 µmol). Light yellow foam (36 mg, 19%). MS (m/z)=496.2 [M+H+].

Example 111

2-Methyl-2H-pyrazole-3,4-dicarboxylic acid 4-[(2-fluoro-ethyl)-methyl-amide]3-{[2-(3-methoxy-phenyl)-imidazo[1,2-a]pyrimidin-7-yl]amide}

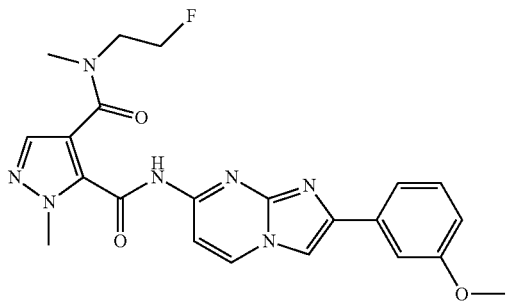 [SMILES: COc1cccc(-c2cn3ccc(NC(=O)c4c(C(=O)N(C)CCF)cnn4C)nc3n2)c1]

The title compound was prepared in analogy to example 82 from 2-(3-methoxyphenyl)imidazo[1,2-a]pyrimidin-7-amine (105, 436 μmol) and 4-((2-fluoroethyl)(methyl)carbamoyl)-1-methyl-1H-pyrazole-5-carboxylic acid (100 mg, 436 μmol). Color solid (17 mg, 9%). MS (m/z)=452.2 [M+H+].

Example 112

1-methyl-N4-(oxazol-4-ylmethyl)-N5-(2-phenylimidazo[1,2-a]pyrimidin-7-yl)-1H-pyrazole-4,5-dicarboxamide

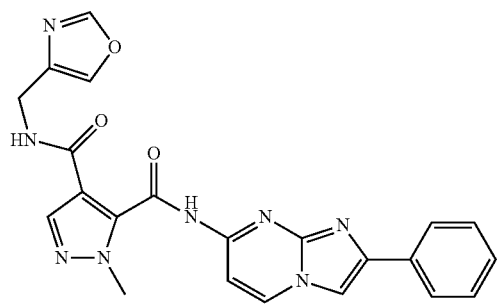 [SMILES: Cn1ncc(C(=O)NCc2cocn2)c1C(=O)Nc1ccn2cc(-c3ccccc3)nc2n1]

The title compound was obtained in analogy to example 29, using C-oxazol-4-yl-methylamine in the last step. MS (m/e)=443.3 [M+H+].

Example 113

N4-((1H-pyrazol-5-yl)methyl)-1-methyl-N5-(2-phenylimidazo[1,2-a]pyrimidin-7-yl)-1H-pyrazole-4,5-dicarboxamide

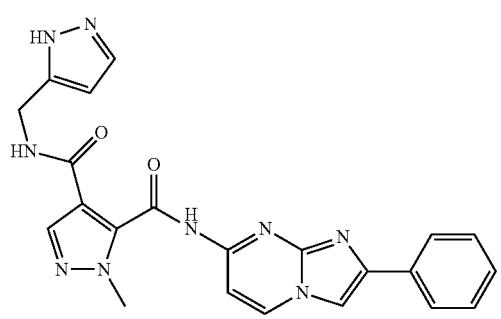 [SMILES: Cn1ncc(C(=O)NCc2ccn[nH]2)c1C(=O)Nc1ccn2cc(-c3ccccc3)nc2n1]

The title compound was obtained in analogy to example 29, using C-(2H-pyrazol-3-yl)-methylamine in the last step. MS (m/e)=442.3 [M+H+].

Example 114

4-(2,5-dihydro-1H-pyrrole-1-carbonyl)-1-methyl-N-(2-phenylimidazo[1,2-a]pyrimidin-7-yl)-1H-pyrazole-5-carboxamide

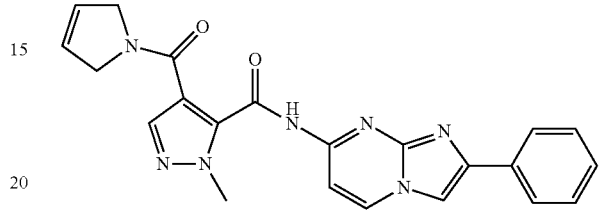

The title compound was obtained in analogy to example 29, using 2,5-dihydro-1H-pyrrole in the last step. MS (m/e)=414.3 [M−H+].

Example 115

4-(3-fluoroazetidine-1-carbonyl)-1-methyl-N-(2-phenylimidazo[1,2-a]pyrimidin-7-yl)-1H-pyrazole-5-carboxamide

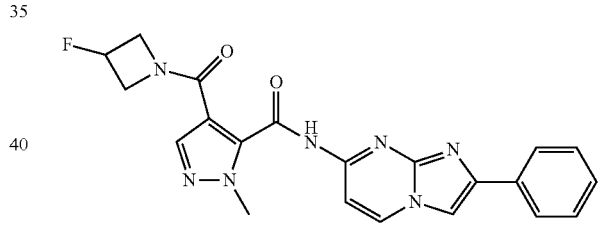

The title compound was obtained in analogy to example 29, using 3-fluoro-azetidine in the last step. MS (m/e)=420.2 [M+H+].

Example 116

1-methyl-4-(2-methylpyrrolidine-1-carbonyl)-N-(2-phenylimidazo[1,2-a]pyrimidin-7-yl)-1H-pyrazole-5-carboxamide

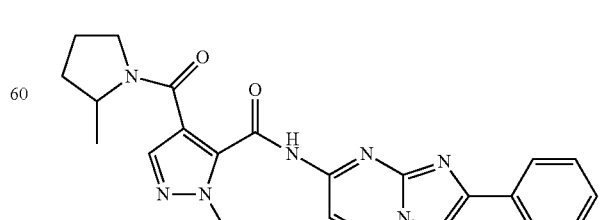

The title compound was obtained in analogy to example 29, using 2-methyl-pyrrolidine in the last step. MS (m/e)=430.3 [M+H⁺].

Example 117

4-(azetidine-1-carbonyl)-N-(2-(3-bromophenyl)imidazo[1,2-a]pyrimidin-7-yl)-1-methyl-1H-pyrazole-5-carboxamide

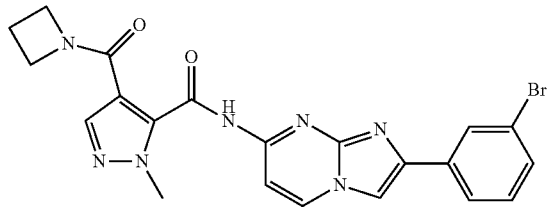 [SMILES: Cn1ncc(C(=O)N2CCC2)c1C(=O)Nc1ccn2cc(-c3cccc(Br)c3)nc2n1]

The title compound was obtained in analogy to example 29, using 2-(3-bromo-phenyl)-imidazo[1,2-a]pyrimidin-7-ylamine in step 4. 2-(3-Bromo-phenyl)-imidazo[1,2-a]pyrimidin-7-ylamine was prepared in analogy to example 1, step 1, from 2-bromo-1-(3-chloro-phenyl)-ethanone. MS (m/e)=480.2 [M+H⁺].

Example 118

1-methyl-N5-(2-phenylimidazo[1,2-a]pyrimidin-7-yl)-N4-(pyridin-2-ylmethyl)-1H-pyrazole-4,5-dicarboxamide

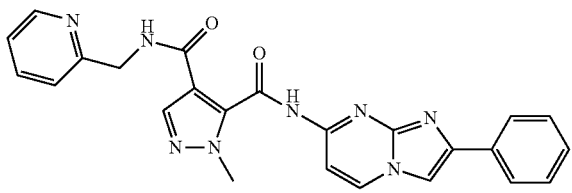 [SMILES: Cn1ncc(C(=O)NCc2ccccn2)c1C(=O)Nc1ccn2cc(-c3ccccc3)nc2n1]

The title compound was obtained in analogy to example 29, using C-pyridin-2-yl-methylamine in the last step. MS (m/e)=453.2 [M+H⁺].

Example 119

N4-(cyanomethyl)-N4,1-dimethyl-N5-(2-phenylimidazo[1,2-a]pyrimidin-7-yl)-1H-pyrazole-4,5-dicarboxamide

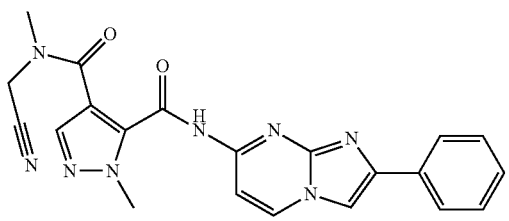 [SMILES: CN(CC#N)C(=O)c1cnn(C)c1C(=O)Nc1ccn2cc(-c3ccccc3)nc2n1]

The title compound was obtained in analogy to example 29, using methylamino-acetonitrile in the last step. MS (m/e)=415.3 [M+H⁺].

Example 120

1-allyl-4-(azetidine-1-carbonyl)-N-(2-phenylimidazo[1,2-a]pyrimidin-7-yl)-1H-pyrazole-5-carboxamide

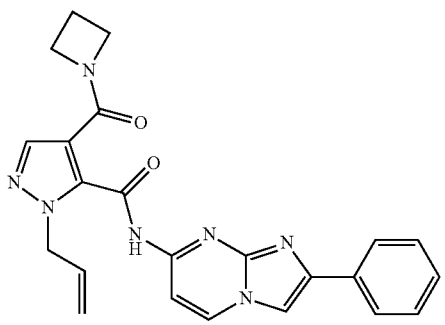 [SMILES: C=CCn1ncc(C(=O)N2CCC2)c1C(=O)Nc1ccn2cc(-c3ccccc3)nc2n1]

The title compound was obtained in analogy to example 64 from 2-allyl-2H-pyrazole-3,4-dicarboxylic acid 4-ethyl ester (step 1) and azetidine (step 2). 2-Allyl-2H-pyrazole-3,4-dicarboxylic acid 4-ethyl ester was prepared in analogy to example 62, using allyl bromide in step 2. MS (m/e)=428.3 [M+H⁺].

Example 121

1-methyl-N-4-((5-methyl-1H-pyrazol-3-yl)methyl)-N5-(2-phenylimidazo[1,2-a]pyrimidin-7-yl)-1H-pyrazole-4,5-dicarboxamide

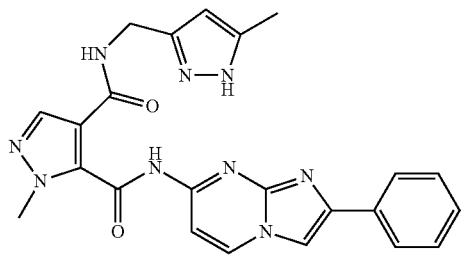 [SMILES: Cc1cc(CNC(=O)c2cnn(C)c2C(=O)Nc2ccn3cc(-c4ccccc4)nc3n2)n[nH]1]

The title compound was obtained in analogy to example 29, using C-(5-methyl-1H-pyrazol-3-yl)-methyl amine in the last step. MS (m/e)=456.4 [M+H⁺].

Example 122

1-methyl-N4-(oxazol-2-ylmethyl)-N5-(2-phenylimidazo[1,2-a]pyrimidin-7-yl)-1H-pyrazole-4,5-dicarboxamide

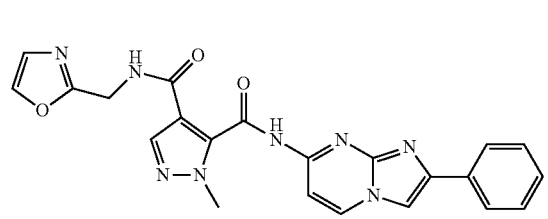 [SMILES: Cn1ncc(C(=O)NCc2ncco2)c1C(=O)Nc1ccn2cc(-c3ccccc3)nc2n1]

The title compound was obtained in analogy to example 29, using C-oxazol-2-yl-methylamine in the last step. MS (m/e)=443.3 [M+H⁺].

Example 123

N4-(2-fluoroethyl)-1-methyl-N5-(2-phenylimidazo[1,2-a]pyrimidin-7-yl)-1H-pyrazole-4,5-dicarboxamide

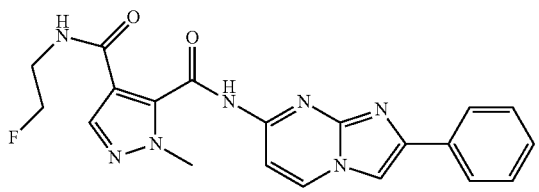 [SMILES: Cn1ncc(C(=O)NCCF)c1C(=O)Nc1ccn2cc(-c3ccccc3)nc2n1]

The title compound was obtained in analogy to example 29, using 2-fluoro-ethylamine in the last step. MS (m/e)=408.3 [M+H$^+$].

Example 124

1-methyl-N4-((5-methylthiazol-2-yl)methyl)-N5-(2-phenylimidazo[1,2-a]pyrimidin-7-yl)-1H-pyrazole-4,5-dicarboxamide

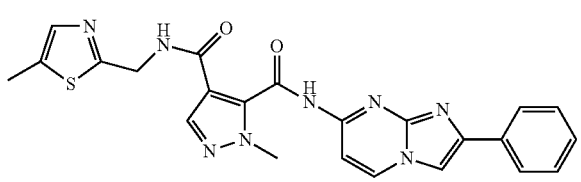 [SMILES: Cc1cnc(CNC(=O)c2cnn(C)c2C(=O)Nc2ccn3cc(-c4ccccc4)nc3n2)s1]

The title compound was obtained in analogy to example 29, using C-(5-methyl-thiazol-2-yl)-methylamine in the last step. MS (m/e)=473.2 [M+H$^+$].

Example 125

N4-(cyanomethyl)-1-methyl-N5-(2-phenylimidazo[1,2-a]pyrimidin-7-yl)-1H-pyrazole-4,5-dicarboxamide

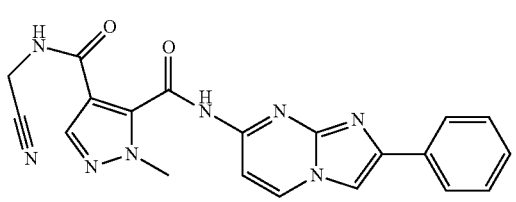 [SMILES: Cn1ncc(C(=O)NCC#N)c1C(=O)Nc1ccn2cc(-c3ccccc3)nc2n1]

The title compound was obtained in analogy to example 29, using amino-acetonitrile in the last step. MS (m/e)=401.3 [M+H$^+$].

Example 126

1-methyl-N5-(2-phenylimidazo[1,2-a]pyrimidin-7-yl)-N4-(3,3,3-trifluoropropyl)-1H-pyrazole-4,5-dicarboxamide

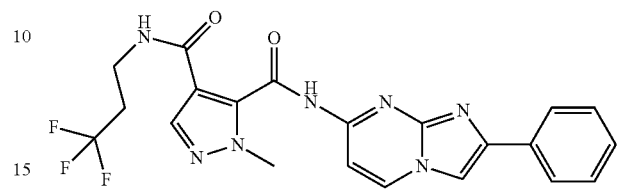

The title compound was obtained in analogy to example 29, using 3,3,3-trifluoro-propylamine in the last step. MS (m/e)=458.2 [M+H$^+$].

Example 127

1-methyl-N4-((3-methylisoxazol-5-yl)methyl)-N5-(2-phenylimidazo[1,2-a]pyrimidin-7-yl)-1H-pyrazole-4,5-dicarboxamide

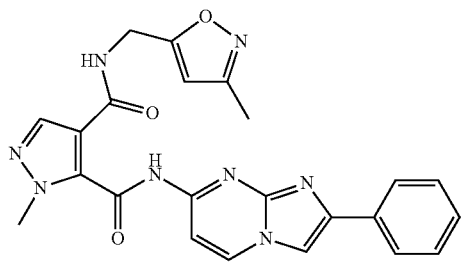 [SMILES: Cc1cc(CNC(=O)c2cnn(C)c2C(=O)Nc2ccn3cc(-c4ccccc4)nc3n2)on1]

The title compound was obtained in analogy to example 29, using C-(3-methyl-isoxazol-5-yl)-methylamine in the last step. MS (m/e)=457.3 [M+H$^+$].

Example 128

4-(azetidine-1-carbonyl)-N-(2-(biphenyl-3-yl)imidazo[1,2-a]pyrimidin-7-yl)-1-methyl-1H-pyrazole-5-carboxamide

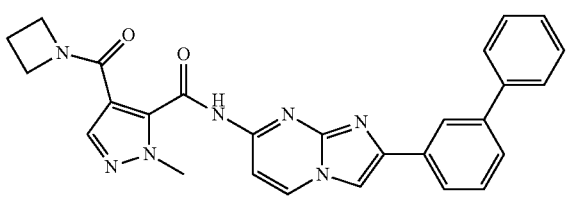 [SMILES: Cn1ncc(C(=O)N2CCC2)c1C(=O)Nc1ccn2cc(-c3cccc(-c4ccccc4)c3)nc2n1]

Under an atmosphere of argon, in a 25 mL round-bottomed flask, 4-(azetidine-1-carbonyl)-N-(2-(3-bromophenyl)imidazo[1,2-a]pyrimidin-7-yl)-1-methyl-1H-pyrazole-5-carboxamide (85 mg, 177 µmol, Eq: 1.00, example 117), phenylboronic acid (43.2 mg, 354 μmol, Eq: 2), 1,1'-bis(diphenylphosphino)ferrocene-palladium(II) dichloride dichloromethane complex (14.5 mg, 17.7 μmol, Eq: 0.1) and potassium carbonate (73.4 mg, 531 μmol, Eq: 3) were combined with DMF (2 ml) and water (0.2 ml) to give a brown solution. The reaction was stirred for 1 h at 100° C. The HPLC-MS showed complete conversion. The reaction mixture was poured into 20 mL water and extracted with EtOAc (2×25 mL). The organic layers were dried over $Na_2SO_4$ and concentrated in vacuo. After the addition of 2 ml Methanol the desired product crystallized. The suspension was filtered off and washed with 0.5 ml MeOH. The residual solvent was removed under vacuum. The title compound was obtained as a light brown solid (42 mg, 49.7%). 4-(Azetidine-1-carbonyl)-N-(2-(3-bromophenyl)imidazo[1,2-a]pyrimidin-7-yl)-1-methyl-1H-pyrazole-5-carboxamide was prepared in analogy to example 29, using 2-(3-bromo-phenyl)-imidazo[1,2-a]pyrimidin-7-ylamine in the first step. 2-(3-Bromo-phenyl)-imidazo[1,2-a]pyrimidin-7-ylamine can be prepared in analogy to example 1, step 1, from 2-bromo-1-(3-bromo-phenyl)-ethanone.

MS (m/e)=478.2 [M+H⁺].

Example 129

N4-(2,2-difluoroethyl)-1-methyl-N5-(2-phenylimidazo[1,2-a]pyrimidin-7-yl)-1H-pyrazole-4,5-dicarboxamide

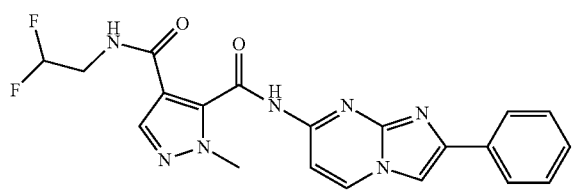 [SMILES: Cn1ncc(C(=O)NCC(F)F)c1C(=O)Nc1ccn2cc(-c3ccccc3)nc2n1]

The title compound was obtained in analogy to example 29, using 2,2-difluoro-ethylamine in the last step. MS (m/e)=426.1 [M+H⁺].

Example 130

1-methyl-N5-(2-phenylimidazo[1,2-a]pyrimidin-7-yl)-N4-(2,2,2-trifluoroethyl)-1H-pyrazole-4,5-dicarboxamide

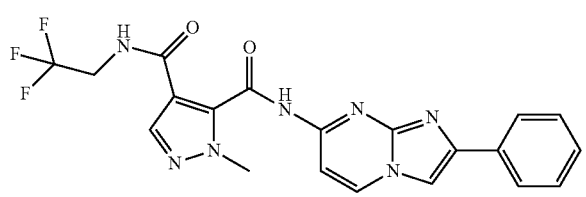 [SMILES: Cn1ncc(C(=O)NCC(F)(F)F)c1C(=O)Nc1ccn2cc(-c3ccccc3)nc2n1]

The title compound was obtained in analogy to example 29, using 2,2,2-trifluoro-ethylamine in the last step. MS (m/e)=444.2 [M+H⁺].

Example 131

N4-(isoxazol-5-ylmethyl)-1-methyl-N5-(2-phenylimidazo[1,2-a]pyrimidin-7-yl)-1H-pyrazole-4,5-dicarboxamide

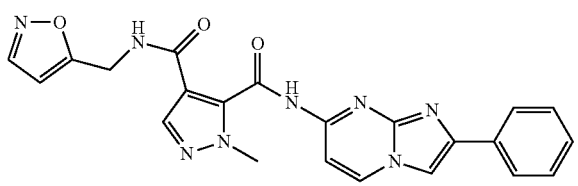 [SMILES: Cn1ncc(C(=O)NCc2ccno2)c1C(=O)Nc1ccn2cc(-c3ccccc3)nc2n1]

The title compound was obtained in analogy to example 29, using C-isoxazol-5-yl-methylamine in the last step. MS (m/e)=443.4 [M+H⁺].

Example 132

1-methyl-N-(2-phenylimidazo[1,2-a]pyrimidin-7-yl)-4-(2-oxa-6-azaspiro[3.3]heptane-6-carbonyl)-1H-pyrazole-5-carboxamide

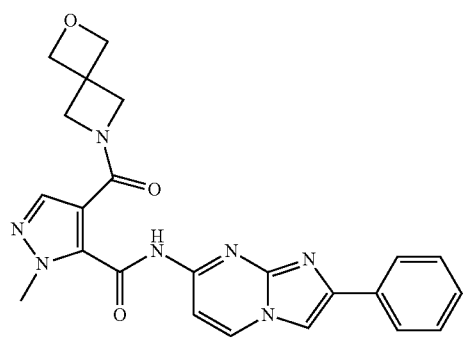 [SMILES: Cn1ncc(C(=O)N2CC3(COC3)C2)c1C(=O)Nc1ccn2cc(-c3ccccc3)nc2n1]

The title compound was obtained in analogy to example 29, using 2-oxa-6-aza-spiro[3.3]heptane in the last step. MS (m/e)=444.3 [M+H⁺].

Example 133

1-methyl-N4-phenyl-N5-(2-phenylimidazo[1,2-a]pyrimidin-7-yl)-1H-pyrazole-4,5-dicarboxamide

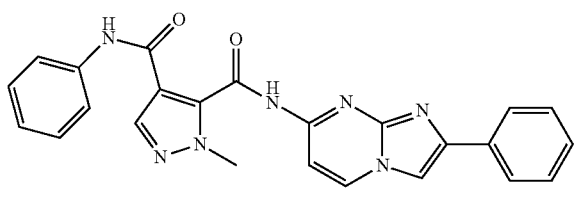 [SMILES: Cn1ncc(C(=O)Nc2ccccc2)c1C(=O)Nc1ccn2cc(-c3ccccc3)nc2n1]

The title compound was obtained in analogy to example 29, using aniline in the last step. MS (m/e)=438.2 [M+H⁺].

Example 134

1-methyl-N4-(3-methyloxetan-3-yl)-N5-(2-phenylimidazo[1,2-a]pyrimidin-7-yl)-1H-pyrazole-4,5-dicarboxamide

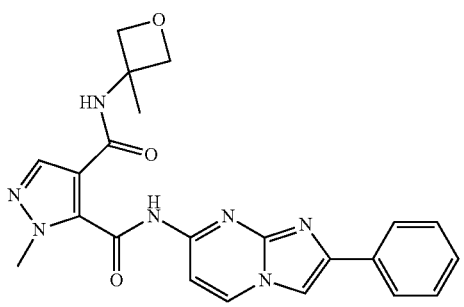 [SMILES: Cn1ncc(C(=O)NC2(C)COC2)c1C(=O)Nc1ccn2cc(-c3ccccc3)nc2n1]

The title compound was obtained in analogy to example 29, using 3-methyl-oxetan-3-ylamine in the last step. MS (m/e)=432.3 [M+H⁺].

Example 135

N4,1-dimethyl-N5-(2-phenylimidazo[1,2-a]pyrimidin-7-yl)-N4-(pyridin-2-ylmethyl)-1H-pyrazole-4,5-dicarboxamide

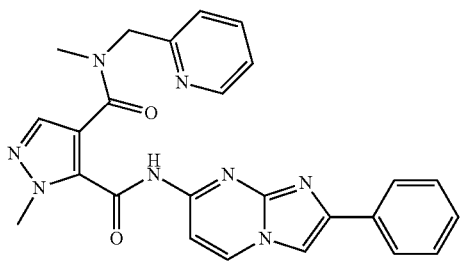 [SMILES: CN(Cc1ccccn1)C(=O)c1cnn(C)c1C(=O)Nc1ccn2cc(-c3ccccc3)nc2n1]

The title compound was obtained in analogy to example 29, using methyl-pyridin-2-ylmethyl-amine in the last step. MS (m/e)=467.3 [M+H⁺].

Example 136

N4-((5-bromopyridin-2-yl)methyl)-N4,1-dimethyl-N5-(2-phenylimidazo[1,2-a]pyrimidin-7-yl)-1H-pyrazole-4,5-dicarboxamide

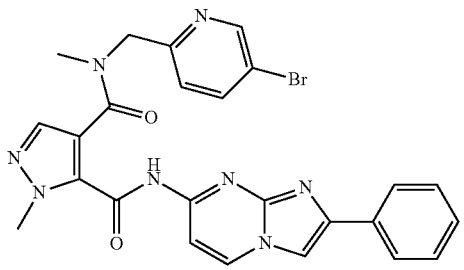 [SMILES: CN(Cc1ccc(Br)cn1)C(=O)c1cnn(C)c1C(=O)Nc1ccn2cc(-c3ccccc3)nc2n1]

The title compound was obtained in analogy to example 29, using (5-bromo-pyridin-2-ylmethyl)-methyl-amine in the last step. MS (m/e)=547.1 [M+H⁺].

Example 137

1-methyl-N-(2-phenylimidazo[1,2-a]pyrimidin-7-yl)-4-(3-(pyridin-3-yl)morpholine-4-carbonyl)-1H-pyrazole-5-carboxamide

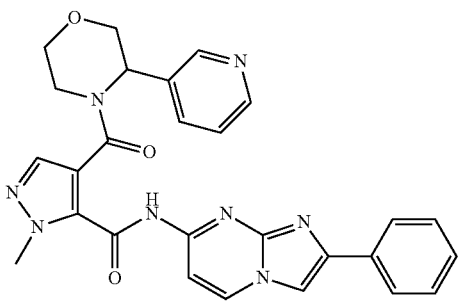 [SMILES: Cn1ncc(C(=O)N2CCOCC2c2cccnc2)c1C(=O)Nc1ccn2cc(-c3ccccc3)nc2n1]

The title compound was obtained in analogy to example 29, using 3-pyridin-3-yl-morpholine in the last step. MS (m/e)=509.4 [M+H⁺].

Example 138

N4-tert-butyl-1-methyl-N5-(2-phenylimidazo[1,2-a]pyrimidin-7-yl)-1H-pyrazole-4,5-dicarboxamide

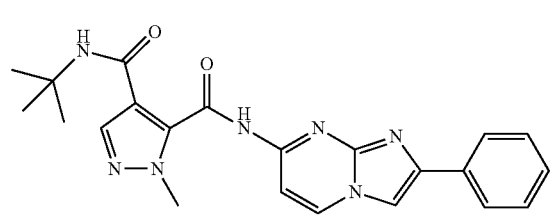 [SMILES: Cn1ncc(C(=O)NC(C)(C)C)c1C(=O)Nc1ccn2cc(-c3ccccc3)nc2n1]

The title compound was obtained in analogy to example 29, using tert-butylamine in the last step. MS (m/e)=418.3 [M+H⁺].

Example 139

1-methyl-N5-(2-phenylimidazo[1,2-a]pyrimidin-7-yl)-N4-(1-(pyridin-3-yl)ethyl)-1H-pyrazole-4,5-dicarboxamide

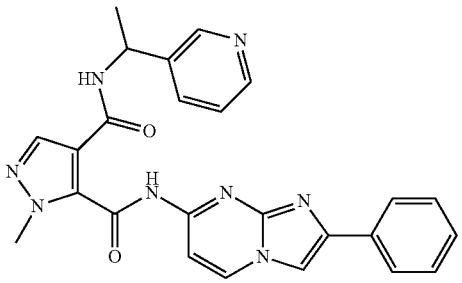 [SMILES: CC(NC(=O)c1cnn(C)c1C(=O)Nc1ccn2cc(-c3ccccc3)nc2n1)c1cccnc1]

The title compound was obtained in analogy to example 29, using methyl-(1-pyridin-3-yl-ethyl)-amine in the last step. MS (m/e)=467.3 [M+H⁺].

Example 140

N4-((1,3-dimethyl-4-nitro-1H-pyrazol-5-yl)methyl)-1-methyl-N5-(2-phenylimidazo[1,2-a]pyrimidin-7-yl)-1H-pyrazole-4,5-dicarboxamide

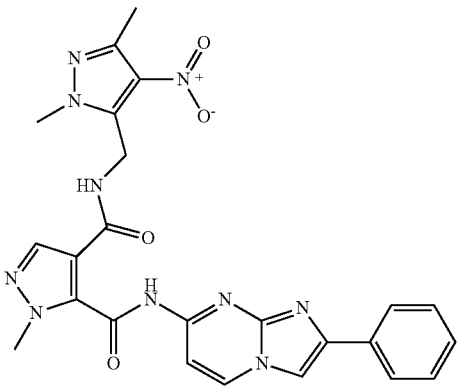

The title compound was obtained in analogy to example 29, using C-(2,5-dimethyl-4-nitro-2H-pyrazol-3-yl)-methylamine in the last step. MS (m/e)=515.3 [M+H$^+$].

Example 141

N5-(oxetan-3-yl)-N4-(2-phenylimidazo[1,2-a]pyrimidin-7-yl)-1H-1,2,3-triazole-4,5-dicarboxamide

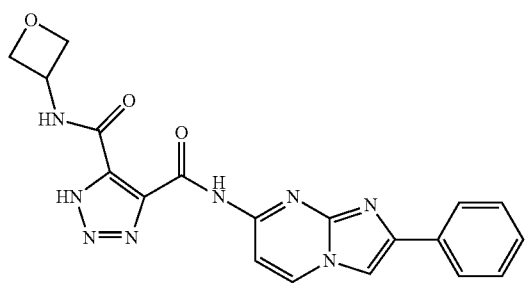 [SMILES: O=C(Nc1ccn2cc(-c3ccccc3)nc2n1)c1nn[nH]c1C(=O)NC1COC1]

The title compound was obtained in analogy to example 29, using oxetan-3-ylamine in the last step. MS (m/e)=405.3 [M+H$^+$].

Example 142

N4-((6-cyanopyridin-3-yl)methyl)-1-methyl-N5-(2-phenylimidazo[1,2-a]pyrimidin-7-yl)-1H-pyrazole-4,5-dicarboxamide

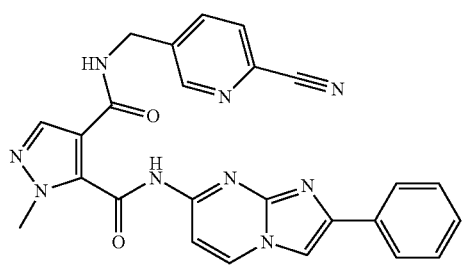 [SMILES: Cn1ncc(C(=O)NCc2ccc(C#N)nc2)c1C(=O)Nc1ccn2cc(-c3ccccc3)nc2n1]

The title compound was obtained in analogy to example 29, using 5-aminomethyl-pyridine-2-carbonitrile in the last step. MS (m/e)=490.3 [M+H$^+$].

Example 143

1-methyl-N-4-((5-methylisoxazol-3-yl)methyl)-N5-(2-phenylimidazo[1,2-a]pyrimidin-7-yl)-1H-pyrazole-4,5-dicarboxamide

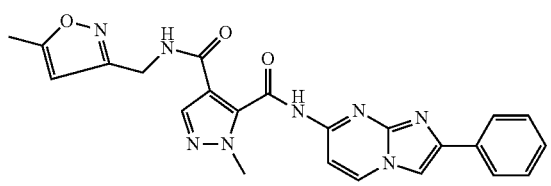 [SMILES: Cc1cc(CNC(=O)c2cnn(C)c2C(=O)Nc2ccn3cc(-c4ccccc4)nc3n2)no1]

The title compound was obtained in analogy to example 29, using C-(5-methyl-isoxazol-3-yl)-methylamine in the last step. MS (m/e)=457.3 [M+H$^+$].

Example 144

1-methyl-N5-(2-phenylimidazo[1,2-a]pyrimidin-7-yl)-N-4-((6-(trifluoromethyl)pyridin-3-yl)methyl)-1H-pyrazole-4,5-dicarboxamide

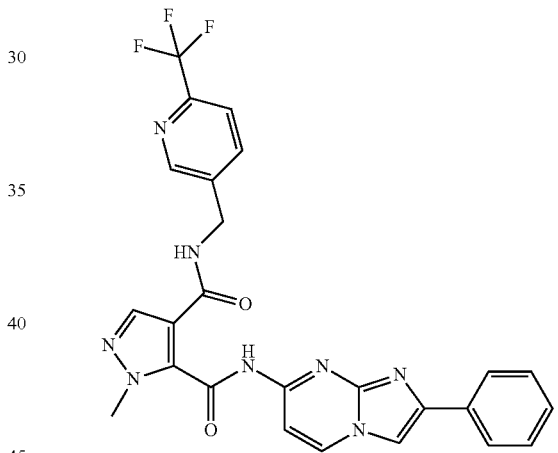

The title compound was obtained in analogy to example 29, using C-(6-trifluoromethyl-pyridin-3-yl)-methylamine in the last step. MS (m/e)=521.3 [M+H$^+$].

Example 145

N4-(1-cyanocyclopropyl)-1-methyl-N5-(2-phenylimidazo[1,2-a]pyrimidin-7-yl)-1H-pyrazole-4,5-dicarboxamide

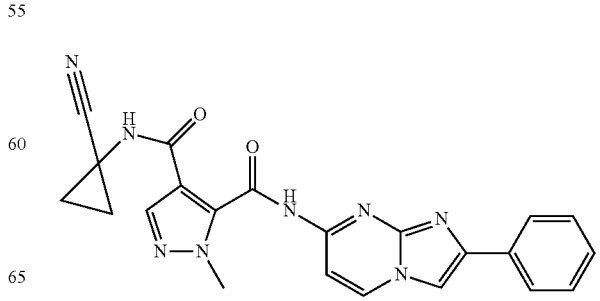

The title compound was obtained in analogy to example 29, using 1-amino-cyclopropanecarbonitrile in the last step. MS (m/e)=427.2 [M+H$^+$].

Example 146

N4-(isoxazol-3-ylmethyl)-1-methyl-N5-(2-phenylimidazo[1,2-a]pyrimidin-7-yl)-1H-pyrazole-4,5-dicarboxamide

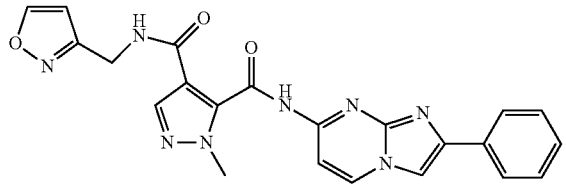 [SMILES: Cn1ncc(C(=O)NCc2ccon2)c1C(=O)Nc1ccn2cc(-c3ccccc3)nc2n1]

The title compound was obtained in analogy to example 29, using C-isoxazol-3-yl-methylamine in the last step. MS (m/e)=443.3 [M+H$^+$].

Example 147

N4-((1H-tetrazol-5-yl)methyl)-1-methyl-N5-(2-phenylimidazo[1,2-a]pyrimidin-7-yl)-1H-pyrazole-4,5-dicarboxamide

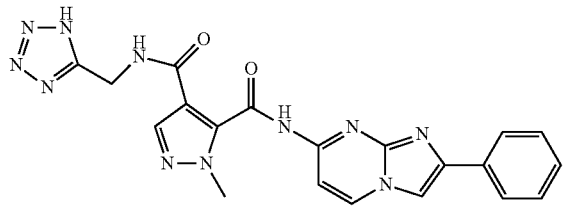 [SMILES: Cn1ncc(C(=O)NCc2nnn[nH]2)c1C(=O)Nc1ccn2cc(-c3ccccc3)nc2n1]

The title compound was obtained in analogy to example 29, using C-(1H-tetrazol-5-yl)-methylamine in the last step. MS (m/e)=444.4 [M+H$^+$].

Example 148

1-methyl-N5-(2-phenylimidazo[1,2-a]pyrimidin-7-yl)-N4-(pyridin-4-ylmethyl)-1H-pyrazole-4,5-dicarboxamide

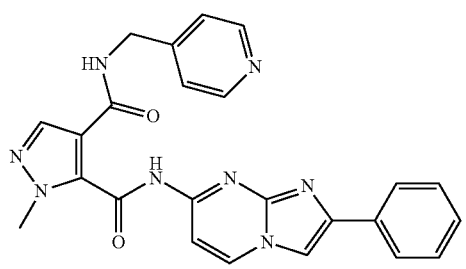 [SMILES: Cn1ncc(C(=O)NCc2ccncc2)c1C(=O)Nc1ccn2cc(-c3ccccc3)nc2n1]

The title compound was obtained in analogy to example 29, using C-pyridin-4-yl-methylamine in the last step. MS (m/e)=453.3 [M+H$^+$].

Example 149

N4-(imidazo[1,2-a]pyridin-2-ylmethyl)-1-methyl-N5-(2-phenylimidazo[1,2-a]pyrimidin-7-yl)-1H-pyrazole-4,5-dicarboxamide

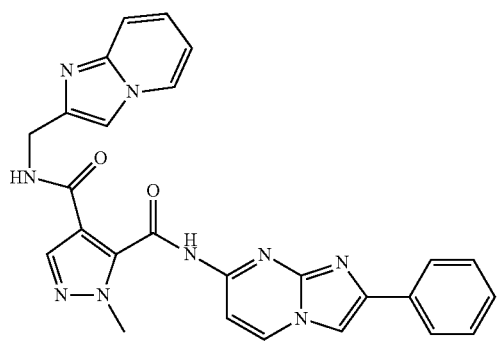 [SMILES: Cn1ncc(C(=O)NCc2cn3ccccc3n2)c1C(=O)Nc1ccn2cc(-c3ccccc3)nc2n1]

Example 150

N5-(2-methoxyethyl)-N4-(2-phenylimidazo[1,2-a]pyrimidin-7-yl)-1H-1,2,3-triazole-4,5-dicarboxamide

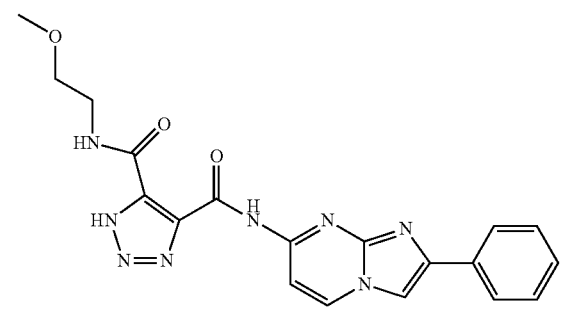 [SMILES: COCCNC(=O)c1[nH]nnc1C(=O)Nc1ccn2cc(-c3ccccc3)nc2n1]

Example 151

N4-((4-cyanothiazol-2-yl)methyl)-1-methyl-N5-(2-phenylimidazo[1,2-a]pyrimidin-7-yl)-1H-pyrazole-4,5-dicarboxamide

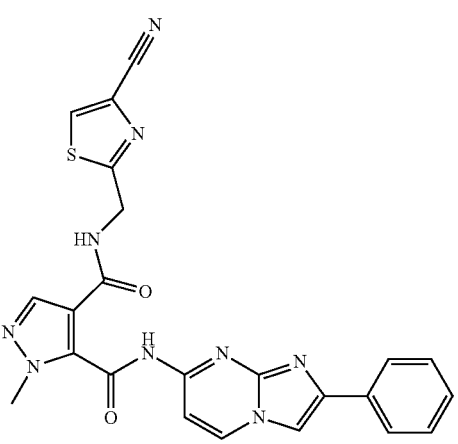 [SMILES: Cn1ncc(C(=O)NCc2nc(C#N)cs2)c1C(=O)Nc1ccn2cc(-c3ccccc3)nc2n1]

The title compound was obtained in analogy to example 29, using 2-aminomethyl-thiazole-4-carbonitrile in the last step. MS (m/e)=484.3 [M+H⁺].

Example 152

N4-((5-cyclopropyl-1H-pyrazol-3-yl)methyl)-1-methyl-N5-(2-phenylimidazo[1,2-a]pyrimidin-7-yl)-1H-pyrazole-4,5-dicarboxamide

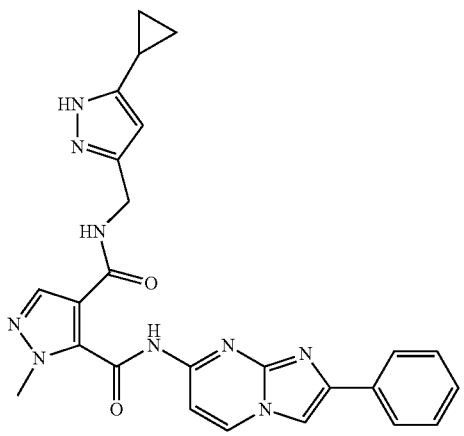 [SMILES: Cn1ncc(C(=O)NCc2cc(C3CC3)[nH]n2)c1C(=O)Nc1ccn2cc(-c3ccccc3)nc2n1]

The title compound was obtained in analogy to example 29, using C-(5-cyclopropyl-1H-pyrazol-3-yl)-methylamine in the last step. MS (m/e)=456.4 [M+H⁺].

Example 153

N4-(imidazo[2,1-b]thiazol-6-ylmethyl)-1-methyl-N5-(2-phenylimidazo[1,2-a]pyrimidin-7-yl)-1H-pyrazole-4,5-dicarboxamide

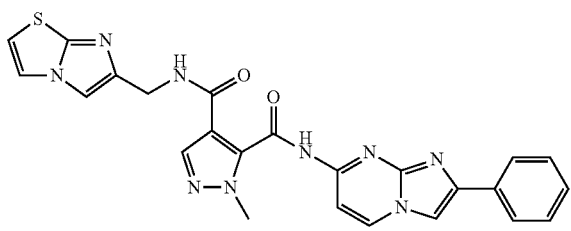 [SMILES: Cn1ncc(C(=O)NCc2cn3ccsc3n2)c1C(=O)Nc1ccn2cc(-c3ccccc3)nc2n1]

The title compound was obtained in analogy to example 29, using C-imidazo[2,1-b]thiazol-6-yl-methyl amine in the last step. MS (m/e)=498.4 [M+H⁺].

Example 154

N4-((6-chloropyridin-3-yl)methyl)-1-methyl-N5-(2-phenylimidazo[1,2-a]pyrimidin-7-yl)-1H-pyrazole-4,5-dicarboxamide

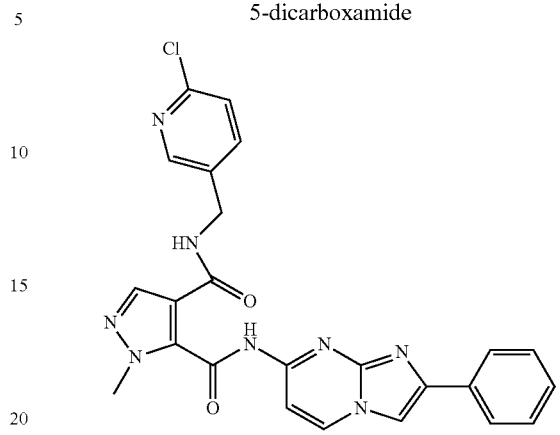

The title compound was obtained in analogy to example 29, using C-(6-chloro-pyridin-3-yl)-methylamine in the last step. MS (m/e)=487.3 [M+H⁺].

Example 155

1-methyl-N4-((5-methylpyridin-2-yl)methyl)-N5-(2-phenylimidazo[1,2-a]pyrimidin-7-yl)-1H-pyrazole-4,5-dicarboxamide

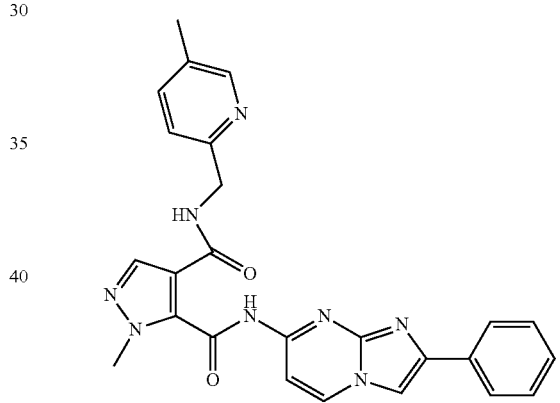

The title compound was obtained in analogy to example 29, using C-(5-methyl-pyridin-2-yl)-methylamine in the last step. MS (m/e)=467.3 [M+H⁺].

Example 156

N4-(2-phenylimidazo[1,2-a]pyrimidin-7-yl)-N5-propyl-1H-1,2,3-triazole-4,5-dicarboxamide

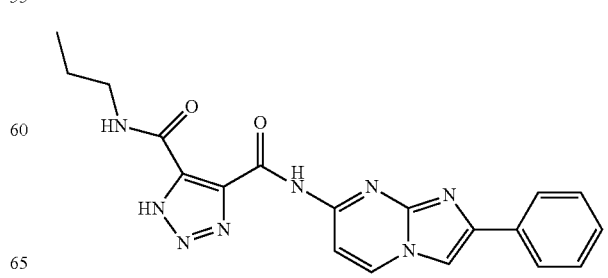

The title compound was obtained in analogy to example 27, using propylamine in the last step. MS (m/e)=391.2 [M+H⁺].

Example 157

1-methyl-N-4-((1-methyl-1H-pyrazol-3-yl)methyl)-N5-(2-phenylimidazo[1,2-a]pyrimidin-7-yl)-1H-pyrazole-4,5-dicarboxamide

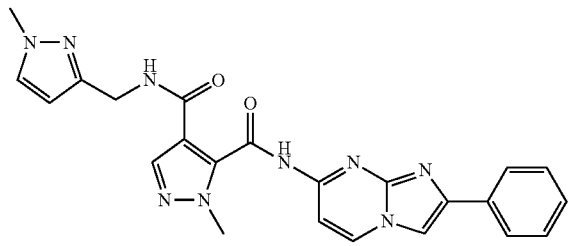 [SMILES: Cn1ccc(CNC(=O)c2cnn(C)c2C(=O)Nc2ccn3cc(-c4ccccc4)nc3n2)n1]

The title compound was obtained in analogy to example 29, using C-(1-methyl-1H-pyrazol-3-yl)-methylamine in the last step. MS (m/e)=456.3 [M+H⁺].

Example 158

N4-((4-chloro-1-methyl-1H-pyrazol-3-yl)methyl)-1-methyl-N5-(2-phenylimidazo[1,2-a]pyrimidin-7-yl)-1H-pyrazole-4,5-dicarboxamide

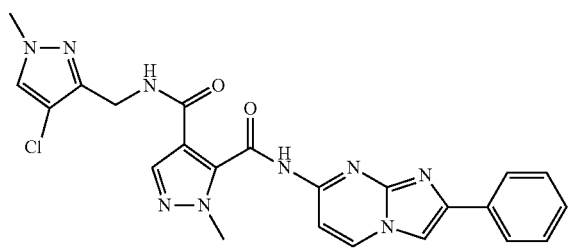 [SMILES: Cn1cc(Cl)c(CNC(=O)c2cnn(C)c2C(=O)Nc2ccn3cc(-c4ccccc4)nc3n2)n1]

The title compound was obtained in analogy to example 29, using C-(4-chloro-1-methyl-1H-pyrazol-3-yl)-methylaminein the last step. MS (m/e)=490.3 [M+H⁺].

Example 159

N5-cyclopropyl-N4-(2-phenylimidazo[1,2-a]pyrimidin-7-yl)-1H-1,2,3-triazole-4,5-dicarboxamide

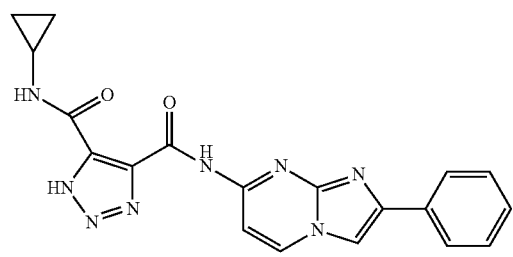 [SMILES: O=C(Nc1ccn2cc(-c3ccccc3)nc2n1)c1nn[nH]c1C(=O)NC1CC1]

The title compound was obtained in analogy to example 27, using cyclopropylamine in the last step. MS (m/e)=391.2 [M+H⁺].

Example 160

N4-((3-ethylisoxazol-5-yl)methyl)-1-methyl-N5-(2-phenylimidazo[1,2-a]pyrimidin-7-yl)-1H-pyrazole-4,5-dicarboxamide

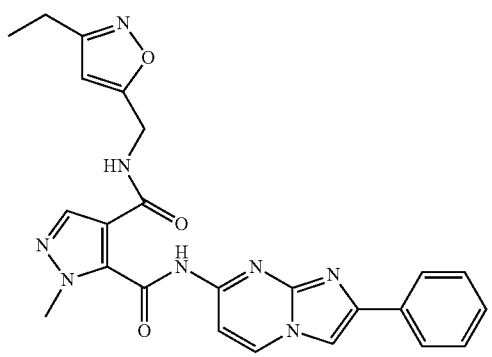 [SMILES: CCc1cc(CNC(=O)c2cnn(C)c2C(=O)Nc2ccn3cc(-c4ccccc4)nc3n2)on1]

The title compound was obtained in analogy to example 29, using C-(3-ethyl-isoxazol-5-yl)-methylamine in the last step. MS (m/e)=471.2 [M+H⁺].

Example 161

N4-((2-methoxypyridin-3-yl)methyl)-1-methyl-N5-(2-phenylimidazo[1,2-a]pyrimidin-7-yl)-1H-pyrazole-4,5-dicarboxamide

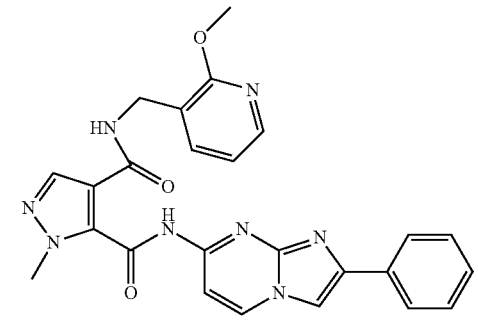 [SMILES: COc1ncccc1CNC(=O)c1cnn(C)c1C(=O)Nc1ccn2cc(-c3ccccc3)nc2n1]

The title compound was obtained in analogy to example 29, using C-(2-methoxy-pyridin-3-yl)-methylamine in the last step. MS (m/e)=483.3 [M+H⁺].

Example 162

N4-benzyl-1-methyl-N5-(2-phenylimidazo[1,2-a]pyrimidin-7-yl)-1H-pyrazole-4,5-dicarboxamide

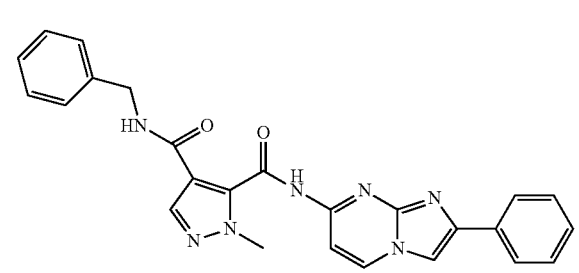 [SMILES: Cn1ncc(C(=O)NCc2ccccc2)c1C(=O)Nc1ccn2cc(-c3ccccc3)nc2n1]

The title compound was obtained in analogy to example 29, using benzylamine in the last step. MS (m/e)=452.2 [M+H⁺].

Example 163

1-methyl-N4-((2-methylthiazol-4-yl)methyl)-N5-(2-phenylimidazo[1,2-a]pyrimidin-7-yl)-1H-pyrazole-4,5-dicarboxamide

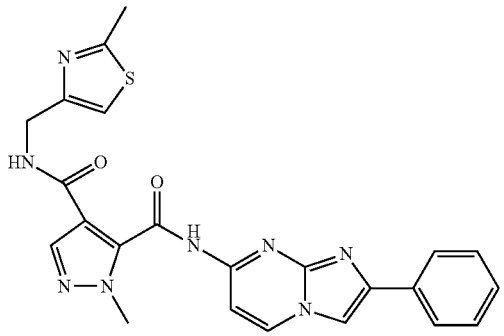 [SMILES: Cc1nc(CNC(=O)c2cnn(C)c2C(=O)Nc2ccn3cc(-c4ccccc4)nc3n2)cs1]

The title compound was obtained in analogy to example 29, using C-(2-methyl-thiazol-4-yl)-methylamine in the last step. MS (m/e)=473.2 [M+H⁺].

Example 164

1-methyl-N5-(2-phenylimidazo[1,2-a]pyrimidin-7-yl)-N4-((1-propyl-1H-pyrazol-3-yl)methyl)-1H-pyrazole-4,5-dicarboxamide

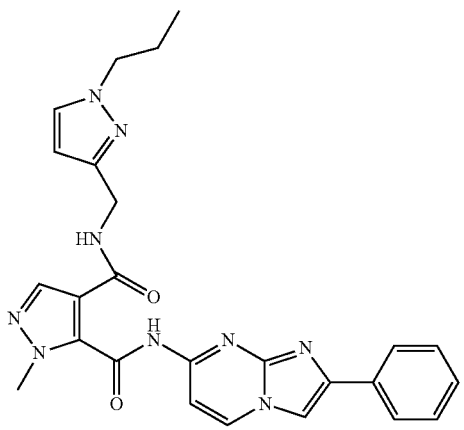 [SMILES: CCCn1ccc(CNC(=O)c2cnn(C)c2C(=O)Nc2ccn3cc(-c4ccccc4)nc3n2)n1]

The title compound was obtained in analogy to example 29, using C-(1-propyl-1H-pyrazol-3-yl)-methylamine in the last step. MS (m/e)=484.4 [M+H⁺].

Example 165

N4-((2-cyclopropyl-5-methyloxazol-4-yl)methyl)-1-methyl-N5-(2-phenylimidazo[1,2-a]pyrimidin-7-yl)-1H-pyrazole-4,5-dicarboxamide

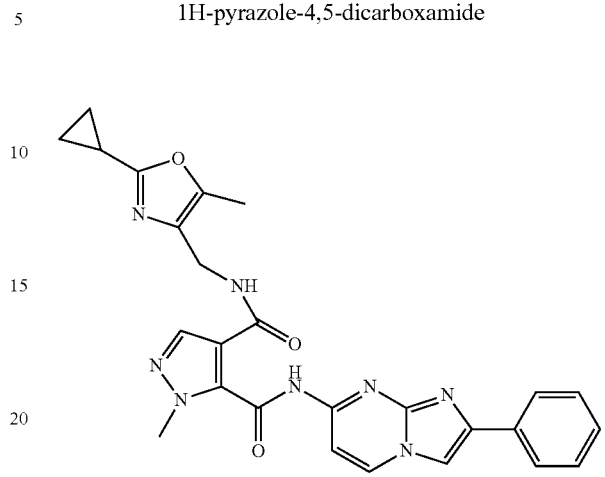

The title compound was obtained in analogy to example 29, using (2-cyclopropyl-5-methyloxazol-4-yl)methanamine in the last step. MS (m/e)=497.3 [M+H⁺].

Example 166

N4-((5-cyclopropyl-1,2,4-oxadiazol-3-yl)methyl)-1-methyl-N5-(2-phenylimidazo[1,2-a]pyrimidin-7-yl)-1H-pyrazole-4,5-dicarboxamide

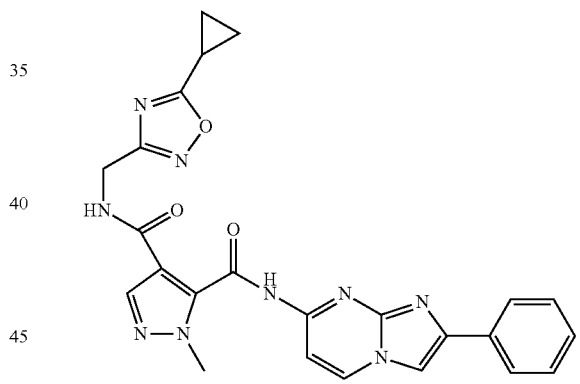

The title compound was obtained in analogy to example 29, using C-(5-cyclopropyl-[1,2,4]oxadiazol-3-yl)-methylamine in the last step. MS (m/e)=484.4 [M+H⁺].

Example 167

N4-((3-cyclopropyl-1,2,4-oxadiazol-5-yl)methyl)-1-methyl-N5-(2-phenylimidazo[1,2-a]pyrimidin-7-yl)-1H-pyrazole-4,5-dicarboxamide

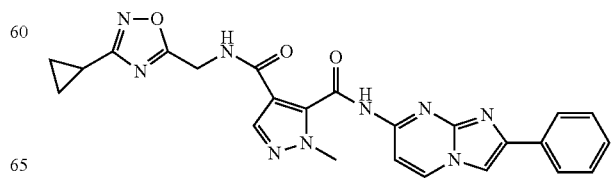

The title compound was obtained in analogy to example 29, using C-(3-cyclopropyl-[1,2,4]oxadiazol-5-yl)-methylamine in the last step. MS (m/e)=484.4 [M+H⁺].

Example 168

1-methyl-N-4-((5-methyl-1,2,4-oxadiazol-3-yl)methyl)-N5-(2-phenylimidazo[1,2-a]pyrimidin-7-yl)-1H-pyrazole-4,5-dicarboxamide

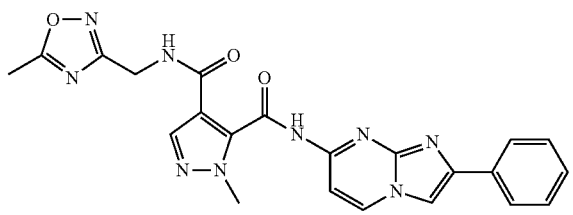 [SMILES: Cc1nc(CNC(=O)c2cnn(C)c2C(=O)Nc2ccn3cc(-c4ccccc4)nc3n2)no1]

The title compound was obtained in analogy to example 29, using C-(5-methyl-[1,2,4]oxadiazol-3-yl)-methylamine in the last step. MS (m/e)=458.4 [M+H⁺].

Example 169

1-methyl-4-(2-methyl-2,4,5,6-tetrahydropyrrolo[3,4-c]pyrazole-5-carbonyl)-N-(2-phenylimidazo[1,2-a]pyrimidin-7-yl)-1H-pyrazole-5-carboxamide

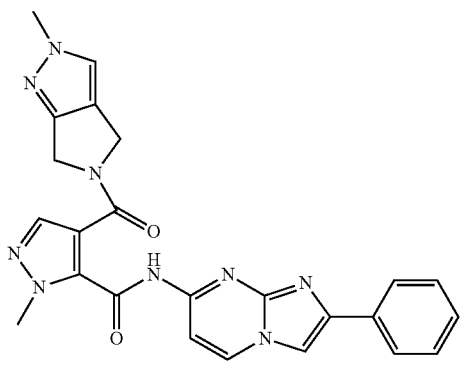 [SMILES: Cn1cc2c(n1)CN(C(=O)c1cnn(C)c1C(=O)Nc1ccn3cc(-c4ccccc4)nc3n1)C2]

The title compound was obtained in analogy to example 29, using 2-methyl-2,4,5,6-tetrahydro-pyrrolo[3,4-c]pyrazole in the last step. MS (m/e)=468.3 [M+H⁺].

Example 170

N4-(benzo[d]oxazol-2-ylmethyl)-1-methyl-N5-(2-phenylimidazo[1,2-a]pyrimidin-7-yl)-1H-pyrazole-4,5-dicarboxamide

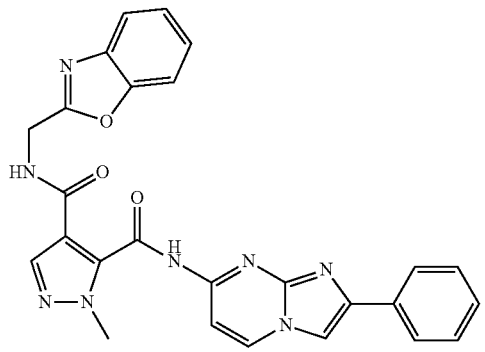 [SMILES: Cn1ncc(C(=O)NCc2nc3ccccc3o2)c1C(=O)Nc1ccn2cc(-c3ccccc3)nc2n1]

The title compound was obtained in analogy to example 29, using C-benzooxazol-2-yl-methylamine in the last step. MS (m/e)=493.3 [M+H⁺].

Example 171

N4-((3-isopropyl-1,2,4-oxadiazol-5-yl)methyl)-1-methyl-N5-(2-phenylimidazo[1,2-a]pyrimidin-7-yl)-1H-pyrazole-4,5-dicarboxamide

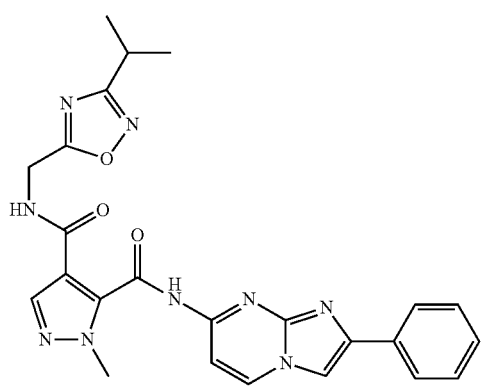 [SMILES: CC(C)c1noc(CNC(=O)c2cnn(C)c2C(=O)Nc2ccn3cc(-c4ccccc4)nc3n2)n1]

The title compound was obtained in analogy to example 29, using C-(3-isopropyl-[1,2,4]oxadiazol-5-yl)-methylamine in the last step. MS (m/e)=486.5 [M+H⁺].

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

113
Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene Glycol 400 | 150.0 mg |
| Acetic Acid | q.s. ad pH 5.0 |
| Water for injection solutions | ad 1.0 mL |

The active ingredient is dissolved in a mixture of Polyethylene Glycol 400 and water for injection (part). The pH is adjusted to 5.0 by Acetic Acid. The volume is adjusted to 1.0 mL by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

114
Example E

Sachets containing the following ingredients can be manufactured in a conventional manner:

| Compound of formula (I) | 50.0 mg |
|---|---|
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula (I)

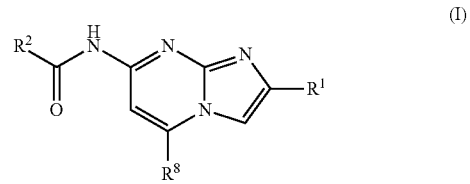

wherein $R^1$ is phenyl or thienyl, wherein said phenyl and said thienyl are optionally substituted by 1 to 3 substituents independently selected from the group consisting of hydroxyl, halogen, lower alkyl, lower alkoxy, lower haloalkyl, lower haloalkoxy, lower alkoxy lower alkyl, —OC(O)-lower alkyl, —OCH$_2$C(O)-lower alkoxy and phenyl;

$R^2$ is 5- or 6-membered monocyclic heteroaryl having 1 to 3 heteroatoms independently selected from N and O, wherein said heteroaryl is optionally substituted by 1 to 3 substituents independently selected from the group consisting of

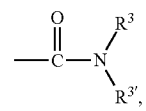

halogen, hydroxyl, nitro, lower alkyl, lower alkenyl, lower alkoxy, lower alkoxy-C(O)—, lower hydroxyalkyl, lower haloalkyl, lower alkoxy lower alkyl, lower alkyl-C(O)—, cycloalkyl, heterocyclyl, aryl, heteroaryl and amino optionally substituted by heteroaryl, wherein two substituents of $R^2$, together with said heteroaryl to which they are attached, may form a 9- or 10-membered bicyclic ring;

$R^3$ and $R^{3'}$ are each independently hydrogen, lower alkyl, lower hydroxyalkyl, lower cyanoalkyl, lower haloalkyl, lower alkoxy lower alkyl, cycloalkyl, cyanocycloalkyl, heterocyclyl or aryl, wherein said lower alkyl is optionally substituted by lower haloalkoxy, cycloalkyl, aryl or heteroaryl, wherein said heteroaryl is optionally substituted by 1 to 3 substituents independently selected from the group consisting of halogen, nitro, cyano, lower alkyl, lower haloalkyl, lower alkoxy and cycloalkyl, and wherein said heterocyclyl is optionally substituted by lower alkyl, or $R^3$ and $R^{3'}$, together with the nitrogen atom to which they are attached, form a heterocyclyl, 2,5-dihydro-1H-pyrrole, 2-methyl-2,4,5,6-tetrahydropyrrolo[3,4-c]pyrazole or 2-oxa-6-azaspiro[3.3]heptane, wherein said heterocyclyl is optionally substituted by 1 to 3 halogen, hydroxyl, oxo, lower alkyl or heteroaryl; and $R^8$ is hydrogen, lower alkyl, lower alkoxy or lower alkoxy lower alkyl;

or a pharmaceutically acceptable salt thereof.

2. A compound of formula (I')

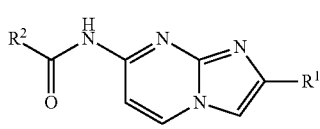

(I')

wherein $R^1$ is phenyl or thienyl, wherein said phenyl and said thienyl are optionally substituted by 1 to 3 substituents independently selected from the group consisting of halogen, lower alkyl, lower alkoxy, lower haloalkyl, lower haloalkoxy and lower alkoxy lower alkyl;

$R^2$ is 5- or 6-membered monocyclic heteroaryl having 1 to 3 heteroatoms independently selected from N and O, wherein said heteroaryl is optionally substituted by 1 to 3 substituents independently selected from the group consisting of

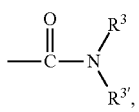

halogen, hydroxyl, nitro, lower alkyl, lower alkoxy, lower alkoxy-C(O)—, lower hydroxyalkyl, lower haloalkyl, lower alkoxy lower alkyl, lower alkyl-C(O)—, cycloalkyl, heterocyclyl, aryl, heteroaryl and amino optionally substituted by heteroaryl, wherein two substituents of $R^2$, together with said heteroaryl to which they are attached, may form a 9- or 10-membered bicyclic ring; and $R^3$ and $R^{3'}$ are each independently hydrogen, lower alkyl optionally substituted by cycloalkyl, lower hydroxyalkyl, lower cyanoalkyl, lower haloalkyl, lower alkoxy lower alkyl, cycloalkyl or heterocyclyl, or $R^3$ and $R^{3'}$, together with the nitrogen atom to which they are attached, form a heterocyclyl optionally substituted by 1 to 3 halogen, hydroxyl or oxo;

or a pharmaceutically acceptable salt thereof.

3. The compound of claim 1, wherein $R^1$ is selected from the group consisting of:

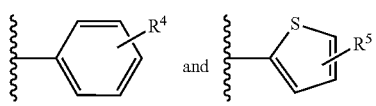

wherein $R^4$ is hydrogen, hydroxyl, halogen, lower alkoxy, lower haloalkoxy, —OC(O)-lower alkyl, —OCH$_2$C(O)-lower alkoxy or phenyl; and $R^5$ is halogen.

4. The compound of claim 1, wherein $R^8$ is hydrogen or lower alkoxy lower alkyl.

5. The compound of claim 1, having formula (Ia)

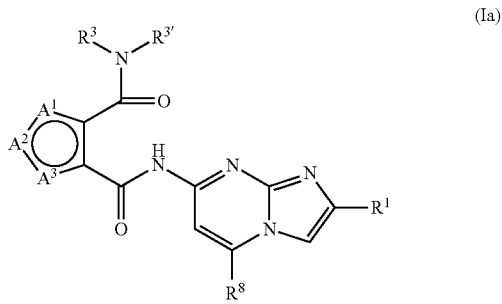

wherein $A^1$ is —NH—, —N=, —NR$^6$— or —CH=;

$A^2$ is —N= or —NR$^{6'}$—;

$A^3$ is —N=, —NR$^{6''}$— or —CH=;

$R^6$ is lower alkyl;

$R^{6'}$ is lower alkyl;

$R^{6''}$ is lower alkyl or lower alkenyl;

$R^1$ is phenyl or thienyl, wherein said phenyl and said thienyl are optionally substituted by 1 to 3 substituents independently selected from the group consisting of hydroxyl, halogen, lower alkoxy, lower haloalkoxy, —OC(O)-lower alkyl, —OCH$_2$C(O)-lower alkoxy and phenyl;

$R^3$ and $R^{3'}$ are each independently hydrogen, lower alkyl, lower hydroxyalkyl, lower cyanoalkyl, lower haloalkyl, lower alkoxy lower alkyl, cycloalkyl, cyanocycloalkyl, heterocyclyl or aryl, wherein said lower alkyl is optionally substituted by lower haloalkoxy, cycloalkyl, aryl or heteroaryl, wherein said heteroaryl is optionally substituted by 1 to 3 substituents independently selected from the group consisting of halogen, nitro, cyano, lower alkyl, lower haloalkyl, lower alkoxy and cycloalkyl, and wherein said heterocyclyl is optionally substituted by lower alkyl, or $R^3$ and $R^{3'}$, together with the nitrogen atom to which they are attached, form a heterocyclyl, 2,5-dihydro-1H-pyrrole, 2-methyl-2,4,5,6-tetrahydropyrrolo[3,4-c]pyrazole or 2-oxa-6-azaspiro[3.3]heptane, wherein said heterocyclyl is optionally substituted by 1 to 3 halogen, hydroxyl, oxo, lower alkyl or heteroaryl; and $R^8$ is hydrogen, lower alkyl, lower alkoxy or lower alkoxy lower alkyl.

6. The compound of claim 5, selected from the group consisting of:

5-(Azetidine-1-carbonyl)-1H-[1,2,3]triazole-4-carboxylic acid (2-phenyl-imidazo[1,2-a]pyrimidin-7-yl)-amide, 1H-[1,2,3]Triazole-4,5-dicarboxylic acid 5-(ethyl-methyl-amide) 4-[(2-phenyl-imidazo[1,2-a]pyrimidin-7-yl)-amide], 4-(Azetidine-1-carbonyl)-2-methyl-2H-pyrazole-3-carboxylic acid (2-phenyl-imidazo[1,2-a]pyrimidin-7-yl)-amide, 2-Methyl-4-(morpholine-4-carbonyl)-2H-pyrazole-3-carboxylic acid (2-phenyl-imidazo[1,2-a]pyrimidin-7-yl)-amide, 2-Methyl-2H-pyrazole-3,4-dicarboxylic acid 4-methylamide 3-[(2-phenyl-imidazo[1,2-a]pyrimidin-7-yl)-amide], 2-Methyl-2H-pyrazole-3,4-dicarboxylic acid 3-{[2-(3-chloro-phenyl)-imidazo[1,2-a]pyrimidin-7-yl]-amide}-4-methylamide,
2-Methyl-2H-pyrazole-3,4-dicarboxylic acid 3-{[2-(4-fluoro-phenyl)-imidazo[1,2-a]pyrimidin-7-yl]-amide}-4-methylamide,
4-(3,3-Difluoro-azetidine-1-carbonyl)-2-methyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-hydroxy-ethyl)-amide]3-[(2-phenyl-imidazo[1,2-a]pyrimidin-7-yl)-amide],
4-(3-Hydroxy-azetidine-1-carbonyl)-2-methyl-2H-pyrazole-3-carboxylic acid (2-phenyl-imidazo[1,2-a]pyrimidin-7-yl)-amide, and
4-(1,1-Dioxo-1λ6-thiomorpholine-4-carbonyl)-2-methyl-2H-pyrazole-3-carboxylic acid (2-phenyl-imidazo[1,2-a]pyrimidin-7-yl)-amide or a pharmaceutically acceptable salt thereof.

7. The compound of claim 5, selected from the group consisting of:
2-Methyl-2H-pyrazole-3,4-dicarboxylic acid 4-[(3-hydroxy-propyl)-amide]3-[(2-phenyl-imidazo[1,2-a]pyrimidin-7-yl)-amide],
2-Methyl-2H-pyrazole-3,4-dicarboxylic acid 4-[(3-methoxy-propyl)-amide]3-[(2-phenyl-imidazo[1,2-a]pyrimidin-7-yl)-amide],
2-Methyl-2H-pyrazole-3,4-dicarboxylic acid 3-[(2-phenyl-imidazo[1,2-a]pyrimidin-7-yl)-amide]-4-[(tetrahydro-furan-3-yl)-amide],
2-Methyl-2H-pyrazole-3,4-dicarboxylic acid 4-[(2-hydroxy-1-methyl-ethyl)-amide]3-[(2-phenyl-imidazo[1,2-a]pyrimidin-7-yl)-amide],
2-Methyl-2H-pyrazole-3,4-dicarboxylic acid 4-[(2-hydroxy-propyl)-amide]3-[(2-phenyl-imidazo[1,2-a]pyrimidin-7-yl)-amide],
4-(Azetidine-1-carbonyl)-2-methyl-2H-pyrazole-3-carboxylic acid [2-(3-methoxy-phenyl)-imidazo[1,2-a]pyrimidin-7-yl]-amide,
2-Methyl-2H-pyrazole-3,4-dicarboxylic acid 4-[(2-methoxy-ethyl)-amide]3-[(2-phenyl-imidazo[1,2-a]pyrimidin-7-yl)-amide],
2-Methyl-2H-pyrazole-3,4-dicarboxylic acid 4-diethylamide 3-[(2-phenyl-imidazo[1,2-a]pyrimidin-7-yl)-amide],
2-Methyl-4-(pyrrolidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-(ethyl-methyl-amide) 3-[(2-phenyl-imidazo[1,2-a]pyrimidin-7-yl)-amide], and
2-Methyl-2H-pyrazole-3,4-dicarboxylic acid 4-ethylamide 3-[(2-phenyl-imidazo[1,2-a]pyrimidin-7-yl)-amide]

or a pharmaceutically acceptable salt thereof.

8. The compound of claim 5, selected from the group consisting of:
2-Methyl-2H-pyrazole-3,4-dicarboxylic acid 4-cyclopropylamide 3-[(2-phenyl-imidazo[1,2-a]pyrimidin-7-yl)-amide],
2-Methyl-4-(piperidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-hydroxy-ethyl)-methyl-amide]3-[(2-phenyl-imidazo[1,2-a]pyrimidin-7-yl)-amide],
2-Methyl-2H-pyrazole-3,4-dicarboxylic acid 4-(isopropyl-methyl-amide) 3-[(2-phenyl-imidazo[1,2-a]pyrimidin-7-yl)-amide],
2-Methyl-2H-pyrazole-3,4-dicarboxylic acid 4-[(2-methoxy-ethyl)-methyl-amide]3-[(2-phenyl-imidazo[1,2-a]pyrimidin-7-yl)-amide],
2-Methyl-2H-pyrazole-3,4-dicarboxylic acid 4-(methyl-propyl-amide) 3-[(2-phenyl-imidazo[1,2-a]pyrimidin-7-yl)-amide],
2-Methyl-2H-pyrazole-3,4-dicarboxylic acid 3-[(2-phenyl-imidazo[1,2-a]pyrimidin-7-yl)-amide]-4-propylamide,
2-Methyl-2H-pyrazole-3,4-dicarboxylic acid 4-cyclopropylmethyl-amide 3-[(2-phenyl-imidazo[1,2-a]pyrimidin-7-yl)-amide],
2-Methyl-2H-pyrazole-3,4-dicarboxylic acid 4-cyclobutylamide 3-[(2-phenyl-imidazo[1,2-a]pyrimidin-7-yl)-amide],
2-Methyl-2H-pyrazole-3,4-dicarboxylic acid 4-isopropylamide 3-[(2-phenyl-imidazo[1,2-a]pyrimidin-7-yl)-amide], and
4-(Azetidine-1-carbonyl)-2-methyl-2H-pyrazole-3-carboxylic acid [2-(3-trifluoromethoxy-phenyl)-imidazo[1,2-a]pyrimidin-7-yl]-amide or a pharmaceutically acceptable salt thereof.

9. The compound of claim 5, selected from the group consisting of:
4-(Azetidine-1-carbonyl)-2-methyl-2H-pyrazole-3-carboxylic acid [2-(3-chloro-phenyl)-imidazo[1,2-a]pyrimidin-7-yl]-amide,
2-Ethyl-2H-pyrazole-3,4-dicarboxylic acid 4-methylamide 3-[(2-phenyl-imidazo[1,2-a]pyrimidin-7-yl)-amide],
1H-[1,2,3]Triazole-4,5-dicarboxylic acid 5-methylamide 4-[(2-phenyl-imidazo[1,2-a]pyrimidin-7-yl)-amide],
3-(Azetidine-1-carbonyl)-1-methyl-1H-pyrazole-4-carboxylic acid (2-phenyl-imidazo[1,2-a]pyrimidin-7-yl)-amide,
1-Methyl-1H-pyrazole-3,4-dicarboxylic acid 3-(ethyl-methyl-amide) 4-[(2-phenyl-imidazo[1,2-a]pyrimidin-7-yl)-amide],
1-Methyl-1H-pyrazole-3,4-dicarboxylic acid 4-(ethyl-methyl-amide) 3-[(2-phenyl-imidazo[1,2-a]pyrimidin-7-yl)-amide],
4-(Azetidine-1-carbonyl)-2-ethyl-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-cyano-ethyl)-methyl-amide]3-[(2-phenyl-imidazo[1,2-a]pyrimidin-7-yl)-amide],
2-Methyl-2H-pyrazole-3,4-dicarboxylic acid 4-(isobutyl-methyl-amide) 3-[(2-phenyl-imidazo[1,2-a]pyrimidin-7-yl)-amide],
2-Methyl-2H-pyrazole-3,4-dicarboxylic acid 4-[(2-hydroxy-2-methyl-propyl)-amide]3-[(2-phenyl-imidazo[1,2-a]pyrimidin-7-yl)-amide], and
2-Ethyl-2H-pyrazole-3,4-dicarboxylic acid 4-(ethyl-methyl-amide) 3-[(2-phenyl-imidazo[1,2-a]pyrimidin-7-yl)-amide]

or a pharmaceutically acceptable salt thereof.

10. The compound of claim 5, selected from the group consisting of:
4-(Azetidine-1-carbonyl)-2-methyl-2H-pyrazole-3-carboxylic acid [2-(5-chloro-thiophen-2-yl)-imidazo[1,2-a]pyrimidin-7-yl]-amide, 2-Methyl-2H-pyrazole-3,4-dicarboxylic acid 4-dimethylamide 3-[(2-phenyl-imidazo[1,2-a]pyrimidin-7-yl)-amide],
4-(azetidine-1-carbonyl)-N-(2-(3-(fluoromethoxy)phenyl)imidazo[1,2-a]pyrimidin-7-yl)-1-methyl-1H-pyrazole-5-carboxamide,
4-(Azetidine-1-carbonyl)-2-methyl-2H-pyrazole-3-carboxylic acid [2-(3-hydroxy-phenyl)-imidazo[1,2-a]pyrimidin-7-yl]-amide,
N5-(2-(3-hydroxyphenyl)imidazo[1,2-a]pyrimidin-7-yl)-N4,N4,1-trimethyl-1H-pyrazole-4,5-dicarboxamide,
2-Methyl-2H-pyrazole-3,4-dicarboxylic acid 4-dimethylamide 3-{[2-(3-methoxy-phenyl)-imidazo[1,2-a]pyrimidin-7-yl]-amide},
N4-ethyl-N5-(2-(3-(fluoromethoxy)phenyl)imidazo[1,2-a]pyrimidin-7-yl)-N4,1-dimethyl-1H-pyrazole-4,5-dicarboxamide,
N4-ethyl-N5-(2-(3-methoxyphenyl)imidazo[1,2-a]pyrimidin-7-yl)-N4,1-dimethyl-1H-pyrazole-4,5-dicarboxamide,
N5-(2-(3-(fluoromethoxy)phenyl)imidazo[1,2-a]pyrimidin-7-yl)-N4,N4,1-trimethyl-1H-pyrazole-4,5-dicarboxamide,
N4-ethyl-N5-(2-(3-(2-fluoroethoxy)phenyl)imidazo[1,2-a]pyrimidin-7-yl)-N4,1-dimethyl-1H-pyrazole-4,5-dicarboxamide, and
4-(3-fluoroazetidine-1-carbonyl)-N-(2-(3-(2-fluoroethoxy)phenyl)imidazo[1,2-a]pyrimidin-7-yl)-1-methyl-1H-pyrazole-5-carboxamide
or a pharmaceutically acceptable salt thereof.

11. The compound of claim 5, selected from the group consisting of:
4-(azetidine-1-carbonyl)-N-(2-(3-fluorophenyl)imidazo[1,2-a]pyrimidin-7-yl)-1-methyl-1H-pyrazole-5-carboxamide,
4-(3-fluoro azetidine-1-carbonyl)-N-(2-(3-fluorophenyl)imidazo[1,2-a]pyrimidin-7-yl)-1-methyl-1H-pyrazole-5-carboxamide,
3-(7-(4-(dimethylcarbamoyl)-1-methyl-1H-pyrazole-5-carboxamido)imidazo[1,2-a]pyrimidin-2-yl)phenyl acetate,
N5-(2-(3-fluorophenyl)imidazo[1,2-a]pyrimidin-7-yl)-N4,N4,1-trimethyl-1H-pyrazole-4,5-dicarboxamide,
N4-(2-fluoroethyl)-N4,1-dimethyl-N5-(2-phenylimidazo[1,2-a]pyrimidin-7-yl)-1H-pyrazole-4,5-dicarboxamide,
2-Methyl-2H-pyrazole-3,4-dicarboxylic acid 3-({2-[3-(2-fluoro-ethoxy)-phenyl]-imidazo[1,2-a]pyrimidin-7-yl}-amide) 4-[(2-methoxy-ethyl)-methyl-amide],
N4-ethyl-N5-(2-(3-fluorophenyl)imidazo[1,2-a]pyrimidin-7-yl)-N4,1-dimethyl-1H-pyrazole-4,5-dicarboxamide,
4-(3-fluoroazetidine-1-carbonyl)-N-(2-(3-methoxyphenyl)imidazo[1,2-a]pyrimidin-7-yl)-1-methyl-1H-pyrazole-5-carboxamide,
2-Methyl-2H-pyrazole-3,4-dicarboxylic acid 3-{[2-(3-fluoromethoxy-phenyl)-imidazo[1,2-a]pyrimidin-7-yl]-amide}-4-[(2-methoxy-ethyl)-methyl-amide],
methyl 2-(3-(7-(4-(ethyl(methyl)carbamoyl)-1-methyl-1H-pyrazole-5-carboxamido)imidazo[1,2-a]pyrimidin-2-yl)phenoxy)acetate, and
2-Methyl-2H-pyrazole-3,4-dicarboxylic acid 4-[(2-methoxy-ethyl)-methyl-amide]3-{[2-(3-methoxy-phenyl)-imidazo[1,2-a]pyrimidin-7-yl]-amide}
or a pharmaceutically acceptable salt thereof.

12. The compound of claim 5, selected from the group consisting of:
2-Methyl-2H-pyrazole-3,4-dicarboxylic acid 4-dimethylamide 3-({2-[3-(2-fluoro-ethoxy)-phenyl]-imidazo[1,2-a]pyrimidin-7-yl}-amide),
4-(Azetidine-1-carbonyl)-2-methyl-2H-pyrazole-3-carboxylic acid {2-[3-(2-fluoro-ethoxy)-phenyl]-imidazo[1,2-a]pyrimidin-7-yl}-amide,
N4-(2-fluoroethyl)-N5-(2-(3-fluorophenyl)imidazo[1,2-a]pyrimidin-7-yl)-N4,1-dimethyl-1H-pyrazole-4,5-dicarboxamide,
3-(7-(4-(azetidine-1-carbonyl)-1-methyl-1H-pyrazole-5-carboxamido)imidazo[1,2-a]pyrimidin-2-yl)phenyl acetate,
N4-(2-(2-fluoroethoxy)ethyl)-N4,1-dimethyl-N5-(2-phenylimidazo[1,2-a]pyrimidin-7-yl)-1H-pyrazole-4,5-dicarboxamide,
2-Methyl-2H-pyrazole-3,4-dicarboxylic acid 3-{[2-(3-fluoro-phenyl)-imidazo[1,2-a]pyrimidin-7-yl]-amide}-4-[(2-methoxy-ethyl)-methyl-amide],
N4-(2-fluoroethyl)-N5-(2-(3-(fluoromethoxy)phenyl)imidazo[1,2-a]pyrimidin-7-yl)-N4,1-dimethyl-1H-pyrazole-4,5-dicarboxamide,
N4-(2-fluoroethoxy)ethyl)-N5-(2-(3-(2-fluoroethoxy)phenyl)imidazo[1,2-a]pyrimidin-7-yl)-N4,1-dimethyl-1H-pyrazole-4,5-dicarboxamide,
N4-(2-(2-fluoroethoxy)ethyl)-N5-(2-(3-methoxyphenyl)imidazo[1,2-a]pyrimidin-7-yl)-N4,1-dimethyl-1H-pyrazole-4,5-dicarboxamide,
N4-(2-fluoroethyl)-N5-(2-(3-methoxyphenyl)imidazo[1,2-a]pyrimidin-7-yl)-N4,1-dimethyl-1H-pyrazole-4,5-dicarboxamide, and
1-methyl-N4-(oxazol-4-ylmethyl)-N5-(2-phenylimidazo[1,2-a]pyrimidin-7-yl)-1H-pyrazole-4,5-dicarboxamide
or a pharmaceutically acceptable salt thereof.

13. The compound of claim 5, selected from the group consisting of:
N4-((1H-pyrazol-5-yl)methyl)-1-methyl-N5-(2-phenylimidazo[1,2-a]pyrimidin-7-yl)-1H-pyrazole-4,5-dicarboxamide,
4-(2,5-dihydro-1H-pyrrole-1-carbonyl)-1-methyl-N-(2-phenylimidazo[1,2-a]pyrimidin-7-yl)-1H-pyrazole-5-carboxamide,
4-(3-fluoroazetidine-1-carbonyl)-1-methyl-N-(2-phenylimidazo[1,2-a]pyrimidin-7-yl)-1H-pyrazole-5-carboxamide,
1-methyl-4-(2-methylpyrrolidine-1-carbonyl)-N-(2-phenylimidazo[1,2-a]pyrimidin-7-yl)-1H-pyrazole-5-carboxamide,
4-(azetidine-1-carbonyl)-N-(2-(3-bromophenyl)imidazo[1,2-a]pyrimidin-7-yl)-1-methyl-1H-pyrazole-5-carboxamide,
1-methyl-N5-(2-phenylimidazo[1,2-a]pyrimidin-7-yl)-N4-(pyridin-2-ylmethyl)-1H-pyrazole-4,5-dicarboxamide,
N4-(cyanomethyl)-N4,1-dimethyl-N5-(2-phenylimidazo[1,2-a]pyrimidin-7-yl)-1H-pyrazole-4,5-dicarboxamide,
1-allyl-4-(azetidine-1-carbonyl)-N-(2-phenylimidazo[1,2-a]pyrimidin-7-yl)-1H-pyrazole-5-carboxamide,
1-methyl-N4-((5-methyl-1H-pyrazol-3-yl)methyl)-N5-(2-phenylimidazo[1,2-a]pyrimidin-7-yl)-1H-pyrazole-4,5-dicarboxamide,
1-methyl-N4-(oxazol-2-ylmethyl)-N5-(2-phenylimidazo[1,2-a]pyrimidin-7-yl)-1H-pyrazole-4,5-dicarboxamide, N4-(2-fluoroethyl)-1-methyl-N5-(2-phenylimidazo[1,2-a]pyrimidin-7-yl)-1H-pyrazole-4,5-dicarboxamide, and 1-methyl-N-4-((5-methylthiazol-2-yl)methyl)-N5-(2-phenylimidazo[1,2-a]pyrimidin-7-yl)-1H-pyrazole-4,5-dicarboxamide or a pharmaceutically acceptable salt thereof.

14. The compound of claim 5, selected from the group consisting of:

N4-(cyanomethyl)-1-methyl-N 5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N4-(3,3,3-trifluoropropyl)-1H-pyrazole-4,5-dicarboxamide, 1-methyl-N-4-((3-methylisoxazol-5-yl)methyl)-N5-(2-phenylimidazo[1,2-a]pyrimidin-7-yl)-1H-pyrazole-4,5-dicarboxamide, 4-(azetidine-1-carbonyl)-N-(2-(biphenyl-3-yl)imidazo[1,2-a]pyrimidin-7-yl)-1-methyl-1H-pyrazole-5-carboxamide, N4-(2,2-difluoroethyl)-1-methyl-N5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N4-(2,2,2-trifluoroethyl)-1H-pyrazole-4,5-dicarboxamide, N4-(isoxazol-5-ylmethyl)-1-methyl-N5-(2-phenylimidazo[1,2-a]pyrimidin-7-yl)-1H-pyrazole-4,5-dicarboxamide, 1-methyl-N-(2-phenylimidazo[1,2-a]pyrimidin-7-yl)-4-(2-oxa-6-azaspiro[3.3]heptane-6-carbonyl)-1H-pyrazole-5-carboxamide, 1-methyl-N4-phenyl-N5-(2-phenylimidazo[1,2-a]pyrimidin-7-yl)-1H-pyrazole-4,5-dicarboxamide, 1-methyl-N4-(3-methyloxetan-3-yl)-N5-(2-phenylimidazo[1,2-a]pyrimidin-7-yl)-1H-pyrazole-4,5-dicarboxamide, N4,1-dimethyl-N5-(2-phenylimidazo[1,2-a]pyrimidin-7-yl)-N4-(pyridin-2-ylmethyl)-1H-pyrazole-4,5-dicarboxamide, and N4-((5-bromopyridin-2-yl)methyl)-N4,1-dimethyl-N5-(2-phenylimidazo[1,2-a]pyrimidin-7-yl)-1 H-pyrazole-4,5-dicarboxamide or a pharmaceutically acceptable salt thereof.

15. The compound of claim 5, selected from the group consisting of:

1-methyl-N-(2-phenylimidazo[1,2-a]pyrimidin-7-yl)-4-(3-(pyridin-3-yl)morpholine-4-carbonyl)-1H-pyrazole-5-carboxamide, N4-tert-butyl-1-methyl-N5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N4-(1-(pyridin-3-yl)ethyl)-1H-pyrazole-4,5-dicarboxamide, N4-((1,3-dimethyl-4-nitro-1H-pyrazol-5-yl)methyl)-1-methyl-N5-(2-phenylimidazo[1,2-a]pyrimidin-7-yl)-1H-pyrazole-4,5-dicarboxamide, N5-(oxetan-3-yl)-N4-(2-phenylimidazo[1,2-a]pyrimidin-7-yl)-1H-1,2,3-triazole-4,5-dicarboxamide, N4-((6-cyanopyridin-3-yl)methyl)-1-methyl-N5-(2-phenylimidazo[1,2-a]pyrimidin-7-yl)-1H-pyrazole-4,5-dicarboxamide, 1-methyl-N-4-((5-methylisoxazol-3-yl)methyl)-N5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N446-(trifluoromethyl)pyridin-3-yl)methyl)-1H-pyrazole-4,5-dicarboxamide, N4-(1-cyanocyclopropyl)-1-methyl-N5-(2-phenylimidazo[1,2-a]pyrimidin-7-yl)-1H-pyrazole-4,5-dicarboxamide, N5-(5-(methoxymethyl)-2-phenylimidazo[1,2-a]pyrimidin-7-yl)-N4,1-dimethyl-1H-pyrazole-4,5-dicarboxamide, N4-((1H-tetrazol-5-yl)methyl)-1-methyl-N5-(2-phenylimidazo[1,2-a]pyrimidin-7-yl)-1H-pyrazole-4,5-dicarboxamide, and 1-methyl-N5-(2-phenylimidazo[1,2-a]pyrimidin-7-yl)-N4-(pyridin-4-ylmethyl)-1H-pyrazole-4,5-dicarboxamide or a pharmaceutically acceptable salt thereof.

16. The compound of claim 5, selected from the group consisting of:

N4-(imidazo[1,2-a]pyridin-2-ylmethyl)-1-methyl-N5-(2-phenylimidazo[1,2-a]pyrimidin-7-yl)-1 H-pyrazole-4,5-dicarboxamide, N5-(2-methoxyethyl)-N4-(2-phenylimidazo[1,2-a]pyrimidin-7-yl)-1H-1,2,3-triazole-4,5-dicarboxamide, N4-((4-cyanothiazol-2-yl)methyl)-1-methyl-N5-(2-phenylimidazo[1,2-a]pyrimidin-7-yl)-1H-pyrazole-4,5-dicarboxamide, N4-((5-cyclopropyl-1H-pyrazol-3-yl)methyl)-1-methyl-N5-(2-phenylimidazo[1,2-a]pyrimidin-7-yl)-1H-pyrazole-4,5-dicarboxamide, N4-(imidazo[2,1-b]thiazol-6-ylmethyl)-1-methyl-N5-(2-phenylimidazo[1,2-a]pyrimidin-7-yl)-1 H-pyrazole-4,5-dicarboxamide, N4-((6-chloropyridin-3-yl)methyl)-1-methyl-N5-(2-phenylimidazo[1,2-a]pyrimidin-7-yl)-1H-pyrazole-4,5-dicarboxamide, 1-methyl-N-4-((5-methylpyridin-2-yl)methyl)-N5-(2-phenylimidazo[1,2-a]pyrimidin-7-yl)-1H-pyrazole-4,5-dicarboxamide, N4-(2-phenylimidazo[1,2-a]pyrimidin-7-yl)-N5-propyl-1H-1,2,3-triazole-4,5-dicarboxamide, 1-methyl-N4-((1-methyl-1H-pyrazol-3-yl)methyl)-N5-(2-phenylimidazo[1,2-a]pyrimidin-7-yl)-1 H-pyrazole-4,5-dicarboxamide, N4-((4-chloro-1-methyl-1H-pyrazol-3-yl)methyl)-1-methyl-N5-(2-phenylimidazo[1,2-a]pyrimidin-7-yl)-1H-pyrazole-4,5-dicarboxamide, N5-cyclopropyl-N4-(2-phenylimidazo[1,2-a]pyrimidin-7-yl)-1H-1,2,3-triazole-4,5-dicarboxamide, and N4-((3-ethylisoxazol-5-yl)methyl)-1-methyl-N5-(2-phenylimidazo[1,2-a]pyrimidin-7-yl)-1H-pyrazole-4,5-dicarboxamide or a pharmaceutically acceptable salt thereof.

17. The compound of claim 5, selected from the group consisting of:

N4-((2-methoxypyridin-3-yl)methyl)-1-methyl-N5-(2-phenylimidazo[1,2-a]pyrimidin-7-yl)-1H-pyrazole-4,5-dicarboxamide, N4-benzyl-1-methyl-N5-(2-phenylimidazo[1,2-a]pyrimidin-7-yl)-1H-pyrazole-4,5-dicarboxamide, 1-methyl-N-4-((2-methylthiazol-4-yl)methyl)-N5-(2-phenylimidazo[1,2-a]pyrimidin-7-yl)-1H-pyrazole-4,5-dicarboxamide, 1-methyl-N5-(2-phenylimidazo[1,2-a]pyrimidin-7-yl)-N4-((1-propyl-1H-pyrazol-3-yl)methyl)-1 H-pyrazole-4,5-dicarboxamide, N4-((2-cyclopropyl-5-methyloxazol-4-yl)methyl)-1-methyl-N5-(2-phenylimidazo[1,2-a]pyrimidin-7-yl)-1H-pyrazole-4,5-dicarboxamide,
N4-((5-cyclopropyl-1,2,4-oxadiazol-3-yl)methyl)-1-methyl-N5-(2-phenylimidazo[1,2-a]pyrimidin-7-yl)-1H-pyrazole-4,5-dicarboxamide,
N4-((3-cyclopropyl-1,2,4-oxadiazol-5-yl)methyl)-1-methyl-N5-(2-phenylimidazo[1,2-a]pyrimidin-7-yl)-1H-pyrazole-4,5-dicarboxamide,
1-methyl-N4-((5-methyl-1,2,4-oxadiazol-3-yl)methyl)-N5-(2-phenylimidazo[1,2-a]pyrimidin-7-yl)-1H-pyrazole-4,5-dicarboxamide,
1-methyl-4-(2-methyl-2,4,5,6-tetrahydropyrrolo[3,4-c]pyrazole-5-carbonyl)-N-(2-phenylimidazo[1,2-a]pyrimidin-7-yl)-1H-pyrazole-5-carboxamide,
N4-(benzo[d]oxazol-2-ylmethyl)-1-methyl-N5-(2-phenylimidazo[1,2-a]pyrimidin-7-yl)-1H-pyrazole-4,5-dicarboxamide, and
N4-((3-isopropyl-1,2,4-oxadiazol-5-yl)methyl)-1-methyl-N5-(2-phenylimidazo[1,2-a]pyrimidin-7-yl)-1H-pyrazole-4,5-dicarboxamide
or a pharmaceutically acceptable salt thereof.

18. The compound of claim 5,
wherein
$R^1$ is phenyl or thienyl, wherein said phenyl and said thienyl are optionally substituted by halogen or lower alkoxy; and
$R^3$ and $R^{3'}$ are each independently lower alkyl or lower alkoxy lower alkyl, or
$R^3$ and $R^{3'}$, together with the nitrogen atom to which they are attached, form an azetidine ring, pyrrolidine ring or piperidine ring, wherein said azetizine ring is optionally substituted by 1 or 2 substituents independently selected from the group consisting of hydroxyl and halogen.

19. The compound of claim 18, selected from the group consisting of:
4-(Azetidine-1-carbonyl)-2-methyl-2H-pyrazole-3-carboxylic acid (2-phenyl-imidazo[1,2-a]pyrimidin-7-yl)-amide,
2-Methyl-4-(morpholine-4-carbonyl)-2H-pyrazole-3-carboxylic acid (2-phenyl-imidazo[1,2-a]pyrimidin-7-yl)-amide,
4-(3,3-Difluoro-azetidine-1-carbonyl)-2-methyl-2H-pyrazole-3-carboxylic acid (2-phenyl-imidazo[1,2-a]pyrimidin-7-yl)-amide,
4-(3-Hydroxy-azetidine-1-carbonyl)-2-methyl-2H-pyrazole-3-carboxylic acid (2-phenyl-imidazo[1,2-a]pyrimidin-7-yl)-amide,
4-(Azetidine-1-carbonyl)-2-methyl-2H-pyrazole-3-carboxylic acid [2-(3-methoxy-phenyl)-imidazo[1,2-a]pyrimidin-7-yl]-amide,
2-Methyl-4-(pyrrolidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-(ethyl-methyl-amide) 3-[(2-phenyl-imidazo[1,2-a]pyrimidin-7-yl)-amide],
2-Methyl-4-(piperidine-1-carbonyl)-2H-pyrazole-3-carboxylic acid (2-phenyl-imidazo[1,2-a]pyrimidin-7-yl)-amide,
2-Methyl-2H-pyrazole-3,4-dicarboxylic acid 4-[(2-methoxy-ethyl)-methyl-amide]3-[(2-phenyl-imidazo[1,2-a]pyrimidin-7-yl)-amide],
4-(Azetidine-1-carbonyl)-2-methyl-2H-pyrazole-3-carboxylic acid [2-(3-chloro-phenyl)-imidazo[1,2-a]pyrimidin-7-yl]-amide,
4-(Azetidine-1-carbonyl)-2-ethyl-2H-pyrazole-3-carboxylic acid (2-phenyl-imidazo[1,2-a]pyrimidin-7-yl)-amide,
2-Ethyl-2H-pyrazole-3,4-dicarboxylic acid 4-(ethyl-methyl-amide) 3-[(2-phenyl-imidazo[1,2-a]pyrimidin-7-yl)-amide],
4-(Azetidine-1-carbonyl)-2-methyl-2H-pyrazole-3-carboxylic acid [2-(5-chloro-thiophen-2-yl)-imidazo[1,2-a]pyrimidin-7-yl]-amide, and
2-Methyl-2H-pyrazole-3,4-dicarboxylic acid 4-dimethylamide 3-[(2-phenyl-imidazo[1,2-a]pyrimidin-7-yl)-amide],
or a pharmaceutically acceptable salt thereof.

20. The compound of claim 1, wherein $R^2$ is

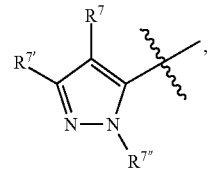

wherein
$R^7$ is hydrogen, halogen, lower alkoxy-C(O)— or heteroaryl;
$R^{7'}$ is hydrogen, lower alkyl or nitro; and
$R^{7''}$ is lower alkyl, cycloalkyl or aryl.

21. The compound of claim 20, selected from the group consisting of:
4-Chloro-2-methyl-2H-pyrazole-3-carboxylic acid (2-phenyl-imidazo[1,2-a]pyrimidin-7-yl)-amide,
4-Chloro-2,5-dimethyl-2H-pyrazole-3-carboxylic acid (2-phenyl-imidazo[1,2-a]pyrimidin-7-yl)-amide,
2-Phenyl-2H-pyrazole-3-carboxylic acid (2-phenyl-imidazo[1,2-a]pyrimidin-7-yl)-amide,
4-Bromo-2,5-dimethyl-2H-pyrazole-3-carboxylic acid (2-phenyl-imidazo[1,2-a]pyrimidin-7-yl)-amide,
4-Bromo-2-methyl-2H-pyrazole-3-carboxylic acid (2-phenyl-imidazo[1,2-a]pyrimidin-7-yl)-amide,
4-Chloro-2-ethyl-2H-pyrazole-3-carboxylic acid (2-phenyl-imidazo[1,2-a]pyrimidin-7-yl)-amide,
4-Chloro-2-propyl-2H-pyrazole-3-carboxylic acid (2-phenyl-imidazo[1,2-a]pyrimidin-7-yl)-amide,
2-Butyl-4-chloro-2H-pyrazole-3-carboxylic acid (2-phenyl-imidazo[1,2-a]pyrimidin-7-yl)-amide, and
4-Chloro-2-isopropyl-2H-pyrazole-3-carboxylic acid (2-phenyl-imidazo[1,2-a]pyrimidin-7-yl)-amide
or a pharmaceutically acceptable salt thereof.

22. The compound of claim 20, selected from the group consisting of:
2-sec-Butyl-4-chloro-2H-pyrazole-3-carboxylic acid (2-phenyl-imidazo[1,2-a]pyrimidin-7-yl)-amide,
4-Chloro-2-isobutyl-2H-pyrazole-3-carboxylic acid (2-phenyl-imidazo[1,2-a]pyrimidin-7-yl)-amide,
2-Isobutyl-5-nitro-2H-pyrazole-3-carboxylic acid (2-phenyl-imidazo[1,2-a]pyrimidin-7-yl)-amide,
2-Cyclopentyl-5-nitro-2H-pyrazole-3-carboxylic acid (2-phenyl-imidazo[1,2-a]pyrimidin-7-yl)-amide,
2-Ethyl-5-nitro-2H-pyrazole-3-carboxylic acid (2-phenyl-imidazo[1,2-a]pyrimidin-7-yl)-amide,
2-Isopropyl-5-nitro-2H-pyrazole-3-carboxylic acid (2-phenyl-imidazo[1,2-a]pyrimidin-7-yl)-amide,
4-Isoxazol-5-yl-2-methyl-2H-pyrazole-3-carboxylic acid (2-phenyl-imidazo[1,2-a]pyrimidin-7-yl)-amide, and
1-Ethyl-5-(2-phenyl-imidazo[1,2-a]pyrimidin-7-ylcarbamoyl)-1H-pyrazole-4-carboxylic acid ethyl ester
or a pharmaceutically acceptable salt thereof.

23. The compound of claim 1, selected from the group consisting of:
Isoxazole-5-carboxylic acid (2-phenyl-imidazo[1,2-a]pyrimidin-7-yl)-amide,
4,5,6,7-Tetrahydro-benzo[d]isoxazole-3-carboxylic acid (2-phenyl-imidazo[1,2-a]pyrimidin-7-yl)-amide,
5-(2-Phenyl-imidazo[1,2-a]pyrimidin-7-ylcarbamoyl)-3H-[1,2,3]triazole-4-carboxylic acid methyl ester, and
1-Methyl-3-(pyrimidin-5-ylamino)-1H-pyrazole-4-carboxylic acid (2-phenyl-imidazo[1,2-a]pyrimidin-7-yl)-amide,
or a pharmaceutically acceptable salt thereof.

24. The compound of claim 1, wherein $R^2$ is 6-membered heteroaryl selected from the group consisting of:

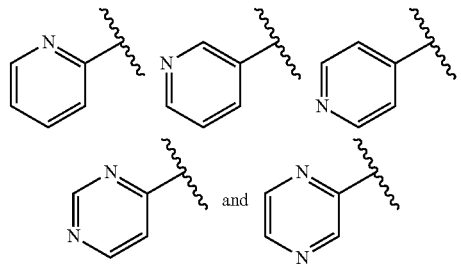

wherein said heteroaryl is substituted by 1 to 3 substituents independently selected from the group consisting of bromo, chloro, methyl, methoxy, cyclopropyl, —C(O)NHCH$_2$CF$_3$,

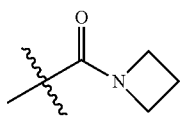 [SMILES: *C(=O)N1CCC1]

and pyrimidin-5-ylamino.

25. The compound of claim 24, selected from the group consisting of:
3,6-Dimethyl-pyridine-2-carboxylic acid (2-phenyl-imidazo[1,2-a]pyrimidin-7-yl)-amide,
2-Chloro-N-(2-phenyl-imidazo[1,2-a]pyrimidin-7-yl)-isonicotinamide,
6-Chloro-pyridine-2-carboxylic acid (2-phenyl-imidazo[1,2-a]pyrimidin-7-yl)-amide,
6-Methoxy-pyridine-2-carboxylic acid (2-phenyl-imidazo[1,2-a]pyrimidin-7-yl)-amide,
5-Bromo-3-methyl-pyridine-2-carboxylic acid (2-phenyl-imidazo[1,2-a]pyrimidin-7-yl)-amide,
4-Bromo-3,6-dimethyl-pyridine-2-carboxylic acid (2-phenyl-imidazo[1,2-a]pyrimidin-7-yl)-amide,
6-Methyl-pyridine-2-carboxylic acid (2-phenyl-imidazo[1,2-a]pyrimidin-7-yl)-amide,
Pyrazine-2,3-dicarboxylic acid 2-[(2-phenyl-imidazo[1,2-a]pyrimidin-7-yl)-amide]3-[(2,2,2-trifluoro-ethyl)-amide],
2-(Azetidine-1-carbonyl)-N-(2-phenyl-imidazo[1,2-a]pyrimidin-7-yl)-nicotinamide,
6-Cyclopropyl-3-(pyrimidin-5-ylamino)-pyridine-2-carboxylic acid (2-phenyl-imidazo[1,2-a]pyrimidin-7-yl)-amide,
2-methoxy-N-(2-phenylimidazo[1,2-a]pyrimidin-7-yl) nicotinamide,
5-chloro-2-methyl-N-(2-phenylimidazo[1,2-a]pyrimidin-7-yl)pyrimidine-4-carboxamide,
2-methyl-N-(2-phenylimidazo[1,2-a]pyrimidin-7-yl) isonicotinamide, and
2-chloro-6-methyl-N-(2-phenylimidazo[1,2-a]pyrimidin-7-yl)isonicotinamide,
or a pharmaceutically acceptable salt thereof.

26. A pharmaceutical composition comprising a therapeutically effective amount of a compound of formula (I)

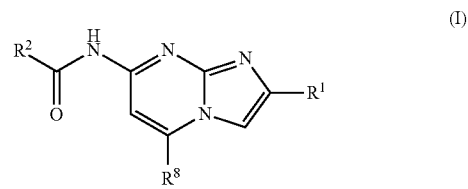

wherein
$R^1$ is phenyl or thienyl, wherein said phenyl and said thienyl are optionally substituted by 1 to 3 substituents independently selected from the group consisting of hydroxyl, halogen, lower alkyl, lower alkoxy, lower haloalkyl, lower haloalkoxy, lower alkoxy lower alkyl, —OC(O)-lower alkyl, —OCH$_2$C(O)-lower alkoxy and phenyl;
$R^2$ is 5- or 6-membered monocyclic heteroaryl having 1 to 3 heteroatoms independently selected from N and O, wherein said heteroaryl is optionally substituted by 1 to 3 substituents independently selected from the group consisting of

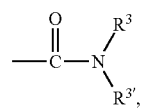

halogen, hydroxyl, nitro, lower alkyl, lower alkenyl, lower alkoxy, lower alkoxy-C(O)—, lower hydroxyalkyl, lower haloalkyl, lower alkoxy lower alkyl, lower alkyl-C(O)—, cycloalkyl, heterocyclyl, aryl, heteroaryl and amino optionally substituted by heteroaryl, wherein two substituents of $R^2$, together with said heteroaryl to which they are attached, may form a 9- or 10-membered bicyclic ring;
$R^3$ and $R^{3'}$ are each independently hydrogen, lower alkyl, lower hydroxyalkyl, lower cyanoalkyl, lower haloalkyl, lower alkoxy lower alkyl, cycloalkyl, cyanocycloalkyl, heterocyclyl or aryl, wherein said lower alkyl is optionally substituted by lower haloalkoxy, cycloalkyl, aryl or heteroaryl, wherein said heteroaryl is optionally substituted by 1 to 3 substituents independently selected from the group consisting of halogen, nitro, cyano, lower alkyl, lower haloalkyl, lower alkoxy and cycloalkyl, and wherein said heterocyclyl is optionally substituted by lower alkyl, or
$R^3$ and $R^{3'}$, together with the nitrogen atom to which they are attached, form a heterocyclyl, 2,5-dihydro-1H-pyrrole, 2-methyl-2,4,5,6-tetrahydropyrrolo[3,4-c]pyrazole or 2-oxa-6-azaspiro[3.3]heptane, wherein said heterocyclyl is optionally substituted by 1 to 3 halogen, hydroxyl, oxo, lower alkyl or heteroaryl; and
$R^8$ is hydrogen, lower alkyl, lower alkoxy or lower alkoxy lower alkyl;
or a pharmaceutically acceptable salt thereof
and a pharmaceutically acceptable carrier.

* * * * *